United States Patent
Homma et al.

(10) Patent No.: US 11,807,664 B2
(45) Date of Patent: Nov. 7, 2023

(54) METHOD FOR PRODUCING CYCLIC ORGANIC COMPOUND

(71) Applicant: Chugai Seiyaku Kabushiki Kaisha, Tokyo (JP)

(72) Inventors: Akie Homma, Tokyo (JP); Zengye Hou, Tokyo (JP); Hisashi Ito, Tokyo (JP); Kiyoshi Sasakura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 759 days.

(21) Appl. No.: 16/612,212

(22) PCT Filed: May 11, 2018

(86) PCT No.: PCT/JP2018/018265
§ 371 (c)(1),
(2) Date: Nov. 8, 2019

(87) PCT Pub. No.: WO2018/207904
PCT Pub. Date: Nov. 15, 2018

(65) Prior Publication Data
US 2021/0147475 A1    May 20, 2021

(30) Foreign Application Priority Data

May 12, 2017 (JP) .................. 2017-095261

(51) Int. Cl.
| | | |
|---|---|---|
| C07K 1/06 | (2006.01) | |
| B01J 19/00 | (2006.01) | |
| B01J 19/18 | (2006.01) | |
| C07K 1/02 | (2006.01) | |
| C07K 7/64 | (2006.01) | |
| C07D 513/08 | (2006.01) | |

(52) U.S. Cl.
CPC .............. *C07K 1/06* (2013.01); *B01J 19/0033* (2013.01); *B01J 19/18* (2013.01); *C07K 1/02* (2013.01); *C07K 7/645* (2013.01); *B01J 2219/002* (2013.01); *B01J 2219/00006* (2013.01); *C07D 513/08* (2013.01)

(58) Field of Classification Search
CPC ......... B01J 19/0033; B01J 19/18; C07K 1/02; C07K 1/06; C07K 7/645
See application file for complete search history.

(56) References Cited

U.S. PATENT DOCUMENTS

| | | | | |
|---|---|---|---|---|
| 5,034,561 A | * | 7/1991 | Sikkenga | .................. C07C 5/31 585/410 |
| 9,428,479 B2 | | 8/2016 | Medoff et al. | |
| 2004/0054191 A1 | * | 3/2004 | Franke | ................. C07D 487/04 548/316.4 |
| 2005/0101654 A1 | | 5/2005 | Weiberth et al. | |
| 2014/0011248 A1 | | 1/2014 | Medoff et al. | |

FOREIGN PATENT DOCUMENTS

| | | |
|---|---|---|
| CN | 101391976 A | 3/2009 |
| EP | 0729944 A2 | 9/1996 |
| EP | 0729944 B1 | 6/2002 |
| EP | 2119718 A1 | 11/2009 |
| EP | 2119718 B1 | 4/2012 |
| EP | 2965761 A1 | 1/2016 |
| WO | WO-9509142 A1 | 4/1995 |
| WO | WO-2006025859 A2 | 3/2006 |
| WO | WO-2006038088 A1 | 4/2006 |
| WO | WO-2007011459 A1 | 1/2007 |
| WO | WO-2008105526 A1 | 9/2008 |
| WO | WO-2010052559 A1 | 5/2010 |

(Continued)

OTHER PUBLICATIONS

Yadav. Organic Process Research and Development, 2016, 20, 1621-1625 (Year: 2016).*
Van Walsum Biotechnology and Bioengineering, 1993, 42, 1175-1180. (Year: 1993).*
Barnard, J. A., "Chapter 2 Types of Ideal Reactor," Comprehensive Chemical Kinetics, 23:47-111 (1985).
Lücke, D., et al., "Synthesis of Natural and Unnatural Cyclooligomeric Depsipeptides Enables by Flow Chemistry," Chem Eur J., 22:4206-4217 (2016).
Otvos, S. B. and Fülöp, F., "Flow chemistry as a versatile tool for the synthesis of triazoles," Catalysis Science & Technology, 5(11):4926-4941 (2015).

(Continued)

*Primary Examiner* — Noble E Jarrell
(74) *Attorney, Agent, or Firm* — Nixon & Vanderhye P.C.

(57) ABSTRACT

An objective of the present invention is to provide methods of producing a cyclic organic compound using a continuous stirred tank reactor(s) (CSTR), the methods being capable of achieving excellent impurity-suppressing effects (quality improvement), reduction in reaction-tank size, continuous production, and such. The present inventors conducted studies on cyclization reactions using a CSTR(s), which had not been conventionally used for cyclization reactions for cyclic compounds. As a result, the inventors have found that the present methods can achieve excellent impurity-suppressing effects (quality improvement), reduction in reaction-tank size, continuous production, and such, as compared with conventional cyclization methods. Furthermore, the present inventors have also found that the above-mentioned improvement effects can efficiently be achieved even in the production of cyclic peptides and heterocyclic compounds by applying simulation methods that had been conventionally used mainly at the fine chemicals plant level to the cyclization reactions of the present invention, thereby experimentally predicting the reaction rate of a cyclization reaction, and setting the flow volume (residence time), the concentrations of precursor and cyclic organic compound, and the temperature for the cyclization reaction and such which affect these conditions, in the cyclization reaction using a CSTR(s).

19 Claims, 8 Drawing Sheets

(56) References Cited

FOREIGN PATENT DOCUMENTS

| WO | WO-2013100132 A1 | 7/2013 |
|---|---|---|
| WO | WO-2013156600 A1 | 10/2013 |
| WO | WO-2013167703 A1 | 11/2013 |
| WO | WO-2014134922 A1 | 9/2014 |
| WO | WO-2014151634 A1 | 9/2014 |

OTHER PUBLICATIONS

Plouffe, P., et al., "From Batch to Continuous Chemical Synthesis—A Toolbox Approach," Org Process Res Dev., 18(11):1286-1294 (2014).
Salvador, C. E. M., et al., "A Sequential Ugi Multicomponent/Cu-Catalyzed Azide-Alkyne Cycloaddition Approach for the Continuous Flow Generation of Cyclic Peptoids," J Org Chem., 80(9):4590-4602 (2015).
Kumar, A. and Gupta, R. K., "Fundamentals of Polymer Engineering," $2^{nd}$ Edition, Polymer Engineering & Science, 22(5):314-323, 2003.
Levenspiel, O., "Chemical Reaction Engineering," $3^{rd}$ Edition, 257-269 (1991).
Hashimoto, Hannou Kougaku, 5-10, 179-197 (1993).
International Search Report dated Aug. 7, 2018 in International Application No. PCT/JP2018/018265.
Josse, T., et al., "Cyclic Polymers by Ring-Closure Strategies," Angew Chem Int Ed., 55:13944-13958 (2016).
Kumar, A. and Gupta, R. K., "Fundamentals of Polymer Engineering," $2^{nd}$ Edition, Polymer Engineering & Science, 22(5):314-323 (1982).
Malesevic, M., et al., "An improved method for the solution cyclization of peptides under pseudo-high dilution conditions," J Biotechnol., 112:73-77 (2004).
Monfette, S., et al., "Getting Ring-Closing Metathesis off the Bench: Reaction-Reactor Matching Transforms Metathesis Efficiency in the Assembly of Large Rings," Chem Eur J., 16:11720-11725 (2010).
Sivanathan, S. and Scherkenbeck, J., "Cyclodepsipeptides: A Rich Source of Biologically Active Compounds for Drug Research," Molecules, 19:12368-12420 (2014).
Suda, A., et al., "Design and synthesis of novel macrocyclic 2-amino-6-arylpyrimidine Hsp90 inhibitors," Bioorg Med Chem Res., 22:1136-1141 (2012).
Trasobares, S., et al., "Upgrading of a Petroleum Residue. Kinetics of Conradson Carbon Residue Conversion," Ind Eng Chem Res., 38:938-943 (1999).
White, T. D., et al., "Development of a Continuous Schotten-Baumann Route to an Acyl Sulfonamide," Org Process Res Dev., 16:939-957 (2012).
Yudin, A. K., "Macrocycles: lessons from the distant past, recent developments, and future directions," Chem Sci., 6:30-49 (2015).
Fogler, "The Chemical Reaction Engineering, $3^{rd}$ Edition—Continuous Stirred Tank Reactor," Chemical Industry Press, 8-13 (2005), with partial English translation.
Roberts, "Chemical Reaction and Chemical Reactor—Ideal Continuous Stirred Tank Reactor," East China University of Science and Technology Press, 38-42 (2011), with partial English translation.

* cited by examiner

METHOD FOR PRODUCING CYCLIC ORGANIC COMPOUND

CROSS-REFERENCE TO RELATED APPLICATIONS

This application is a U.S. National Phase of PCT Application No. PCT/JP2018/018265, filed May 11, 2018, which claims the benefit of Japanese Patent Application No. 2017-095261, filed May 12, 2017, each of which is incorporated herein by reference in its entirety.

TECHNICAL FIELD

The present invention relates to methods for synthesizing macrocyclic organic compounds using a continuous stirred tank reactor(s).

BACKGROUND ART

Macrocyclic compounds (cyclic compounds) refer to compounds including heterocyclic compounds (NPL 1 and PTL 1) and peptide compounds (PTL 2). Macrocyclic compounds are used as natural/unnatural bioactive compounds for pharmaceuticals and such. To supply such pharmaceuticals, manufacture of cyclic compounds is an important mission in the pharmaceutical industry. The manufacture of cyclic compounds cannot be done without going through a cyclization step. The cyclization reaction of a compound refers to a reaction in which a single molecule reacts at two or more reactive sites within the molecule to form a cyclic structure. The binding modes vary; for example, cyclization reactions by various bonds such as an amide bond, ester bond, ether bond, thioether bond, and disulfide bond are known (NPLs 2 and 3, and PTLs 3 and 4).

It is known that in cyclization reactions, increased concentrations cause competition between intramolecular and intermolecular reactions, resulting in generation of dimers or higher order polymeric compounds due to intermolecular reactions. Although concentrations can be kept relatively high in common polymer syntheses, reactions for cyclizing a single molecule are performed under dilute conditions to suppress generation of polymers resulting from intermolecular reactions (NPL 4, and PTLs 1, 5, 6, and 7). This limits the maximum amount of production per batch depending on the size of the reaction tank. Meanwhile, methods for imitating dilute conditions, such as a method of adding a reaction substrate dropwise in small portions to a solution under reaction conditions (reverse dropwise addition), and a method of using a solid-phase-supported substrate in the reaction (on-resin cyclization), are known (NPL 5 and PTLs 8 and 9). These methods allow cyclic compounds of interest to be obtained while avoiding dilute conditions; however, these methods still have limitations on production quantity depending on the size of the reaction tank and the properties of the reaction substrate.

A continuous stirred tank reactor (CSTR) (or mixed flow reactor) refers to a tank reactor when operated continuously. As well as batch reactors, in which the tank reactor is operated in a batch-wise manner, CSTRs are widely used for liquid-phase reactions, gas-phase reactions, and heterogeneous reactions (NPL 6). Ideally, the reaction liquid in the tank reactor is sufficiently mixed by stirring so that the temperature and concentration become uniform in the tank, and is allowed to flow out from the tank at the same concentration and temperature as inside the reactor (Mixed flow). Furthermore, a tubular reactor is a reaction apparatus equipped with a single tube or multiple tubes positioned in parallel, and concentration distribution occurs in the direction of the tube axis (Plug flow). CSTRs and tubular reactors are both flow reactors suitable for continuous production. CSTRs are common reactors in the field of fine chemicals, and are known to be used in polymerization control of polymeric molecules (PTL 10), enzymatic reactions (PTL 11), and such. Furthermore, CSTRs are also known to be combined with other generally known continuous operation techniques such as continuous liquid-liquid separation and crystallization, taking advantage of the continuous operability of CSTRs (NPL 7).

PRIOR ART REFERENCES

Patent Literature

[PTL 1] WO 2008/105526
[PTL 2] WO 2013/100132
[PTL 3] WO 2014/151634
[PTL 4] WO 2014/134922
[PTL 5] WO 2013/167703
[PTL 6] WO 2006/038088
[PTL 7] WO 2010052559
[PTL 8] WO 1995/09142
[PTL 9] WO 2006/025859
[PTL 10] WO 2007/011459
[PTL 11] WO 2013/156600
[NPL 1] Design and synthesis of novel macrocyclic 2-amino-6-arylpyrimidine Hsp90 inhibitors, A. Suda et al., Bioorganic & Medicinal Chemistry Letters 2012, 22, 1136-1141.
[NPL 2] Cyclodepipeptides: A rich source of biologically active compounds for drug research, J. Scherkenbeck et al., Molecules, 2014, 19 (8), 12368.
[NPL 3] Cyclic polymers by ring-closure strategies, P. Gerbaux and O. Coulembier et al., Angew. Chem. Int. Ed. 2016, 55, 13944.
[NPL 4] Macrocycles: lesson from the dis Int pst, recent developments, and future directions. A. K. Yudin, Chem. Sci., 2015, 6, 30.
[NPL 5] An improved method for the solution cyclization of peptides under pseudo-high dilution conditions', Norbert Sewald et al., Journal of Biotechnology 112 (2004) 73-77.
[NPL 6] 1. *Hanno-kogaku* (Reaction Engineering) (revised edition), Kenji Hashimoto, Baihukan, 2. Chemical reaction engineering (third edition), Octave Levenspiel, Wiley.
[NPL 7] Development of a Continuous Schotten-Baumann Route to an Acyl Sulfonamide., Timothy D. White et al., Org. Process Res. Dev., 2012, 16 (5), 939.

SUMMARY OF INVENTION

Problems to be Solved by the Invention

Continuous reactors, which are used for large-scale production in the field of fine chemicals, have never been applied to cyclization reactions of cyclic organic compounds (including heterocyclic compounds), particularly of cyclic peptide pharmaceuticals, in the field of pharmaceuticals. There may be various grounds behind this; for example, many commercially available cyclic peptide pharmaceuticals are highly active, so their large-scale production has been poorly demanded.

Continuous stirred tank reactors (CSTRs) and tubular reactors are known continuous reactors. In tubular reactors, the substrate and product concentrations at the inlet and the outlet are different because of the principle of the reactors. In the case of a tubular reactor, when a heterocyclic compound, peptide compound, or such is cyclized, a relatively dilute solution needs to flow through the reactor, and thus a large amount of organic solvent is required. In contrast, in the case of a CSTR, it is possible to control the distribution of the concentrations of the cyclization precursor and cyclized product to be homogeneous in the reactor, and by adjusting the residence time and such, it is possible to keep the cyclization precursor at low concentrations in the reactor with a reduced amount of the solvent used. The present inventors focused on this point.

The present invention was achieved in view of the above circumstances. An objective of the present invention is to provide methods of producing a cyclic organic compound using a CSTR(s), which can achieve excellent impurity-suppressing effects (quality improvement, for example, inhibition of intermolecular cyclization reaction), size reduction of the reaction tank(s), continuous production, and such, compared to conventional cyclization methods.

Means for Solving the Problems

To solve the above-mentioned problems, the present inventors studied cyclization reactions using a continuous stirred tank reactor (CSTR), which had not been conventionally used in cyclization reactions for cyclic compounds, and thereby discovered that such methods can achieve excellent impurity-suppressing effects (quality improvement), size reduction of the reaction tank, continuous production, and such, compared to conventional cyclization methods, and thus completed the present invention.

Furthermore, the present inventors discovered that the above-mentioned improvement effects can efficiently be achieved also in the production of cyclic peptides or heterocyclic compounds by applying simulation methods that had been conventionally used mainly at the fine chemicals plant level to the cyclization reactions of the present invention, thereby experimentally predicting the reaction rate of a cyclization reaction, and setting the flow volume (residence time), the concentrations of precursor and cyclic organic compound, and the temperature for the cyclization reaction and such which affect these conditions, in the cyclization reaction using a CSTR(s).

The present invention is based on such findings, and specifically provides [1] to [15] below:

[1] a method of producing a cyclic organic compound, which comprises a cyclization reaction step of cyclizing a cyclization precursor of the cyclic organic compound in at least one continuous stirred tank reactor (CSTR);

[2] the method of [1], wherein the cyclic organic compound is a peptide compound comprising a cyclic portion, wherein the compound is composed of natural amino acids and/or amino acid analogs;

[3] the method of [1] or [2], wherein the peptide compound comprising the cyclic portion comprises a cyclic portion consisting of 4 to 14 natural amino acid and/or amino acid analog residues, and wherein the total number of natural amino acid and amino acid analog residues is 7 to 20;

[4] the method of [3], wherein the cyclic organic compound has the following features:
(i) comprising at least two N-substituted amino acids, and at least one non-N-substituted amino acid; and
(ii) having a C log P value of 6 or greater;

[5] the method of any one of [1] to [4], wherein the cyclization reaction is an intramolecular cyclization reaction through one or more bonds selected from the group consisting of the following:
(i) an amide bond;
(ii) a disulfide bond;
(iii) an ether bond;
(iv) a thioether bond;
(v) an ester bond;
(vi) a thioester bond; and
(vii) a carbon-carbon bond;

[6] the method of [1] or [2], wherein the cyclic organic compound is a compound represented by general formula (I) below:

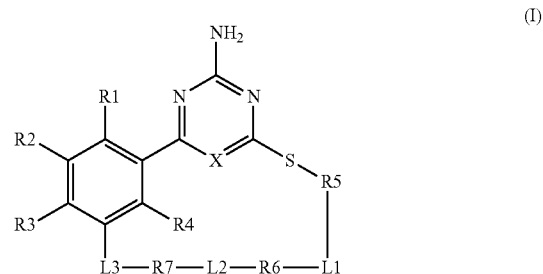

(wherein X represents CH or N; R1 represents a hydrogen atom, a halogen atom, a cyano group, a C1-6 alkyl group, a C1-4 haloalkyl group, a C2-6 alkenyl group, a C2-6 alkynyl group, a C1-6 alkoxy group, or a C1-6 alkylthio group; R2 represents a hydrogen atom, a halogen atom, a C1-6 alkyl group, a C2-6 alkenyl group, or a C2-6 alkynyl group, or R2 and R3 together form a ring; R3 represents a hydrogen atom, a halogen atom, a cyano group, a C1-6 alkyl group, a C2-6 alkenyl group, a C2-6 alkynyl group, or a C1-6 alkoxy group, or R2 and R3 together form a ring; R4 represents a hydrogen atom, a halogen atom, a C1-6 alkyl group, a C2-6 alkenyl group, or a C2-6 alkynyl group; R5, R6, and R7 each independently represents an optionally substituted C1-6 alkylene group, C2-6 alkenylene group, C2-6 alkynylene group, C3-10 cycloalkylene group, C3-10 cycloalkenylene group, C6-12 arylene group, or –3- to 12-membered monocyclic heterocyclic ring-; L1, L2, and L3 each independently represents a single bond, —CONR8-, —NR8CO—, —NR8-, —O—, —SO$_2$NR8-, —NR8SO$_2$—, —COO—, NR8CONR8'-, NR8COO—, or —OCONR8-; and R8 and R8' each independently represents a hydrogen atom or an optionally substituted C1-6 alkyl group);

[7] the method of any one of [1] to [6], wherein the cyclization reaction is performed at an industrial scale using a condition obtained based on a result from a preliminary test of the cyclization reaction;

[8] the method of [7], wherein the condition is obtained by steps comprising the following:
(i) obtaining data on concentration change over time at multiple temperatures for at least one selected from the group consisting of the cyclization precursor, the cyclic organic compound, one or more intermediates, and one or more byproducts, in the preliminary test;
(ii) determining a reaction rate constant $k_n$ by using the data on concentration change obtained in step (i) and a reaction rate equation relating to the cyclization reaction;

(iii) determining frequency factor $A_n$ and activation energy $E_n$ by using the temperatures used in step (i), the reaction rate constant $k_n$ determined in step (ii), and the following equation (II):

$$k_n = A_n \exp\left(\frac{-E_n}{RT}\right) \tag{II}$$

(iv) determining a reaction rate constant $k_n$ at a temperature for cyclization in a CSTR(s) by using the frequency factor $A_n$ and activation energy $E_n$ determined in step (iii), the above-mentioned equation (II), and the above-mentioned reaction rate equation; and (v) obtaining the aforementioned condition using the reaction rate constant $k_n$ determined in step (iv), the aforementioned reaction rate equation, and the following CSTR mass balance equation (III):

$$\tau = \frac{C_{0,n} - C_n}{-r_n} \tag{III}$$

(wherein $r_n$ represents the reaction rate, $\tau$ represents the residence time (space time), $C_0$ represents the supply concentration, and $C$ represents the concentration);

[9] the method of [8], wherein the elementary reactions of the cyclization reaction are presented by formula (IV) below:

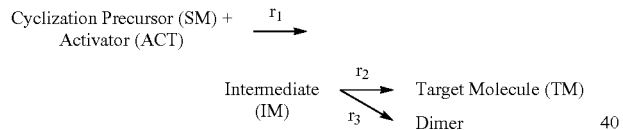

(IV)

and the reaction rate constants $k_1$, $k_2$, and $k_3$ are determined using any of equations (V) to (IX) below:

$$r_{SM} = \frac{dC_{SM}}{dt} = -k_1 C_{SM} C_{ACT} \tag{V}$$

$$r_{ACT} = \frac{dC_{ACT}}{dt} = -k_1 C_{SM} C_{ACT} \tag{VI}$$

$$r_{IM} = \frac{dC_{IM}}{dt} = k_1 C_{SM} C_{ACT} - k_2 C_{IM} - 2k_3 C_{IM}^2 \tag{VII}$$

$$r_{TM} = \frac{dC_{TM}}{dt} = k_2 C_{IM} \tag{VIII}$$

$$r_{Dimer} = \frac{dC_{Dimer}}{dt} = k_3 C_{IM}^2 \tag{IX}$$

(wherein TM represents the cyclic organic compound, SM represents the cyclization precursor, ACT represents the activator, IM represents the intermediate, Dimer represents the dimer, and C represents the concentration (M));

[10] the method of [8], wherein the elementary reactions of the cyclization reaction are presented by formula (X) below:

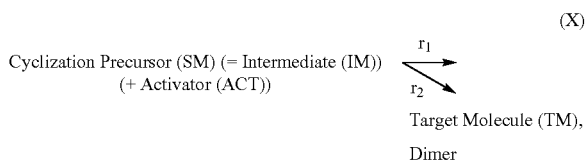

(X)

and the reaction rate constants $k_1$ and $k_2$ are determined using any of equations (XI) to (XIII) below:

$$r_{SM} = \frac{dC_{SM}}{dt} = \frac{dC_{ACT}}{dt} = -k_1 C_{SM} C_{ACT} - 2k_2 C_{SM}^2 C_{ACT}^2 \tag{XI}$$

$$r_{TM} = \frac{dC_{TM}}{dt} = k_1 C_{SM} C_{ACT} \tag{XII}$$

$$r_{Dimer} = \frac{dC_{Dimer}}{dt} = k_2 C_{SM}^2 C_{ACT}^2 \tag{XIII}$$

(wherein r represents the reaction rate, TM represents the target molecule, SM represents the cyclization precursor (=intermediate), ACT represents the activator, Dimer represents the dimer, and C represents the concentration (M));

[11] the method of any one of [7] to [10], wherein the condition is selected from the group consisting of flow volume in the continuous stirred tank reactor, concentration of the cyclization precursor, and concentration of the cyclic organic compound;

[12] a method of promoting intramolecular cyclization of a cyclization precursor, which comprises a step of cyclizing a cyclization precursor of a cyclic organic compound in at least one continuous stirred tank reactor (CSTR);

[13] a method of obtaining a condition for cyclizing a cyclization precursor of a cyclic organic compound at an industrial scale in at least one continuous stirred tank reactor (CSTR), which comprises the steps of:

(i) obtaining data on concentration change over time at multiple temperatures for at least one selected from the group consisting of the cyclization precursor, the cyclic organic compound, one or more intermediates, and one or more byproducts, in a preliminary test;

(ii) determining a reaction rate constant $k_n$ using the data on concentration change obtained in step (i) and a reaction rate equation relating to the cyclization reaction;

(iii) determining frequency factor $A_n$ and activation energy $E_n$ by using the temperatures used in step (i), the reaction rate constant $k_n$ determined in step (ii), and the following equation (II):

$$k_n = A_n \exp\left(\frac{-E_n}{RT}\right) \tag{II}$$

(iv) determining a reaction rate constant $k_n$ at a temperature for cyclization in the CSTR by using the frequency factor $A_n$ and activation energy $E_n$ determined in step (iii), the above-mentioned equation (II), and the above-mentioned reaction rate equation; and (v) obtaining the aforementioned condition using the reaction rate constant $k_n$ determined in step (iv), the aforementioned reaction rate equation, and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration);

[14] a program for making a computer execute steps (i) to (iv) below to obtain a condition for cyclizing a cyclization precursor of a cyclic organic compound at an industrial scale in at least one continuous stirred tank reactor (CSTR):
(i) determining a reaction rate constant $k_n$ by using:
data on concentration change over time at multiple temperatures for at least one selected from the group consisting of the cyclization precursor, the cyclic organic compound, one or more intermediates, and one or more byproducts, obtained in a preliminary test, and
a reaction rate equation relating to the cyclization reaction;
(ii) determining frequency factor $A_n$ and activation energy $E_n$ by using the temperatures used in step (i), the reaction rate constant $k_n$ determined in step (i), and the following equation (II):

$$k_n = A_n \exp\left(\frac{-E_n}{RT}\right) \quad \text{(II)}$$

(iii) determining a reaction rate constant $k_n$ at a temperature for cyclization in the CSTR by using the frequency factor $A_n$ and activation energy $E_n$ determined in step (ii), the above-mentioned equation (II), and the above-mentioned reaction rate equation; and
(iv) obtaining the aforementioned condition using the reaction rate constant $k_n$ determined in step (iii), the aforementioned reaction rate equation, and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration); and

[15] a system for obtaining a condition for cyclizing a cyclization precursor of a cyclic organic compound at an industrial scale in at least one continuous stirred tank reactor (CSTR), which comprises:
(i) a means of determining a reaction rate constant $k_n$ by using:
data on concentration change over time at multiple temperatures for at least one selected from the group consisting of the cyclization precursor, the cyclic organic compound, one or more intermediates, and one or more byproducts, obtained in a preliminary test, and
a reaction rate equation relating to the cyclization reaction;
(ii) a means of determining frequency factor $A_n$ and activation energy $E_n$ by using the temperatures used in step (i), the reaction rate constant $k_n$ determined in step (i), and the following equation (II):

$$k_n = A_n \exp\left(\frac{-E_n}{RT}\right) \quad \text{(II)}$$

(iii) a means of determining a reaction rate constant $k_n$ at a temperature for cyclization in the CSTR by using the frequency factor $A_n$ and activation energy $E_n$ determined in step (ii), the above-mentioned equation (II), and the above-mentioned reaction rate equation; and
(iv) a means of obtaining the aforementioned condition using the reaction rate constant $k_n$ determined in step (iii), the aforementioned reaction rate equation, and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration).

Furthermore, the following inventions are also provided:
[2-1] a method of suppressing intermolecular reaction of a cyclization precursor, which comprises a step of cyclizing a cyclization precursor of a cyclic organic compound in at least one continuous stirred tank reactor;
[2-2] use of a continuous stirred tank reactor for intramolecularly cyclizing a cyclization precursor of a cyclic organic compound in at least one continuous stirred tank reactor;
[2-3] the method of [7], wherein the condition is obtained by steps comprising the following:
(i) obtaining data on concentration change over time at a single temperature for at least one selected from the group consisting of the cyclization precursor, the cyclic organic compound, one or more intermediates, and one or more byproducts, in a preliminary test;
(ii) determining a reaction rate constant $k_n$ by using the data on concentration change obtained in step (i) and a reaction rate equation relating to the cyclization reaction; and
(iii) obtaining the aforementioned condition using the reaction rate constant $k_n$ determined in step (ii), the aforementioned reaction rate equation, and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration);

[2-4] a method of obtaining a condition for cyclizing a cyclization precursor of a cyclic organic compound at an industrial scale in at least one continuous stirred tank reactor (CSTR), which comprises the steps of:
  (i) obtaining data on concentration change over time at a single temperature for at least one selected from the group consisting of the cyclization precursor, the cyclic organic compound, one or more intermediates, and one or more byproducts, in a preliminary test;
  (ii) determining a reaction rate constant $k_n$ by using the data on concentration change obtained in step (i) and a reaction rate equation relating to the cyclization reaction; and
  (iii) obtaining the aforementioned condition using the reaction rate constant $k_n$ determined in step (ii), the aforementioned reaction rate equation, and the following CSTR mass balance equation (III):

$$\tau = \frac{C_{0,n} - C_n}{-r_n} \quad (III)$$

(wherein $r_n$ represents the reaction rate, $\tau$ represents the residence time (space time), $C_0$ represents the supply concentration, and C represents the concentration);

[2-5] a program for making a computer execute the following steps to obtain a condition for cyclizing a cyclization precursor of a cyclic organic compound at an industrial scale in at least one continuous stirred tank reactor (CSTR):
  (i) determining a reaction rate constant $k_n$ by using:
    data on concentration change over time at a single temperature for at least one selected from the group consisting of the cyclization precursor, the cyclic organic compound, one or more intermediates, and one or more byproducts, obtained in a preliminary test, and
    a reaction rate equation relating to the cyclization reaction; and
  (ii) obtaining the aforementioned condition using the reaction rate constant $k_n$ determined in step (i), the aforementioned reaction rate equation, and the following CSTR mass balance equation (III):

$$\tau = \frac{C_{0,n} - C_n}{-r_n} \quad (III)$$

(wherein $r_n$ represents the reaction rate, t represents the residence time (space time), C0 represents the supply concentration, and C represents the concentration); and

[2-6] a system for obtaining a condition for cyclizing a cyclization precursor of a cyclic organic compound at an industrial scale in at least one continuous stirred tank reactor, which comprises:
  (i) a means of determining a reaction rate constant $k_n$ by using:
    data on concentration change over time at a single temperature for at least one selected from the group consisting of the cyclization precursor, the cyclic organic compound, one or more intermediates, and one or more byproducts, obtained in a preliminary test, and
    a reaction rate equation relating to the cyclization reaction; and
  (ii) a means of obtaining the aforementioned condition using the reaction rate constant $k_n$ determined in step (i), the aforementioned reaction rate equation, and the following CSTR mass balance equation (III):

$$\tau = \frac{C_{0,n} - C_n}{-r_n} \quad (III)$$

wherein $r_n$ represents the reaction rate, $\tau$ represents the residence time (space time), C0 represents the supply concentration, and C represents the concentration).

Effects of the Invention

The present invention provides methods of producing cyclic organic compounds by performing cyclization reactions using a CSTR(s), which can achieve excellent impurity-suppressing effects, size reduction of the reaction tank, continuous production, and such, in comparison to conventional cyclization methods. Furthermore, the present invention provides production methods which can achieve the above-mentioned improvement effects more efficiently by applying simulation methods to determine conditions for the cyclization reactions.

MODE FOR CARRYING OUT THE INVENTION

Definition of Substituent Groups and Such

Figure 1:
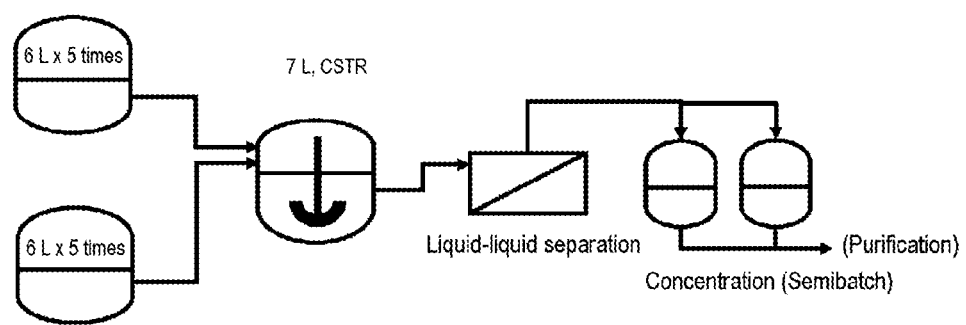
FIG. 1 presents assumed equipment for synthesizing 2 kg of the target molecule using a CSTR (the condition of Run 4 in Example 1).

Herein, the term "alkyl" refers to a monovalent group derived from aliphatic hydrocarbon by removal of one arbitrary hydrogen atom and has a subset of a hydrocarbyl or hydrocarbon group structure containing neither heteroatoms nor unsaturated carbon-carbon bonds in the backbone and containing hydrogen and carbon atoms. Its carbon chain length n is in the range of one to 20, and alkyl is preferably C2-C10 alkyl. Examples of alkyl include "C1-C6 alkyl" and specifically include methyl, ethyl, propyl, butyl, pentyl, hexyl, isopropyl, t-butyl group, sec-butyl group, 1-methylpropyl group, 1,1-dimethylpropyl group, 2,2-dimethylpropyl, 1,2-dimethylpropyl, 1,1,2-trimethylpropyl, 1,2,2-trimethylpropyl, 1,1,2,2-tetramethylpropyl, 1-methylbutyl, 2-methylbutyl, 3-methylbutyl, 1,1-dimethylbutyl, 1,2-dimethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, isopentyl, and neopentyl.

Herein, the term "alkenyl" refers to a monovalent group having at least one double bond (two adjacent SP2 carbon atoms). The double bond can assume entgegen (E) or zusammen (Z) and cis or trans geometric forms depending on the arrangement of the double bond and substituents (if they exist). Examples of alkenyl include linear or branched chains, including straight chains containing internal olefins. Preferred examples thereof include C2-C10 alkenyl, and more preferably C2-C6 alkenyl.

Specific examples of alkenyl include vinyl, allyl, 1-propenyl, 2-propenyl, 1-butenyl, 2-butenyl (including cis and trans forms), 3-butenyl, pentenyl, and hexenyl.

Herein, the term "alkynyl" refers to a monovalent group having at least one triple bond (two adjacent SP carbon atoms). Examples thereof include linear or branched chain alkynyl including internal alkylene. Preferred examples thereof include C2-C10 alkynyl, and more preferably C2-C6 alkynyl.

Specific examples of alkynyl include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

Herein, the term "cycloalkyl" means a saturated or partially saturated cyclic monovalent aliphatic hydrocarbon group containing a single ring, bicyclo ring, or spiro ring. Preferred examples thereof include C3-C10 cycloalkyl. Specific examples of cycloalkyl include cyclopropyl, cyclobutyl, cyclopentyl, cyclohexyl, cycloheptyl, cyclooctyl, and bicyclo[2.2.1]heptyl.

Herein, the term "aryl" means a monovalent aromatic hydrocarbon ring. Preferred examples thereof include C6-C10 aryl. Specific examples of aryl include phenyl and naphthyl (e.g., 1-naphthyl and 2-naphthyl).

Herein, the term "heteroaryl" means an aromatic cyclic monovalent group containing preferably one to five heteroatoms among ring-constituting atoms and may be partially saturated. The ring may be a single ring or bicyclic condensed ring (e.g., bicyclic heteroaryl formed by condensation with benzene or a monocyclic heteroaryl). The number of ring-constituting atoms is preferably five to ten (five- to ten-membered heteroaryl).

Specific examples of heteroaryl include furyl, thienyl, pyrrolyl, imidazolyl, pyrazolyl, thiazolyl, isothiazolyl, oxazolyl, isooxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

Herein, the term "arylalkyl (aralkyl)" means a group containing both an aryl and an alkyl, for example, a group derived from the above-mentioned alkyl by replacement of at least one hydrogen atom with an aryl. Preferred examples thereof include "C5-C10 aryl-C1-C6 alkyl", such as benzyl.

Herein, the term "arylene" means a divalent group derived from the above-mentioned aryl by removing another single arbitrary hydrogen atom. An arylene may be a single ring or a condensed ring. The number of ring-constituting atoms is not particularly limited, but is preferably six to ten (C6-10 arylene). Specific examples of arylene include phenylene and naphthylene.

Herein, the term "heteroarylene" means a divalent group derived from the above-mentioned heteroaryl by removing another single arbitrary hydrogen atom. A heteroarylene may be a single ring or a condensed ring. The number of ring-constituting atoms is not particularly limited but is preferably five to ten (five- to ten-membered heteroarylene). Specific examples of heteroarylene include pyroldiyl, imidazoldiyl, pyrazoldiyl, pyridindiyl, pyridazindiyl, pyrimidindiyl, pyrazindiyl, triazoldiyl, triazindiyl, isooxazoldiyl, oxazoldiyl, oxadiazoldiyl, isothiazoldiyl, thiazoldiyl, thiadiazoldiyl, furandiyl, and thiophendiyl.

In the present invention, "amino acids" constituting the peptides may be "natural amino acids" or "amino acid analogs". The "amino acids", "natural amino acids", and "amino acid analogs" are also referred to as "amino acid residues", "natural amino acid residues", and "amino acid analog residues", respectively.

"Natural amino acids" are α-aminocarboxylic acids (α-amino acids), and refer to the 20 types of amino acids contained in proteins. Specifically, they refer to Gly, Ala, Ser, Thr, Val, Leu, Ile, Phe, Tyr, Trp, His, Glu, Asp, Gln, Asn, Cys, Met, Lys, Arg and Pro.

"Amino acid analogs" are not particularly limited, and include β-amino acids, γ-amino acids, D-amino acids, N-substituted amino acids, α,α-disubstituted amino acids, hydroxycarboxylic acids, unnatural amino acids (amino acids of which side chains are different from those of natural amino acids; for example, unnatural α-amino acids, β-amino acids, and γ-amino acids). An α-amino acid may be a D-amino acid, or an α,α-dialkylamino acid. In a similar manner to an α-amino acid, a β-amino acid and a γ-amino acid are also allowed to have any configuration. A side chain (with the main chain being methylene) of the amino acid analogs is not particularly limited, and may have, besides hydrogen atoms, for example, an alkyl, an alkenyl, an alkynyl, an aryl, a heteroaryl, an aralkyl, or a cycloalkyl. Each of these may have one or more substituents, and these substituents can be selected from any functional group containing, for example, a halogen atom, an N atom, an O atom, an S atom, a B atom, a Si atom, or a P atom. For example, herein, "C1-C6 alkyl optionally substituted with halogen" means "C1-C6 alkyl" substituted with one or more halogen atoms, and specific examples include trifluoromethyl, difluoromethyl, fluoromethyl, pentafluoroethyl, tetrafluoroethyl, trifluoroethyl, difluoroethyl, fluoroethyl, trichloromethyl, dichloromethyl, chloromethyl, pentachloroethyl, tetrachloroethyl, trichloroethyl, dichloroethyl, and chloroethyl. Furthermore, for example, "optionally substituted C5-C10 aryl C1-C6 alkyl" means that in which at least one hydrogen atom of the aryl and/or alkyl of "C5-C10 aryl C1-C6 alkyl" has been substituted with a substituent. Furthermore, "cases having two or more substituents" include cases having an S atom-containing functional group, which further has functional groups such as an amino or a halogen. For example, an example of side chain of amino acid analogs includes a side chain having a polyethylene glycol structure.

The main chain amino group of an amino acid analog may be unsubstituted (a NH2 group), or it may be substituted (that is, an NHR group; in which R represents an alkyl, an alkenyl, an alkynyl, an aryl, a heteroaryl, an aralkyl, or a cycloalkyl, each of which optionally has a substituent; or a carbon chain bonded to the N atom and a carbon atom at the α position may form a ring as in proline. The substituent is similar to the substituent of the side chain, and examples include a halogen, an oxy, and a hydroxy.). Furthermore, for "an alkyl, an alkenyl, an alkynyl, an aryl, a heteroaryl, an aralkyl, or a cycloalkyl" in the definition of these substituents, the above-mentioned definitions for these functional groups are applied. For example, herein, "alkoxy" means a group in which a hydrogen atom in a hydroxy group is replaced with the above-mentioned alkyl group. Preferred examples thereof include "C1-C6 alkoxy".

Examples of halogen-derived substituents include fluoro (—F), chloro (—Cl), bromo (—Br), and iodo (—I).

Examples of O atom-derived substituents include hydroxyl (—OH), oxy (—OR), carbonyl (—C=O—R), carboxyl (—CO2H), oxycarbonyl (—C=O—OR), carbonyloxy (—O—C=O—R), thiocarbonyl (—C=O—SR), carbonylthio group (—S—C=O—R), aminocarbonyl (—C=O—NHR), carbonylamino (—NH—C=O—R), oxycarbonylamino (—NH—C=O—OR), sulfonylamino (—NH—SO2-R), aminosulfonyl (—SO2-NHR), sulfamoylamino (—NH—SO2-NHR), thiocarboxyl (—C(=O)—SH), and carboxylcarbonyl (—C(=O)—CO2H).

Examples of oxy (—OR) include alkoxy, cycloalkoxy, alkenyloxy, alkynyloxy, aryloxy, heteroaryloxy, and aralkyloxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include, alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl, cycloalkylaminocarbonyl, alkenylaminocarbonyl, alkynylaminocarbonyl, arylaminocarbonyl, heteroarylaminocarbonyl, and aralkylaminocarbonyl. Additional examples include compounds produced by further substitution of an alkyl, a cycloalkyl, an alkenyl, an alkynyl, an aryl, a heteroaryl, or an aralkyl for the H atom bonded to the N atom in —C=O—NHR.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—R.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—OR.

Examples of sulfonylamino (—NH—SO2-R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds produced by further substitution of an alkyl, a cycloalkyl, an alkenyl, an alkynyl, an aryl, a heteroaryl, or an aralkyl for the H atom bonded to the N atom in —NH—SO2-R.

Examples of aminosulfonyl (—SO2-NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds produced by further substitution of an alkyl, a cycloalkyl, an alkenyl, an alkynyl, an aryl, a heteroaryl, or an aralkyl for the H atom bonded to the N atom in —SO2-NHR.

Examples of sulfamoylamino (—NH—SO2-NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. Additionally, the two H atoms bonded to the N atoms in —NH—SO2-NHR may be substituted with a substituent independently selected from the group consisting of an alkyl, a cycloalkyl, an alkenyl, an alkynyl, an aryl, a heteroaryl, and an aralkyl; or these two substituents may form a ring.

For S atom-derived substituents, examples include thiol (—SH), thio (—S—R), sulfinyl (—S=O—R), sulfonyl (—S(O)2-R), and sulfo (—SO3H).

Examples of thio (—S—R) are selected from among alkylthio, cycloalkylthio, alkenylthio, alkynylthio, arylthiol, heteroarylthio, aralkylthio, and such.

Examples of sulfinyl (—S=O—R) include alkylfulfinyl, cycloalkylsulfinyl, alkenylsulfinyl, alkynylsulfinyl, arylsulfinyl, heteroarylsulfinyl, and aralkylsulfinyl.

Examples of sulfonyl (—S(O)2-R) include alkylsulfonyl, cycloalkylsulfonyl, alkenylsulfonyl, alkynylsulfonyl, arylsulfonyl, heteroarylsulfonyl, and aralkylsulfonyl.

For N atom-derived substituents, examples include azide (—N3, also called "azido group"), cyano (—CN), primary amino (—NH2), secondary amino (—NH—R), tertiary amino (—NR(R')), amidino (—C(=NH)—NH2), substituted amidino (—C(=NR)—NR'R"), guanidino (—NH—C(=NH)—NH2), substituted guanidino (—NR—C(=NR''')—NR'R"), and aminocarbonylamino (—NR—CO—NR'R").

Examples of secondary amino (—NH—R) include alkylamino, cycloalkylamino, alkenylamino, alkynylamino, arylamino, heteroarylamino, and aralkylamino.

Examples of tertiary amino (—NR(R')) include amino groups, such as alkyl(aralkyl)amino, having any two substituents each independently selected from alkyl, cycloalkyl, alkenyl, alkynyl, aryl, heteroaryl, and aralkyl; and these two arbitrary substituents may form a ring.

Examples of substituted amidino (—C(=NR)—NR'R") include groups in which each of the three substituents R, R', and R" on the N atoms is independently selected from among alkyl, cycloalkyl, alkenyl, alkynyl, aryl, heteroaryl, and aralkyl; and such examples include alkyl(aralkyl)(aryl) amidino.

Examples of substituted guanidino (—NR—C(=NR''')—NR'R") include groups in which each of R, R', R", and R''' is independently selected from alkyl, cycloalkyl, alkenyl, alkynyl, aryl, heteroaryl, and aralkyl; or groups in which they form a ring.

Examples of aminocarbonylamino (—NR—CO—NR'R") include groups in which each of R, R', and R" is independently selected from a hydrogen atom, alkyl, cycloalkyl, alkenyl, alkynyl, aryl, heteroaryl, and aralkyl; or groups in which they form a ring.

Examples of B atom-derived substituents include boryl (—BR(R')) and dioxyboryl (—B(OR)(OR')). These two substituents, R and R', are each independently selected from alkyl, cycloalkyl, alkenyl, alkynyl, aryl, heteroaryl, and aralkyl; or they may form a ring.

In the present invention, at least one atom constituting an "amino acid" may be an atom (isotope) of the same atomic number (number of protons) and different mass number (total number of protons and neutrons). Examples of the isotope contained in the "amino acid" include a hydrogen atom, a carbon atom, a nitrogen atom, an oxygen atom, a phosphorus atom, a sulfur atom, a fluorine atom, and a chlorine atom, including 2H, 3H, 13C, 14C, 15N, 17O, 18O, 31P, 32P, 35S, 18F and 36Cl.

Exemplary amino acid analogs that can be used in the present invention are shown below; however, the amino acid analogs are not limited thereto. Many of these amino acid analogs can be purchased with their side chains protected or unprotected and their amine moieties protected or unprotected. Those that cannot be purchased can be synthesized by known methods.

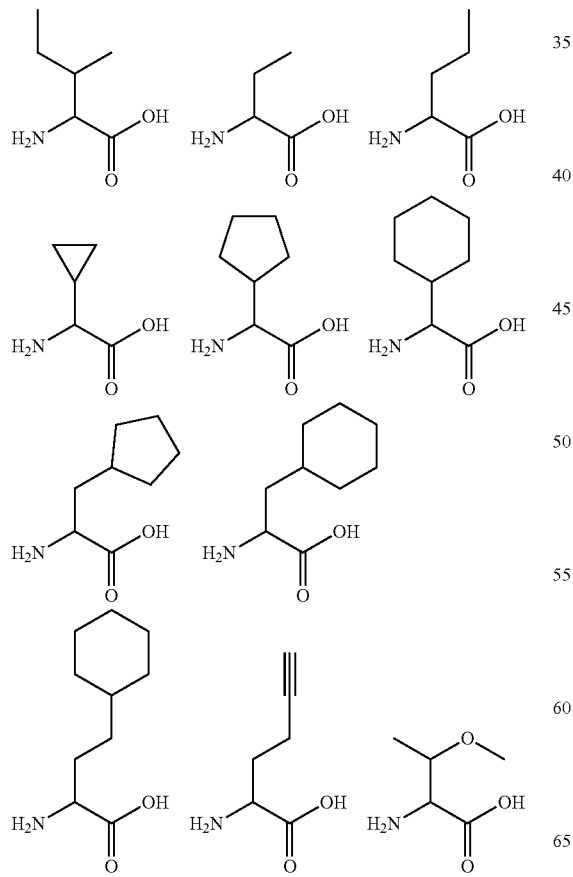

-continued

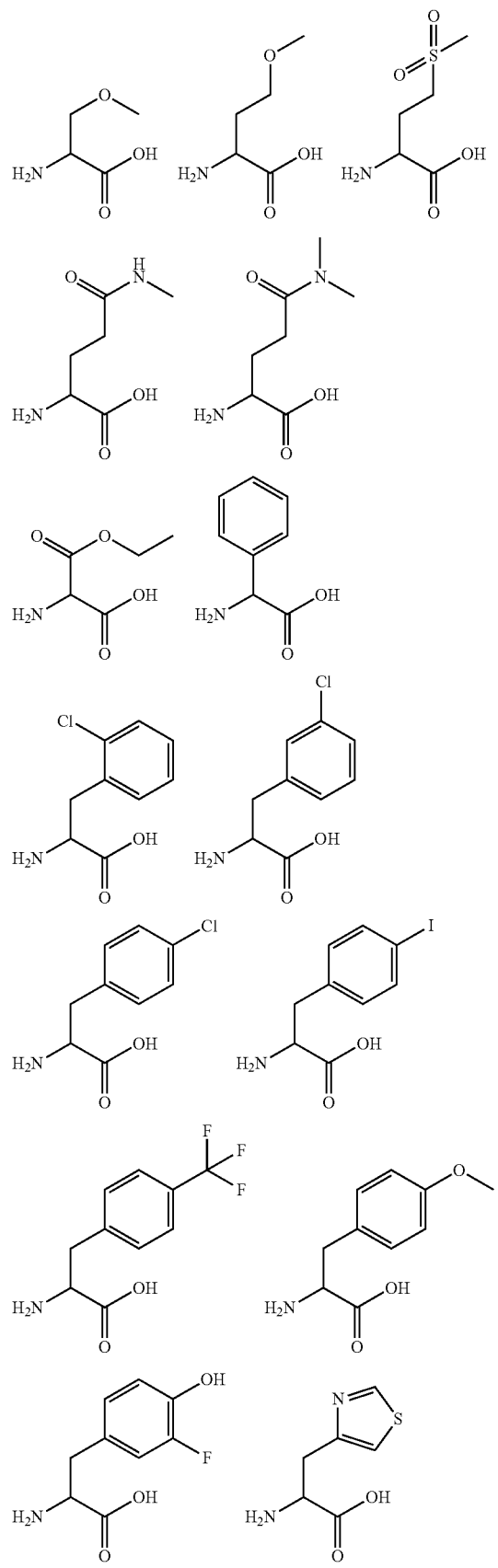

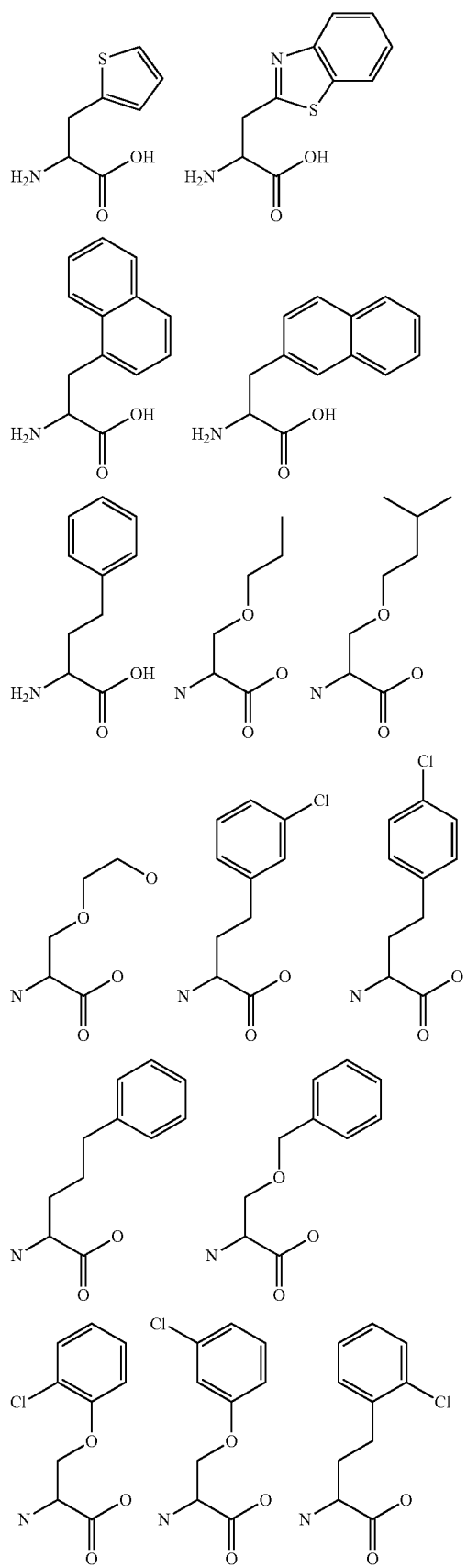
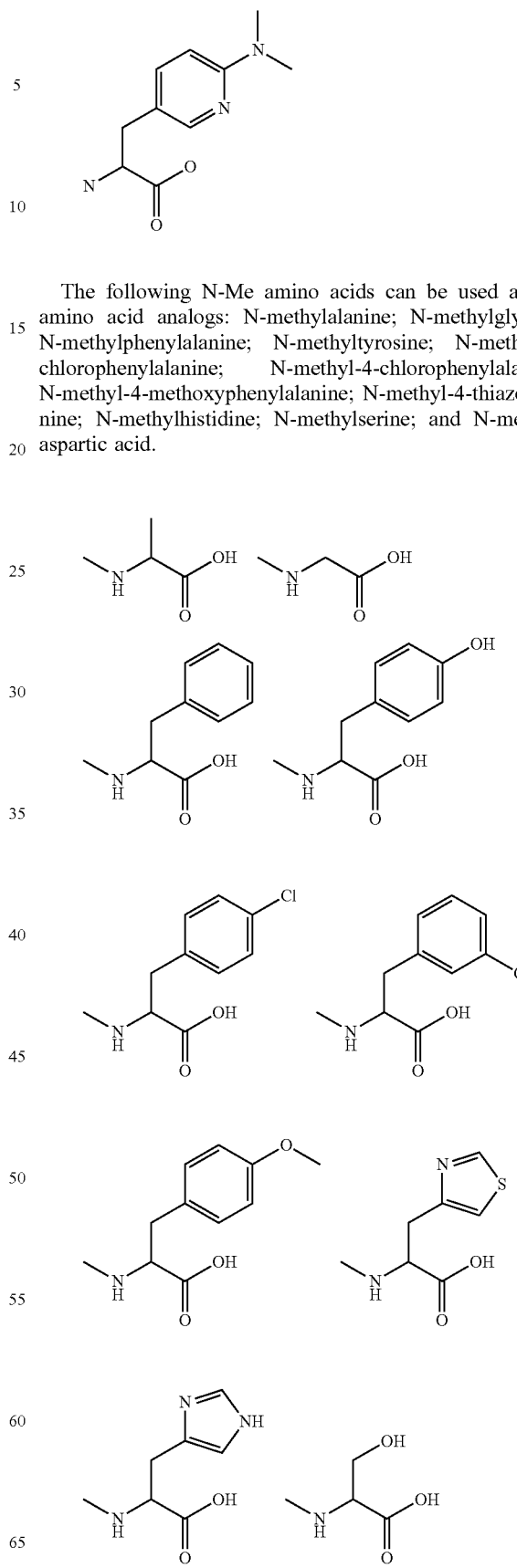
The following N-Me amino acids can be used as the amino acid analogs: N-methylalanine; N-methylglycine; N-methylphenylalanine; N-methyltyrosine; N-methyl-3-chlorophenylalanine; N-methyl-4-chlorophenylalanine; N-methyl-4-methoxyphenylalanine; N-methyl-4-thiazolalanine; N-methylhistidine; N-methylserine; and N-methylaspartic acid.

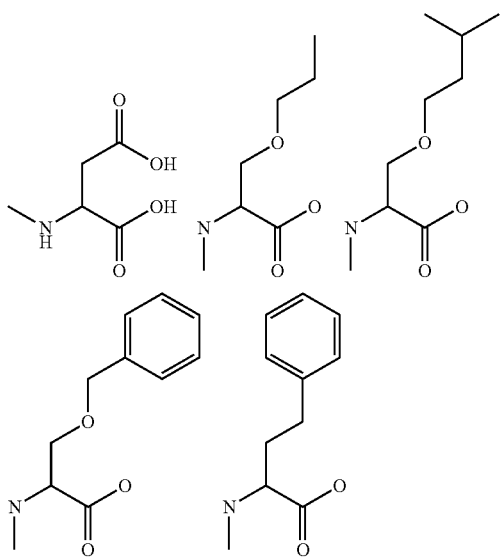

The following N-alkylamino acids may also be used as the amino acid analogs.

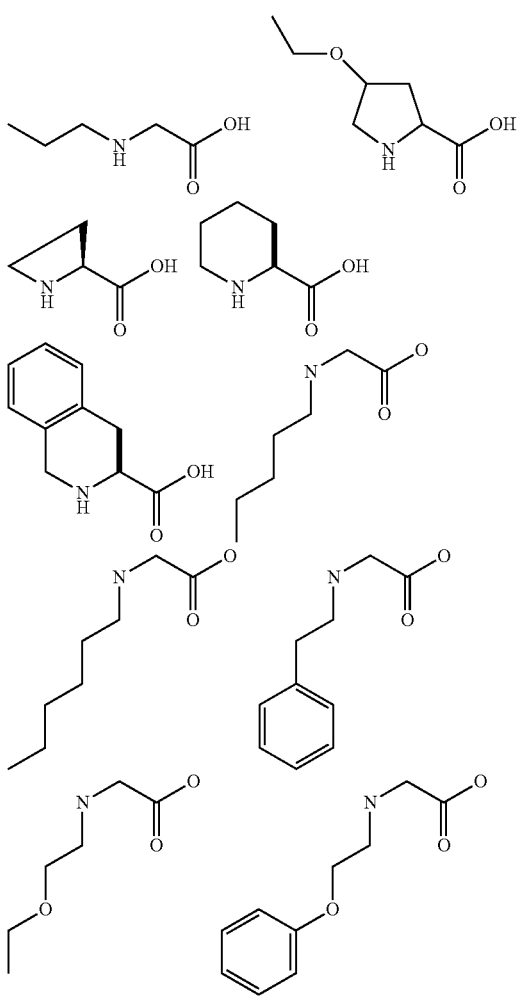

The following D-amino acid can also be used as the amino acid analog.

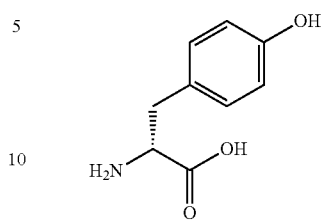

The following α,α-dialkylamino acid can also be used as the amino acid analog.

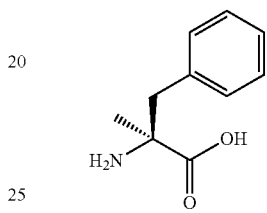

The following amino acid may also be used as the amino acid analog.

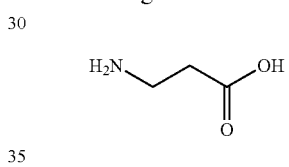

In a non-limiting embodiment, the present invention provides methods of producing a cyclic organic compound, which comprise a cyclization reaction step which cyclizes a cyclization precursor of the cyclic organic compound in at least one continuous stirred tank reactor.

Furthermore, in a non-limiting embodiment, the present invention provides methods of promoting intramolecular cyclization of a cyclization precursor, which comprise a step of cyclizing a cyclization precursor of a cyclic organic compound in at least one or more continuous stirred tank reactors.

In addition, in a non-limiting embodiment, the present invention provides methods of suppressing intermolecular reaction of a cyclization precursor, which comprise a step of cyclizing a cyclization precursor of a cyclic organic compound in at least one or more continuous stirred tank reactors.

Furthermore, in a non-limiting embodiment, the present invention provides uses of a continuous stirred tank reactor (s) for intramolecularly cyclizing a cyclization precursor of a cyclic organic compound in at least one or more continuous stirred tank reactors.

The term "cyclic organic compound" in the present invention means an organic compound having a cyclic portion(s). The "cyclic organic compound" in the present invention is not particularly limited as long as it has that feature, but may include, for example, middle-molecular-weight compounds (for example, having a molecular weight of approximately 500 to 6000) including natural products, sugar chains, peptides, and nucleic acid pharmaceuticals, and low-molecular-weight compounds (for example, having a molecular weight of approximately 500). Preferred examples include peptide compounds having a cyclic portion(s).

For example, whether a desired cyclic organic compound has been produced or not can be evaluated by measuring the molecular weight of the compound produced by the methods of the present invention using MS, SDS-PAGE, and such, which are techniques known to those skilled in the art.

The term "cyclization precursor" of the present invention means, with respect to a cyclic organic compound of the present invention produced by undergoing a cyclization step, a non-cyclic organic compound (precursor) before undergoing the cyclization step. Preferably, without limitation, the cyclization precursor has the same chemical structure as the cyclic organic compound except for the structural portion involved in the cyclization reaction. The structural portion involved in the cyclization reaction includes a structure like a reaction auxiliary group for the cyclization reaction, which can be eliminated after the bonding reaction.

For example, when the cyclization precursor is a low-molecular-weight organic compound, the cyclization precursor can be produced by using organic synthesis methods which are known techniques to those skilled in the art. On the other hand, when the cyclization precursor is a peptide compound, it can be obtained by, in addition to the above-mentioned organic synthesis methods, peptide synthesis using cell-free translation systems or expression of a gene encoding the peptide compound in appropriate host cells.

In a non-limiting embodiment, the cyclization reaction in the present invention is an intramolecular cyclization reaction by one or more bonds selected from the group consisting of:
  (i) an amide bond;
  (ii) a disulfide bond;
  (iii) an ether bond;
  (iv) a thioether bond;
  (v) an ester bond;
  (vi) a thioester bond; and
  (vii) a carbon-carbon bond.

For example, the intramolecular cyclization in the above-mentioned embodiment may take place by bonding of two amino acids by a disulfide bond, amide bond, peptide bond, alkyl bond, alkenyl bond, ester bond, thioester bond, ether bond, thioether bond, phosphonate ether bond, azo bond, C=N—C bond, amide bond, lactam bridge, carbamoyl bond, urea bond, thiourea bond, amine bond, thioamide bond, sulfinyl bond, sulfonyl bond, or such, but the type of bond used for the intramolecular cyclization reaction is not limited thereto.

The intramolecular cyclization in the above-mentioned embodiment is, without limitation, preferably carried out by covalent bonding such as amide bonding, carbon-carbon bond-forming reaction, S—S bonding, thioether bonding, triazole bonding, or benzoxazole bonding (WO 2013/100132; WO 2012/026566; WO 2012/033154; WO 2012/074130; WO 2015/030014; WO 2018/052002; Comb Chem High Throughput Screen. 2010; 13: 75-87; Nature Chem. Bio. 2009, 5, 502; Nat Chem Biol. 2009, 5, 888-90; Bioconjugate Chem., 2007, 18, 469-476; Chem Bio Chem, 2009, 10, 787-798; Chemical Communications (Cambridge, United Kingdom) (2011), 47(36), 9946-9958).

Compounds that can be obtained by further chemical modification of the above-mentioned compounds may also be included in the cyclic organic compounds and the peptide compounds having a cyclic portion(s) of the present invention.

The peptide compounds of the present invention may have a linear portion(s). The number of amide bonds and ester bonds (number/length of natural amino acids or amino acid analogs) is not particularly limited, but when the compound has a linear portion(s), the total number of residues of the cyclic portion and the linear portion(s) is preferably 30 or less. To attain high metabolic stability, the total number of amino acids is more preferably six or more, or nine or more. Furthermore, in addition to the description above, the number of natural amino acids and amino acid analogs constituting the cyclic portion is more preferably 4 to 14, 4 to 13, 5 to 13, 5 to 12, 6 to 12, or 7 to 12, and even more preferably 7 to 11, or 8 to 11. Nine to 11 residues (10 or 11 residues) is particularly preferred. The number of amino acids and amino acid analogs of the linear portion is preferably 0 to 8, 0 to 7, 0 to 6, 0 to 5, or 0 to 4, and is more preferably 0 to 3. The total number of natural amino acid and amino acid analog residues is preferably 6 to 30, 6 to 25, 6 to 20, 7 to 20, 7 to 19, 7 to 18, 7 to 17, 7 to 16, 7 to 15, 8 to 14, or 9 to 13. In the present application, the amino acids include natural amino acids and amino acid analogs, unless particularly limited.

Furthermore, here, membrane permeability and metabolic stability herein mean that a peptide compound has sufficient membrane permeability and metabolic stability to be used as a pharmaceutical at least when it is used as an oral agent or for targeting an intracellular protein, nucleic acid, intracellular region of a membrane protein, or transmembrane domain of a membrane protein.

The cyclic portions of the cyclic portion-containing peptide compounds of the present invention are not particularly limited as long as they are in the form of a ring, but for example, they are preferably cyclic portions comprising a cyclized portion formed by functional groups that can satisfy both membrane permeability and metabolic stability.

In cyclization reactions with structurally nearby reactive sites, such as the five-membered ring construction reaction of indole and the oxirane ring construction reaction of epoxide, the intramolecular and intermolecular cyclization reactions are less likely to compete with each other (the intramolecular cyclization reaction proceeds predominantly). Therefore, when such cyclization reactions are used in the present invention, the present invention does not seem very advantageous.

Herein, "number of amino acids" refers to the number of amino acid residues (amino acid units) constituting a peptide, and it means the number of amino acid units that occur when the amide bonds, ester bonds, and the bonds of the cyclized portion linking amino acids are cleaved.

The term "tank reactor" of the present invention refers to a reactor equipped with a stirrer in which reaction fluid inside is sufficiently mixed so that the concentration and temperature can be regarded as uniform at any points in the reactor. When the tank reactor is operated batch-wise, it is called a "batch reactor", and when it is continuously operated, it is called a "continuous stirred tank reactor" (CSTR) (see "Kagaku Kogaku Binran (Chemical Engineering Handbook), Sixth Revised Edition, Maruzen Co., Ltd., 3.5 Basics of Reactor Design). To maximize productivity, product's properties, and efficiency of general processes, a single CSTR, multiple CSTRs in parallel, and serial CSTRs in which multiple CSTRs are connected serially are used. Raw reaction materials fed into the CSTR are immediately mixed for the reaction to proceed, and poured out of the reactor while remaining at the same concentration and temperature as inside the reactor.

In a non-limiting embodiment, the continuous stirred tank reactors used in the present invention can be used not only for homogeneous liquid phase reactions, but also for heterogeneous reactions such as liquid-liquid reactions, gas-liquid reactions, and gas-liquid-solid catalytic reactions. Furthermore, depending on the type of cyclization reaction of interest and the scale of production, those skilled in the art can appropriately select the optimum reactor size.

In a non-limiting embodiment, in the methods of the present invention for producing a cyclic organic compound using a CSTR(s), the CSTR may be run with a reaction tank that has been brought to a steady state in advance by separately performed in a flow reactor or batch reactor until the steady state is reached inside the reactor, or by the reverse dropwise addition method or high-dilution condition methods in a batch reactor. In this way, the possibility that raw reaction materials that remain unreacted are discharged outside of the reactors can be prevented as much as possible, and all substrates can be used effectively.

In a non-limiting embodiment, methods of producing a cyclic organic compound using a CSTR(s) are provided in which the cyclic organic compound in the present invention is a peptide compound comprising a cyclic portion which is composed of natural amino acids and/or amino acid analogs. Without limitation, the compound preferably comprises a cyclic portion consisting of 4 to 14 natural amino acid and amino acid analog residues in total, and has a total of 7 to 20 natural amino acid and amino acid analog residues. Furthermore, the cyclic portion preferably consists of 5 to 12, 6 to 12, 7 to 12, 8 to 12, or 9 to 12 natural amino acid and amino acid analog residues in total, and the total number of natural amino acid and amino acid analog residues is preferably 8 to 14, 9 to 13, 10 to 13, or 11 to 13. The total number of amino acids included in a peptide compound is preferably 25 or less, 20 or less, 18 or less, 17 or less, 16 or less, 15 or less, or 14 or less, and more preferably 13 or less (for example, 12, 11, 10, or 9), but is not particularly limited thereto.

In a non-limiting embodiment, a cyclic organic compound in the present invention has the following features:
  (i) comprising at least two N-substituted amino acids, and at least one non-N-substituted amino acid; and
  (ii) having a C log P value of 6 or greater.

In the above-mentioned embodiment, the cyclic organic compound of the present invention preferably comprises at least two (preferably 2, 3, 4, 5, 6, 7, 8, 9, or 10, and particularly preferably 5, 6, or 7) N-substituted amino acids, and preferably comprises at least one, two, three, or four non-N-substituted amino acids. Furthermore, the C log P value is preferably 7 or greater, 8 or greater, or 9 or greater. "N-substitution" includes substitution of a hydrogen atom bonded to the N atom with a methyl group, an ethyl group, a propyl group, a butyl group, a hexyl group, or such but is not limited thereto. Preferred N-substituted amino acids include natural amino acids in which the amino group is N-methylated. In the case where the peptide contains a chemically-modified amino acid analog(s), the compound, when regarded as having a molecular form (main chain structure) in which all chemical modifications have been completed, has a C log P value (computer-calculated partition coefficient; for example, it can be calculated using Daylight Version 4.9 of Daylight Chemical Information Systems, Inc.) of preferably 3 or greater, 4 or greater, 5 or greater, 6 or greater, 7 or greater, or 8 or greater, and preferably 20 or less, 19 or less, 18 or less, 17 or less, 16 or less, or 15 or less, in terms of its formed molecule.

The compounds targeted by the cyclization reactions using CSTR(s) in the present invention are not particularly limited, but their molecular weights are preferably 100 or greater, 200 or greater, 300 or greater, 400 or greater, 500 or greater, 550 or greater, 600 or greater, 650 or greater, 700 or greater, 750 or greater, 800 or greater, 850 or greater, 900 or greater, or 950 or greater, and preferably 1000 or greater, 1100 or greater, 1200 or greater, 1300 or greater, 1400 or greater, 1500 or greater, 1600 or greater, 1700 or greater, or 1800 or greater. The upper limit of the molecular weight is not particularly limited, but the molecular weight is preferably 6000 or less, 5000 or less, 4000 or less, 3000 or less, 2500 or less, or 2000 or less.

For example, when the intrinsic hepatic clearance (CLh int (μL/min/mg protein)) value when stability in the liver microsome is measured according to the above-described method is 150 or less, or preferably 100 or less, 90 or less, 80 or less, 70 or less, or 60 or less, or particularly preferably 50 or less, 40 or less, or 30 or less, it can be determined that metabolic stability allowing for the use as oral pharmaceuticals can be obtained. In the case of drugs metabolized by CYP3A4, to avoid its metabolism in the small intestine of humans, the intrinsic hepatic clearance value is preferably 78 or less (NPL: M. Kato et al., The intestinal first-pass metabolism of substances of CYP3A4 and P-glycoprotein-quantitative analysis based on information from the literature. Drug Metab. Pharmacokinet. 2003, 18(6), 365-372), and to exhibit bioavailability of approximately 30% or higher in humans, the value is preferably 35 or less (assuming that FaFg is 1 and protein binding rate is 0%).

Furthermore, the cyclic organic compounds in the present invention may be water-insoluble compounds. For example, a "water-insoluble compound" means a compound having solubility in ion-exchanged water at 20° C. of preferably 10 mg/mL or lower, or 1 mg/mL or lower, or more preferably 0.1 mg/mL or lower, 0.01 mg/mL or lower, or 0.001 mg/mL or lower.

In a non-limiting embodiment, the cyclization precursors of the present invention can carry a reaction auxiliary group(s) for cyclization reaction. In the present invention, the "reaction auxiliary group" refers to a group that is introduced into the vicinity of a functional group that is to be bonded and activates the functional group for binding reaction in order to let the reaction occur selectively at the desired position. For example, for a reaction between a carbonyl group and an amino group, a reaction auxiliary group can be introduced into either the carbonyl group side or the amino group side, or both. Examples of such reaction auxiliary groups include SH. Such reaction auxiliary groups can be eliminated along with or after the binding reaction.

In a non-limiting embodiment, the cyclic organic compounds of the present invention are compounds represented by the following general formula (I):

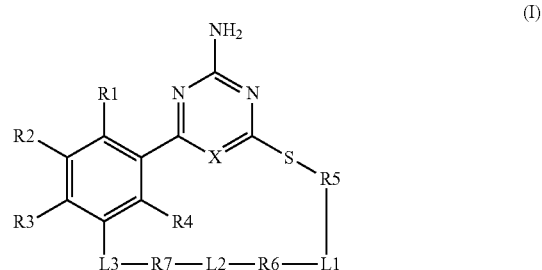

(wherein X represents CH or N; R1 represents a hydrogen atom, a halogen atom, a cyano group, a C1-6 alkyl group, a C1-4 haloalkyl group, a C2-6 alkenyl group, a C2-6 alkynyl group, a C1-6 alkoxy group, or a C1-6 alkylthio group; R2 represents a hydrogen atom, a halogen atom, a C1-6 alkyl group, a C2-6 alkenyl group, or a C2-6 alkynyl group, or R2 and R3 together form a ring; R3 represents a hydrogen atom, a halogen atom, a cyano group, a C1-6 alkyl group, a C2-6 alkenyl group, a C2-6 alkynyl group, or a C1-6 alkoxy group, or R2 and R3 together form a ring; R4 represents a hydrogen atom, a halogen atom, a C1-6 alkyl group, a C2-6 alkenyl group, or a C2-6 alkynyl group; R5, R6, and R7 each independently represent an optionally substituted C1-6 alkylene group, C2-6 alkenylene group, C2-6 alkynylene group, C3-10 cycloalkylene group, C3-10 cycloalkenylene group, C6-12 arylene group, or –3- to 12-membered monocyclic heterocyclic ring-; L1, L2, and L3 each independently represent a single bond, —CONR8-, —NR8CO—, —NR8-, —O—, —SO$_2$NR8-, —NR8SO$_2$—, —COO—, NR8CONR8'-, NR8COO—, or —OCONR8-; and R8 and R8' each independently represent a hydrogen atom or a C1-6 alkyl group which may have a substituent);

The terms used only for compounds represented by the above-mentioned general formula (I) are defined in the following paragraphs.

The term "C1-6 alkyl group" means a linear or branched-chain saturated monovalent C1-6 hydrocarbon group and includes, for example, a methyl group, an ethyl group, a propyl group, a butyl group, a pentyl group, a hexyl group, an isopropyl group, a sec-butyl group, a tert-butyl group, a 1-methylpropyl group, a 1,1-dimethylpropyl group, a 2,2-dimethylpropyl group, a 1,2-dimethylpropyl group, a 1,1,2-trimethylpropyl group, a 1,2,2-trimethylpropyl group, a 1,1,2,2-tetramethylpropyl group, a 1-methylbutyl group, a 2-methylbutyl group, a 3-methylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, an isopentyl group, and a neopentyl group.

The term "C1-3 alkyl group" means a linear or branched-chain saturated monovalent C1-3 hydrocarbon group and includes, for example, a methyl group, an ethyl group, a propyl group, and an isopropyl group.

The term "C1-4 alkyl group" means a linear or branched-chain saturated monovalent C1-4 hydrocarbon group and includes, for example, a methyl group, an ethyl group, a propyl group, a butyl group, an isopropyl group, a sec-butyl group, and a tert-butyl group.

The term "C1-4 haloalkyl group" means a "C1-4 alkyl group" substituted by one or more halogen atoms. Preferably, it is a C1-2 alkyl group substituted by one or more fluorine or chlorine, and includes, for example, a trifluoromethyl group, a difluoromethyl group, a fluoromethyl group, a pentafluoroethyl group, a tetrafluoroethyl group, a trifluoroethyl group, a difluoroethyl group, a fluoroethyl group, a trichloromethyl group, a dichloromethyl group, a chloromethyl group, a pentachloroethyl group, a tetrachloroethyl group, a trichloroethyl group, a dichloroethyl group, and a chloroethyl group.

The term "C2-6 alkenyl group" means a C2-6 hydrocarbon group having at least one double bond and includes, for example, an ethenyl(vinyl) group, a 1-propenyl group, a 2-propenyl(allyl) group, an isopropenyl group, a 1-butenyl group, a 2-butenyl group, a 3-butenyl(homoallyl) group, a pentenyl group, and a hexenyl group.

The term "C2-6 alkynyl group" means a C2-6 hydrocarbon group having at least one triple bond, and includes, for example, an ethynyl group, a 1-propynyl group, a 2-propynyl group, a 1-butynyl group, a 2-butynyl group, a 3-butynyl group, a pentynyl group, and a hexynyl group.

The term "C1-6 alkoxy group" means a —O—C1-6 alkyl group, and includes, for example, a methoxy group, an ethoxy group, a propoxy group, an isopropoxy group, a butoxy group, a sec-butoxy group, an isobutoxy group, a tert-butoxy group, a pentoxy group, a 3-methylbutoxy group, a 2-methylbutoxy group, a 1-methylbutoxy group, a 1-ethylpropoxy group, a hexyloxy group, a 4-methylpentoxy group, a 3-methylpentoxy group, a 2-methylpentoxy group, a 1-methylpentoxy group, 3-ethylbutoxy group, and a 2-ethylbutoxy group.

The term "C1-4 alkoxy group" means a —O—C1-4 alkyl group, and includes, for example, a methoxy group, an ethoxy group, a propoxy group, an isopropoxy group, a butoxy group, a sec-butoxy group, an isobutoxy group, and a tert-butoxy group.

The term "C1-3 alkoxy C1-3 alkoxy group" means a —O—C1-3 alkyl-O—C1-3 alkyl group, and includes, for example, a methoxymethoxy group, a methoxyethoxy group, and an ethoxyethoxy group.

The term "C1-6 alkylthio group" means a —S—C1-6 alkyl group, and includes, for example, a methylthio group, an ethylthio group, a propylthio group, an isopropylthio group, a butylthio group, a sec-butylthio group, an isobutylthio group, a tert-butylthio group, a pentylthio group, a 3-methylbutylthio group, a 2-methylbutylthio group, a 1-methylbutylthio group, a 1-ethylpropylthio group, a hexylthio group, a 4-methylpentylthio group, a 3-methylpentylthio group, a 2-methylpentylthio group, a 1-methylpentylthio group, a 3-ethylbutylthio group, and a 2-ethylbutylthio group.

The term "halogen" means fluorine (F), chlorine (CO, bromine (Br) or iodine (I), and is preferably fluorine or chlorine.

The term "C3-10 cycloalkyl group" means a saturated C3-10 carbocyclic group, and includes, for example, a cyclopropyl group, a cyclobutyl group, a cyclopentyl group, a cyclohexyl group, a cycloheptyl group, a cyclooctyl group, a cyclononyl group, and a cyclodecyl group.

The term "C3-10 cycloalkenyl group" means a C3-10 carbocyclic group having at least one double bond, and includes, for example, a cyclopentenyl group, a cyclohexenyl group, and a cycloheptenyl group.

The term "C6-12 aryl group" means a monocyclic or bicyclic aromatic carbocyclic ring with six to twelve ring carbon atoms, and includes, for example, a phenyl group, a naphthyl group, an indanyl group, an indenyl group, and an isoindenyl group. It is preferably a phenyl group.

The term "3- to 12-membered monocyclic heterocyclic ring" means an aromatic or non-aromatic monocyclic heterocyclic ring having three to twelve ring-constituting atoms that include one or more (for example, one to four) heteroatoms selected from N, O, and S. The bonding position of the heteroatoms is not particularly limited, and they may be linked at any position. Specific examples of the 3- to 12-membered monocyclic heterocyclic ring include pyrrolidine, oxazolidine, isooxazolidine, oxazoline, isooxazoline, thiazolidine, isothiazolidine, thiazoline, isothiazoline, imidazolidine, imidazoline, furan, thiophene, pyrrole, oxazole, isoxazole, thiazole, isothiazole, furazan, imidazole, pyrazole, piperidine, piperazine, morpholine, thiomorpholine, tetrahydropyran, dioxane, tetrahydrothiopyran, pyran, thiopyran, pyridine, pyrazine, pyrimidine, and pyridazine.

The term "3- to 12-membered monocyclic alicyclic monospiro ring" means a group in which a monocyclic alicyclic hydrocarbon having three to twelve ring-constituting atoms forms a ring together with one carbon atom on a C1-6 alkylene group. The spirocarbon position on the C1-6 alkylene group is not particularly limited, and it may be shared at a desired position. Specifically, the 3- to 12-membered monocyclic alicyclic monospiro ring includes for example, cyclopropanone, cyclobutanone, cyclopentanone, cyclohexanone, cyclopropane, cyclobutane, cyclopentane, cyclohexane, cyclopropene, cyclobutene, cyclopentene, and cyclohexene.

The term "3- to 12-membered monocyclic heterocyclic monospiro ring" means a group in which a monocyclic non-aromatic heterocyclic ring having three to twelve ring-constituting atoms that include one or more (for example, one to four) heteroatoms selected from N, O, and S forms a ring together with one carbon atom in a C1-6 alkylene group. The bonding position(s) of heteroatom(s) is not particularly limited, and they may be bonded at a desired position(s). Moreover, the position of a spirocarbon on a C1-6 alkylene group is not particularly limited, and it may be shared by a C1-6 alkylene group at a desired position. Specifically, the 3- to 12-membered monocyclic heterocyclic monospiro ring includes for example, oxetane, tetrahydrofuran, tetrahydropyran, thietane, tetrahydrothiophene, tetrahydrothiopyran, azetidine, pyrrolidine, piperidine, oxetanone, tetrahydrofuranon, tetrahydropyranone, azetidinone, pyrrolidinone, piperidinone, dioxolane, dioxane, dithiolane, and dithiane.

The term "C1-6 alkylene group" means a divalent group derived by further removing arbitrary hydrogen atom from the above-defined "C1-6 alkyl group".

The term "C2-6 alkenylene group" means a divalent group derived by further removing an arbitrary hydrogen atom from the above-defined "C2-6 alkenyl group".

The term "C2-6 alkynylene group" means a divalent group derived by further removing an arbitrary hydrogen atom from the above-defined "C2-6 alkynyl group".

The term "C3-10 cycloalkylene group" means a divalent group derived by further removing an arbitrary hydrogen atom from the above-defined "C3-10 cycloalkyl group".

The term "C3-10 cycloalkenylene group" means a divalent group derived by further removing an arbitrary hydrogen atom from the above-defined "C3-10 cycloalkenyl group".

The term "C6-12 arylene group" means a divalent group derived by further removing an arbitrary hydrogen atom from the above-defined "C6-12 aryl group".

The term "-3- to 12-membered monocyclic heterocyclic ring-" means a divalent group derived by removing two arbitrary hydrogen atoms from the above-defined "3- to 12-membered monocyclic heterocyclic ring".

When simply denoted as "ring", this term refers to a concept encompassing all of the above-mentioned "C3-10 cycloalkyl group", "C3-10 cycloalkenyl group", "C6-12 aryl group", and "3- to 12-membered monocyclic heterocyclic ring".

When R5, R6, and R7 in the formula represent a "C1-6 alkylene group which may have a substituent", the substituent preferably includes groups selected from Group A shown below. Group A: a C1-6 alkyl group which may have a substituent (the substituent is a hydroxyl group or a dimethylamino group), a halogen atom, a hydroxyl group, a cyano group, a group represented by —NR9R10 [R9 and R10 each independently represents a hydrogen atom, a C1-3 alkyl group, or a group represented by —C(=O)CH3, —C(=O)CF3, —C(=O)CH(NH2)CH(CH3)2, or —C(=O)CH(NH2)(4-OH)Ph], a group represented by —C(=O)NR11R12 [R11 and R12 each independently represents a hydrogen atom or an optionally substituted C1-6 alkyl group (a substituent represents at least one substituent selected from the group consisting of: a hydroxyl group, a C1-6 alkoxy group, a C1-3 alkoxy C1-3 alkoxy group, a morpholinyl group, a piperidinyl group, and a 4-methylpiperidinyl group), or R11 and R12 together form a 3- to 12-membered monocyclic heterocyclic ring], a group represented by —C(=O)OR13 [R13 represents a hydrogen atom or a C1-3 alkyl group], an optionally substituted 3- to 12-membered monocyclic alicyclic monospiro ring (a substituent represents at least one substituent selected from the group consisting of: a hydrogen atom, a halogen atom, a cyano group, a hydroxyl group, a C1-6 alkyl group, a C2-6 alkenyl group, a C1-6 alkoxy group, a C1-6 alkylthio group, a C1-6 acyl group, a carboxyl group, a carbamoyl group, a C1-6 alkoxycarbonyl group, a C1-6 alkoxycarbonyloxy group, a mono C1-6 alkylaminocarbonyl group, a mono C1-6 alkylaminocarbonyloxy group, a di C1-6 alkylaminocarbonyl group, a di C1-6 alkylaminocarbonyloxy group, an amino group, a mono C1-6 alkylamino group, a di C1-6 alkylamino group, a mono C1-6 acylamino group, a C1-6 alkylsulfonylamino group, a C1-6 alkoxycarbonylamino group, an N'-mono C1-6 alkylureido group, an N',N'-di C1-6 alkylureido group, and such), or an optionally substituted 3- to 12-membered monocyclic heterocyclic monospiro ring (a substituent represents at least one substituent selected from the group consisting of: a hydrogen atom, a halogen atom, a cyano group, a hydroxyl group, an oxo group, a C1-6 alkyl group, a C2-6 alkenyl group, a C1-6 alkoxy group, a C1-6 alkylthio group, a C1-6 acyl group, a carboxyl group, a carbamoyl group, a C1-6 alkoxycarbonyl group, a C1-6 alkoxycarbonyloxy group, a mono C1-6 alkylaminocarbonyl group, a mono C1-6 alkylaminocarbonyloxy group, a di C1-6 alkylaminocarbonyl group, a di C1-6 alkylaminocarbonyloxy group, an amino group, a mono C1-6 alkylamino group, a di C1-6 alkylamino group, a mono C1-6 acylamino group, a C1-6 alkylsulfonylamino group, a C1-6 alkoxycarbonylamino group, an N'-mono C1-6 alkylureido group, an N',N'-di C1-6 alkylureido group, and such).

A plurality of such substituents may be present. When multiple substituents are present, they may be the same or different. The number of such substituents is preferably one or two.

When R8 and R8' in the formula are "an optionally substituted C1-6 alkyl group", the substituent preferably includes a group selected from Group B shown below.

Group B: a hydroxyl group, a morpholinyl group, a piperidinyl group, a 4-methylpiperidinyl group, a halogen atom, a hydroxyl group, an amino group, a cyano group, a C6-12 aryl group, or a C1-6 alkoxy group.

A plurality of such substituents may exist. When multiple substituents are present, they may be the same or different. The number of such substituents is preferably one or two.

Simulations

In a non-limiting embodiment, the cyclization reactions of the present invention can be performed at an industrial scale using conditions obtained based on the results of preliminary tests on the cyclization reactions.

In the present embodiment, the term "simulation" refers to a test that is performed before performing an industrial scale reaction, i.e. a method of producing a cyclic organic compound comprising the step of cyclizing a cyclization precursor of the cyclic organic compound in at least one continuous stirred tank reactor, and that is performed in order to obtain optimum conditions for the industrial scale reaction. The simulations of the present invention comprise the step of performing a preliminary test and the step of calculating conditions for performing the cyclization reaction at an industrial scale based on the results of the preliminary test. A "simulation" in the present invention is not particularly limited as long as it is a test carried out for such purposes, and it also includes, for example, obtaining conditions that are already obtainable based on known values and such described in literature.

In the present embodiment, the "industrial scale" preferably refers to a plant-level scale or plant scale, but is not particularly limited thereto. It includes a trial scale (bench scale) and a lab scale on a laboratory level, which are performed at stages before production of the cyclic organic compounds at a plant scale.

Therefore, in a non-limiting embodiment, the present invention also provides methods of obtaining conditions for cyclizing a cyclization precursor of a cyclic organic compound at an industrial scale in at least one continuous stirred tank reactor. Furthermore, in a non-limiting embodiment, the present invention also provides methods of obtaining conditions for producing a cyclic organic compound at an industrial scale in at least one continuous stirred tank reactor.

In the preliminary test in the present invention, data on concentration change over time at one or more temperatures are obtained for at least one selected from the group consisting of a cyclization precursor, a cyclic organic compound, one or more intermediates, and one or more byproducts. The preliminary test of the present invention can be performed by methods described in the Examples, or by methods known to those skilled in the art.

In a non-limiting embodiment, optimum conditions for cyclization at an industrial scale using a CSTR(s) can be obtained by a method comprising the following steps:
  (i) obtaining data on concentration change over time at multiple temperatures for at least one selected from the group consisting of a cyclization precursor, a cyclic organic compound, one or more intermediates, and one or more byproducts in a preliminary test;
  (ii) determining a reaction rate constant $k_n$ for each of the temperatures at which the preliminary test was performed, by using the data on concentration change obtained in step (i) and a reaction rate equation for the cyclization reaction (equations (V) to (IX) or equations (XI) to (XIII) herein);
  (iii) determining frequency factor $A_n$ and activation energy $E_n$ by using the temperatures used in step (i), the reaction rate constant $k_n$ determined in step (ii), and the following equation (II):

$$k_n = A_n \exp\left(\frac{-E_n}{RT}\right) \tag{II}$$

(wherein $k_n$ represents the reaction rate constant, $A_n$ represents the frequency factor, $E_n$ represents the activation energy, R represents the gas constant, and T represents the temperature);
  (iv) determining a reaction rate constant $k_n$ at a temperature for cyclization in a CSTR(s) by using the frequency factor $A_n$ and the activation energy $E_n$ determined in step (iii), the above-mentioned equation (II), and the above-mentioned reaction rate equation; and
  (v) obtaining the aforementioned conditions by using the reaction rate constant $k_n$ determined in step (iv), the aforementioned reaction rate equation, and the following CSTR mass balance equation (III):

$$\tau = \frac{C_{0,n} - C_n}{-r_n} \tag{III}$$

(wherein $r_n$ represents the reaction rate, $\tau$ represents the residence time (space time), $C_0$ represents the supply concentration, and C represents the concentration).

In the above-mentioned embodiment, the "multiple temperatures" of step (i) are preferably two or more, three or more, four or more, or five or more temperatures, but are not limited thereto.

In the above-mentioned embodiment, the reaction rate constant (k) at a temperature for cyclization in the CSTR can be determined by substituting the frequency factor value (A) and the activation energy value (E) obtained in step (iii) into the above-mentioned Arrhenius' equation (II). By substituting the reaction rate constant (k) at the temperature for cyclization in the CSTR into the reaction rate equation for the cyclization reaction and setting the initial concentration condition, the change in concentration over time of each component at the temperature for cyclization in the CSTR can be determined. In the present invention, the temperature for cyclization in the CSTR can be set arbitrarily, which allows optimization of the temperature for industrial-scale cyclization.

The optimum condition for the "temperature for cyclization in a CSTR" in the present invention is preferably a temperature condition for a cyclization reaction in a CSTR at which the concentration of a target molecule (concentration of a cyclic organic compound) is maximized, but is not limited thereto.

Carrying out the above-mentioned steps (i) to (v) enables a simulation of the progress of a cyclization reaction at any temperature (concentration change over time for each component), and thereby enables, for example, prediction of the reaction conversion rate (percentage of the cyclization precursor spent by the reaction) and selectivity (percentage of the target molecule among all products) in this reaction. Based on such simulation results, the optimum conditions for an industrial-scale reaction (for example, supply concentration (initial concentration) of the cyclization precursor, and residence time in the reactor, reaction temperature, and such) can be determined.

In a non-limiting embodiment, the temperature for cyclization in a CSTR(s) of step (iv) can also be appropriately selected by those skilled in the art from the multiple temperatures used in step (i) to obtain the data on concentration change or from temperatures around those temperatures (±5° C. or ±10° C.), without performing the above-described step of optimizing the temperature at an industrial scale.

In a non-limiting embodiment, the optimum conditions for carrying out an industrial-scale cyclization using a CSTR(s) can be obtained by a method comprising the following steps:
  (i) obtaining data on concentration change over time at a single temperature for at least one selected from the group consisting of a cyclization precursor, a cyclic organic compound, one or more intermediates, and one or more byproducts, in a preliminary test;
  (ii) determining a reaction rate constant $k_n$ by using the data on concentration change obtained in step (i) and a reaction rate equation relating to the cyclization reaction (equations (V) to (IX) or equations (XI) to (XIII) below); and
  (iii) obtaining the aforementioned conditions using the reaction rate constant $k_n$ determined in step (ii), the aforementioned reaction rate equation, and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration).

In the present invention, "intermediate(s)" refers to a substance(s) generated during a chemical reaction of reactants to products. When the chemical reaction is a multi-step reaction, it refers to substances generated at each elementary reaction.

In the present invention, "byproduct(s)" refers to a product(s) other than a main product (target molecule) among products resulting from chemical reactions. Byproducts in the present invention include multimers (linear forms) of cyclization precursors of cyclic organic compounds, cyclized forms of these multimers, and such, but are not limited thereto. Multimers include dimers, trimers, and such, but are not limited thereto.

In the present invention, "concentration change" refers to changes in the concentration of a substance to be measured with respect to change in time. In the present invention, it is necessary to obtain data on concentration change of a cyclization precursor. In addition, it is preferable to obtain data on concentration change of at least one selected from the group consisting of a cyclic organic compound, one or more intermediates, and one or more byproducts. Particularly, in the present invention, obtaining data on concentration change of the cyclization precursor and the cyclic organic compound is preferred, and obtaining data on concentration change of the cyclization precursor, the cyclic organic compound, and the byproduct(s) is particularly preferred. Data on concentration change can be obtained by methods known to those skilled in the art such as methods described in Examples.

In a non-limiting embodiment, the elementary reactions of the cyclization reaction of the present invention can be presented by the following formula (IV):

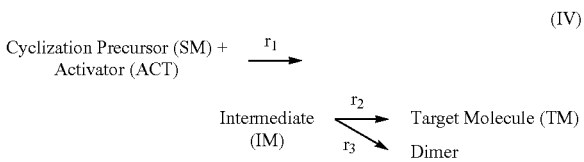

(IV)

Here, in (IV) above, when the reaction that yields the intermediate (IM) from the cyclization precursor (SM) and the activator (ACT) is faster than the reactions yielding the target molecule (TM) and the dimer (Dimer) from the intermediate (IM), in a non-limiting embodiment, the elementary reactions of the cyclization reaction of the present invention can also be presented as the following formula (X):

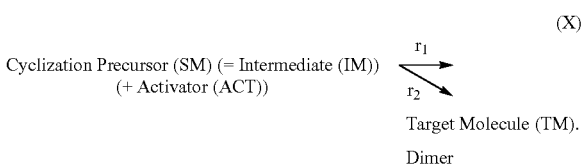

(X)

When the elementary reactions of the cyclization reaction are presented by the formula (IV) above, the reaction rate constants $k_1$, $k_2$, and $k_3$ can be determined using any one of the following equations (V) to (IX) or combinations thereof:

$$r_{SM} = \frac{dC_{SM}}{dt} = -k_1 C_{SM} C_{ACT} \quad \text{(V)}$$

$$r_{ACT} = \frac{dC_{ACT}}{dt} = -k_1 C_{SM} C_{ACT} \quad \text{(VI)}$$

$$r_{IM} = \frac{dC_{IM}}{dt} = k_1 C_{SM} C_{ACT} - k_2 C_{IM} - 2k_3 C_{IM}^2 \quad \text{(VII)}$$

$$r_{TM} = \frac{dC_{TM}}{dt} = k_2 C_{IM} \quad \text{(VIII)}$$

$$r_{Dimer} = \frac{dC_{Dimer}}{dt} = k_3 C_{IM}^2 \quad \text{(IX)}$$

(wherein r represents the reaction rate, TM represents the cyclic organic compound, SM represents the cyclization precursor, ACT represents the activator, IM represents the intermediate, Dimer represents the dimer, and C represents the concentration (M)).

The above-mentioned $k_1$, $k_2$, and $k_3$ correspond to the reaction rate constants in the following reactions in the formula (IV) above:
- $k_1$: cyclization precursor (SM)+activator (ACT)→intermediate (IM)
- $k_2$: intermediate (IM)→target molecule (TM)
- $k_3$: intermediate (IM)→dimer (Dimer)

On the other hand, when the elementary reactions of the cyclization reaction are presented by the formula (X) above, the reaction rate constants $k_1$ and $k_2$ can be determined using any one of the following equations (XI) to (XIII) or combinations thereof:

$$r_{SM} = \frac{dC_{SM}}{dt} = \frac{dC_{ACT}}{dt} = -k_1 C_{SM} C_{ACT} - 2k_2 C_{SM}^2 C_{ACT}^2 \quad \text{(XI)}$$

$$r_{TM} = \frac{dC_{TM}}{dt} = k_1 C_{SM} C_{ACT} \quad \text{(XII)}$$

$$r_{Dimer} = \frac{dC_{Dimer}}{dt} = k_2 C_{SM}^2 C_{ACT}^2 \quad \text{(XIII)}$$

(wherein r represents the reaction rate, TM represents the target molecule, SM represents the cyclization precursor (=intermediate), ACT represents the activator, Dimer represents the dimer, and C represents the concentration (M)).

The above-mentioned k1 and k2 correspond to the reaction rate constants in the following reactions in the formula (X) above:
- k1: cyclization precursor (SM) (=intermediate (IM)) (+activator (ACT))→target molecule (TM)
- k2: cyclization precursor (SM) (=intermediate (IM)) (+activator (ACT))→dimer (Dimer)

One skilled in the art can appropriately judge whether a simplified reaction formula like formula (X) mentioned above is applicable or not depending on the accuracy of the experimental data required. Generally, those skilled in the art can appropriately judge it depending on whether the results of concentration change over time obtained in advance for the above-mentioned cyclic organic compound can be reproduced using equations (XI) to (XIII) below. As a criterion for the judgement, a residual sum of squares can be used.

Furthermore, in cases such as where the activator (ACT) concentration is higher than the cyclization precursor (SM) concentration in the above-mentioned formulae (IV) and (X), the activator concentration (CACT) in the reaction rate equations (V) to (IX) and (XI) to (XIII) can be omitted in some cases. One skilled in the art can appropriately judge whether or not this omission is applicable depending on the accuracy of the experimental data required. Generally, one skilled in the art can appropriately judge it depending on whether the results of concentration change over time obtained in advance for the above-mentioned cyclic organic compound can be reproduced using the equations in which the activator concentration (CACT) is omitted. As a criterion for the judgement, a residual sum of squares can be used.

Alternatively, in the present invention, the above-mentioned rate constants can also be calculated as follows. The above-mentioned Arrhenius' equation (II) can be represented as the following equation (XIV) by taking the logarithm:

$$lnk = -\frac{E}{RT} + lnA \qquad (XIV)$$

The results of concentration change over time for the above-mentioned cyclic organic compound obtained by cyclizing the above-mentioned cyclization precursor, and the above-mentioned reaction rate equations (V) to (IX) and (XI) to (XIII), are used to calculate a reaction rate constant (k) in these equations. The logarithm of the reaction rate constant (lnk) and the inverse of the temperature at which the cyclization was carried out (1/T) are plotted on ordinate and abscissa, respectively, to produce an Arrhenius plot. Then, the frequency factor value (A) and the activation energy value (E) can be determined by using the technique of regression analysis known to those skilled in the art (intercept: lnA; and slope: −E/R).

One skilled in the art can appropriately perform these calculations using, for example, Excel provided by Microsoft Corporation. On the other hand, besides the above-mentioned technique, software can also be used to determine the frequency factor value (A) and the activation energy value (E) directly. For example, gPROMS provided by PSE and Aspen Batch modeler provided by Aspen Technology can be used.

By substituting the frequency factor value (A) and the activation energy value (E) obtained by the above-described technique into the above-mentioned Arrhenius' equation (II), the reaction rate constant (k) at any temperature can be determined. By substituting the reaction rate constant (k) at an arbitrary temperature for cyclization in a CSTR into the reaction rate equations (V) to (IX) and (XI) to (XIII), and by setting the initial concentration conditions, concentration change over time for each component at the arbitrary temperature can be determined. Determining the concentration change over time enables optimization of the temperature used in an industrial-scale operation. Optimum conditions for the "temperature for cyclization in a CSTR" of the present invention are preferably cyclization reaction temperature conditions that will maximize the concentration of the target molecule, but are not limited thereto.

In the present invention, the optimum cyclization reaction condition values for an industrial-scale operation can be calculated by using:
1) reaction rate constant $k_n$ determined by the above-mentioned methods, or
2) reaction rate constant $k_n$ determined by using the data on concentration change obtained at a single temperature and the reaction rate equations (V) to (IX) and (XI) to (XIII) relating to the cyclization reaction, and the following CSTR mass balance equation (XV):

$$\tau = \frac{C_{0,n} - C_n}{-r_n} \qquad (XV)$$

(wherein $r_n$ represents the reaction rate ((V) to (IX), and (XI) to (XIII)), $\tau$ represents the residence time (space time), $C_0$ represents the supply concentration, and C represents the concentration).

The concentration of each component at the outlet can be determined, for example, by setting the residence time, supply concentration, and temperature, and using equation (XV) and equations (V) to (IX), and (XI) to (XIII). When a simple reaction is taking place in a CSTR, the mass balance of reactant A with the assumption of steady state, which allows the accumulation term to be zero, can be expressed by the following equation (see *Kagaku Kogaku* (Chemical Engineering) (revised 3rd edition) *Kaisetsu to Enshu* (Explanation and Practice) (Editorial supervision by The Society of Chemical Engineers, Japan; Y., Tada Ed.) Chapter 12 Reaction Engineering, 12.5 Continuous Stirred Tank Reactor (page 316)):

$$v_0 C_{A,0} - v C_A - (-r_A) V = 0 \qquad (XVI)$$

(wherein $v_0$ represents the volume of influent to the reaction system per unit time, $C_{A,0}$ represents the concentration of A in the influent (initial concentration), v represents the volume of effluent from the reaction system per unit time, $C_A$ represents the concentration of A in the effluent (outlet concentration), $r_A$ represents the reaction rate of A (change in concentration of A per unit time), V represents the reactor volume, $v_0 C_{A,0}$ represents the inflow of A per unit time, $vC_A$ represents the outflow of A per unit time, $(-r_A)V$ represents the reaction quantity of A per unit time, zero on the right side represents the accumulation term).

When the reaction system is liquid, and the change in volume accompanied with the reaction is assumed to be negligible, the flow volume can be regarded as $v = v_0$. Then, transforming the equation (XVI) using $\tau = V$ (reactor volume)/$v_0$ (flow volume per unit time) yields the following equation, which is called the CSTR design equation:

$$\tau = \frac{C_{A,0} - C_A}{-r_A} = \frac{C_{A,0} X_A}{-r_A} \qquad (XVII)$$

(wherein $r_n$ represents the reaction rate, $\tau$ represents the residence time (space time), $C_0$ represents the supply concentration, C represents the concentration, and $X_A$ represents the reaction conversion rate).

$\tau = V$ (reactor volume)/$v_0$ (flow volume per unit time) indicates how many times the reactor volume is larger than the volume processed per unit time, or indicates the time taken to process the raw materials equivalent to the reactor volume, and is called space time. The inverse of space time is called space velocity (SV).

In a non-limiting embodiment, the optimum cyclization reaction condition values at an industrial scale in the present invention are one or more reaction condition values selected from the group consisting of the flow volume of the continuous stirred tank reactor, concentration of the cyclization precursor, and concentration of the cyclic organic compound, but are not limited thereto.

Furthermore, in a non-limiting embodiment, the present invention relates to programs for making a computer execute the following procedures to obtain conditions for cyclizing a cyclization precursor of a cyclic organic compound at an industrial scale in at least one continuous stirred tank reactor (CSTR), and relates to recording media in which such a program is recorded:

(i) a procedure for determining a reaction rate constant $k_n$ at each temperature at which a preliminary test was performed, by using:

data on concentration change over time at multiple temperatures for at least one selected from the group consisting of the cyclization precursor, the cyclic organic compound, one or more intermediates, and one or more byproducts, obtained in the preliminary test, and a reaction rate equation(s) relating to the cyclization reaction (equations (V) to (IX) or equations (XI) to (XIII) herein);

(ii) a procedure for determining the frequency factor $A_n$ and the activation energy $E_n$ by using the temperatures used in step (i), the reaction rate constant $k_n$ determined in step (i), and the following equation (II):

$$k_n = A_n \exp\left(\frac{-E_n}{RT}\right) \quad \text{(II)}$$

(wherein $k_n$ represents the reaction rate constant, $A_n$ represents the frequency factor, $E_n$ represents the activation energy, R represents the gas constant, and T represents the temperature);

(iii) a procedure for determining a reaction rate constant $k_n$ at a temperature for cyclization in the CSTR by using the frequency factor $A_n$ and the activation energy $E_n$ determined in (ii), the above-mentioned equation (II), and the above-mentioned reaction rate equation(s); and (iv) a procedure for obtaining the aforementioned conditions using the reaction rate constant $k_n$ determined in (iii), the aforementioned reaction rate equation(s), and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration).

In a non-limiting embodiment, the programs of the present invention are programs for making a computer execute the following procedures:

(i) a procedure for determining a reaction rate constant $k_n$ by using:

data on concentration change over time at a single temperature for at least one selected from the group consisting of the cyclization precursor, the cyclic organic compound, one or more intermediates, and one or more byproducts, obtained in a preliminary test, and a reaction rate equation(s) relating to the cyclization reaction (equations (V) to (IX) or equations (XI) to (XIII) herein); and (ii) a procedure for obtaining the aforementioned conditions using the reaction rate constant $k_n$ determined in procedure (i), the aforementioned reaction rate equation(s), and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration).

In a non-limiting embodiment, the programs of the present invention are programs for executing the above-mentioned procedures using a computer which comprises a means of inputting data, a means of memorizing data, a means of processing data, and a means of outputting data. The programs of the present invention can be made by methods known to those skilled in the art based on formulae (IV) and (X) described herein, which are the formulae of the elemental reactions of the cyclization reaction, equations (V) to (IX) and (XI) to (XIII) for calculating reaction rate constants, Arrhenius' equation (II), CSTR mass balance equation (III), and such.

Furthermore, in a non-limiting embodiment, the present invention provides systems for obtaining conditions for cyclizing a cyclization precursor of a cyclic organic compound at an industrial scale in at least one continuous stirred tank reactor (CSTR), the systems comprising:

(i) a means of determining a reaction rate constant $k_n$ at each temperature at which a preliminary test was performed by using:

data on concentration change over time at multiple temperatures for at least one selected from the group consisting of the cyclization precursor, the cyclic organic compound, one or more intermediates, and one or more byproducts, obtained in the preliminary test, and a reaction rate equation(s) relating to the cyclization reaction (equations (V) to (IX), or equations (XI) to (XIII) herein);

(ii) a means of determining the frequency factor $A_n$ and the activation energy $E_n$ by using the temperatures used in means (i), the reaction rate constants $k_n$ determined in step (i), and the following equation (II):

$$k_n = A_n \exp\left(\frac{-E_n}{RT}\right) \quad \text{(II)}$$

(wherein $k_n$ represents the reaction rate constant, $A_n$ represents the frequency factor, $E_n$ represents the activation energy, R represents the gas constant, and T represents the temperature);

(iii) a means of determining a reaction rate constant $k_n$ at a temperature for cyclization in a CSTR by using the frequency factor $A_n$ and the activation energy $E_n$ determined in step (ii), the above-mentioned equation (II), and the above-mentioned reaction rate equation(s); and (iv) a means of obtaining the aforementioned conditions using the reaction rate constant kn determined by means (iii), the aforementioned reaction rate equation(s), and the following CSTR mass balance equation (III):

$$\tau = \frac{C_{0,n} - C_n}{-r_n} \quad \text{(III)}$$

(wherein $r_n$ represents the reaction rate, $\tau$ represents the residence time (space time), $C_0$ represents the supply concentration, and C represents the concentration).

Furthermore, in a non-limiting embodiment, the present invention provides systems for obtaining conditions for cyclizing a cyclization precursor of a cyclic organic compound at an industrial scale in at least one continuous stirred tank reactor (CSTR), the systems comprising:
(i) a means of determining a reaction rate constant $k_n$ by using:
data on concentration change over time at a single temperature for at least one selected from the group consisting of the cyclization precursor, the cyclic organic compound, one or more intermediates, and one or more byproducts, obtained in a preliminary test, and
a reaction rate equation(s) relating to the cyclization reaction (equations (V) to (IX), or equations (XI) to (XIII) herein); and
(ii) a means of obtaining the aforementioned conditions using the reaction rate constant kn determined by means (i), the aforementioned reaction rate equation(s), and the following CSTR mass balance equation (III):

$$k_n = A_n \exp\left(\frac{-E_n}{RT}\right) \quad \text{(II)}$$

(wherein $r_n$ represents the reaction rate, $\tau$ represents the residence time (space time), Co represents the supply concentration, and C represents the concentration).

Pharmaceutical Compositions

The present invention provides peptide compounds produced by the methods of the present invention, and pharmaceutical compositions comprising such a compound.

The pharmaceutical compositions of the present invention may be formulated by known methods by introducing a pharmaceutically acceptable carrier in addition to a peptide compound produced by the methods of the present invention. Commonly used excipients, binders, lubricants, colorants, correctives, and as necessary, stabilizers, emulsifiers, absorption promoters, surfactants, pH adjusters, preservatives, antioxidants, and the like can be used for formulation, and they are blended with ingredients commonly used as raw materials of pharmaceutical preparations and formulated by conventional methods.

For example, oral preparations are manufactured by adding excipients and as necessary, binders, disintegrants, lubricants, colorants, correctives, and the like to the compounds according to the present invention or pharmaceutically acceptable salts thereof, and then formulating them into powders, fine granules, granules, tablets, coated tablets, capsules, and the like by conventional methods.

Examples of these ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of excipients include lactose, corn starch, white soft sugar, glucose, mannitol, sorbitol, microcrystalline cellulose, and silicon dioxide.

Examples of binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer, and meglumine.

Examples of disintegrants include starch, agar, gelatin powder, microcrystalline cellulose, calcium carbonate, sodium bicarbonate, calcium citrate, dextrin, pectin, and carboxymethylcellulose calcium.

Examples of lubricants include magnesium stearate, talc, polyethylene glycol, silica, and hydrogenated vegetable oil.

Colorants used are those approved as additives to pharmaceuticals. Correctives used are cocoa powder, peppermint camphor, empasm, mentha oil, borneol, powdered cinnamon bark, and the like.

It is obviously possible to sugar-coat or otherwise coat these tablets and granules appropriately as necessary. Liquid preparations such as syrups and injectable preparations are manufactured by adding pH adjusters, solubilizers, tonicity adjusting agents, and the like, and as necessary, solubilizing agents, stabilizers, and the like to the compounds according to the present invention or pharmaceutically acceptable salts thereof, and formulating them by conventional methods.

For example, they can be used parenterally in the form of injections of sterile solutions or suspensions with water or other pharmaceutically acceptable liquid. For example, they may be formulated by appropriately combining them with pharmaceutically acceptable carriers or media, specifically with sterile water, physiological saline, vegetable oils, emulsifiers, suspensions, surfactants, stabilizers, flavoring agents, excipients, vehicles, preservatives, binders, and such and by mixing them in a unit dosage form required for generally approved pharmaceutical practice. Specifically, carriers include light anhydrous silicic acid, lactose, crystalline cellulose, mannitol, starch, carmellose calcium, carmellose sodium, hydroxypropyl cellulose, hydroxypropylmethyl cellulose, polyvinyl acetal diethylamino acetate, polyvinylpyrrolidone, gelatin, medium-chain triglyceride, polyoxyethylene hydrogenated castor oil 60, sucrose, carboxymethylcellulose, corn starch, inorganic salts and such. In such formulations, the amount of active ingredient is to achieve an appropriate amount in an indicated range.

Sterile compositions for injection can be formulated using vehicles such as distilled water for injection, according to standard pharmaceutical practice.

Aqueous solutions for injection include, for example, physiological saline and isotonic solutions containing glucose or other adjuvants, for example, D-sorbitol, D-man nose, D-mannitol, and sodium chloride. It is also possible to use in combination appropriate solubilizers, for example, alcohols, specifically, ethanol, polyalcohols (for example, propylene glycol, polyethylene glycol), non-ionic surfactants (for example, Polysorbate 80 (registered trademark), HCO-50).

Oily liquids include sesame oil and soybean oil, and they may be used in combination with benzyl benzoate and/or benzyl alcohol as solubilizers. It is also possible to combine buffers (for example, phosphate buffer and sodium acetate buffer), analgesics (for example, procaine hydrochloride), stabilizers (for example, benzyl alcohol and phenol), and/or antioxidants. Ordinarily, prepared injections are filled into appropriate ampules.

Administration is preferably oral administration but is not particularly limited to oral administration. Parenteral administration specifically includes injections, transnasal administration, transpulmonary administration, or transdermal administration. Injections can be administered systemically or locally by, for example, intravenous injection, intramuscular injection, intraperitoneal injection, subcutaneous injection, or such.

A suitable administration method can be selected depending on the patient's age and symptoms. The dose of pharmaceutical compositions comprising a peptide compound produced by the methods of the present invention can be selected, for example, in the range from 0.0001 mg to 1000 mg per 1 kg of body weight per administration. Alternatively, the dose may be selected, for example, in the range from 0.001 mg to 100000 mg/body per patient; however, the dose is not necessarily limited to these numerical values. While the dose and administration method vary depending on the patient's weight, age, symptoms, and such, those skilled in the art can select an appropriate dose and administration method.

All prior art documents cited herein are incorporated by reference into this description.

EXAMPLES

Herein below, suitable specific embodiments of the present invention will be described with reference to the Examples, but it is not to be construed as being limited thereto.

Example 1 Synthesis of 4-Amino-18,20-dimethyl-7-thia-3,5,11,15-tetraaza-tricyclo[15.3.1.1$^{2,6}$]docosa-1(20),2(22),3,5,17(21),18-hexaene-10,16-dione

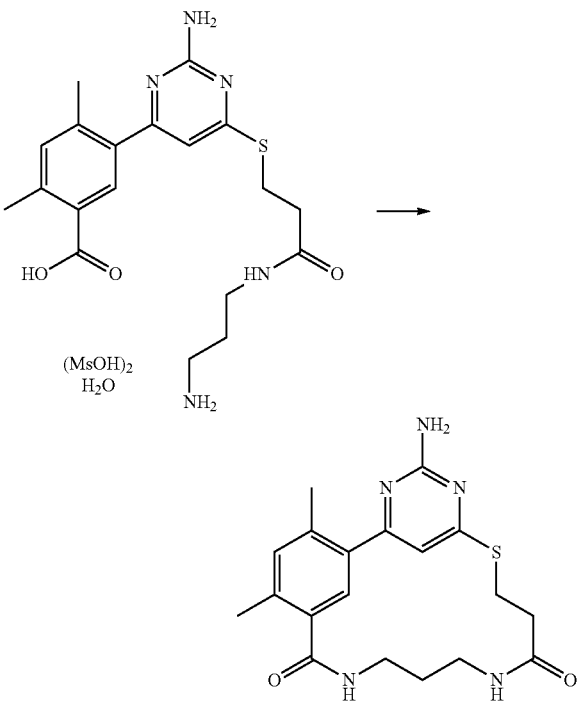

Protocol:
Reaction Rate Parameter Simulation

Data on change in concentration of each compound depending on the temperature/reaction time for each compound were collected to calculate reaction rate parameters. Cyclization precursor 2 mesylate monohydrate (7 mM) prepared in a 1:1 solution of N,N-dimethylacetamide (DMA) and acetonitrile (Solution A), and a solution containing 0-(benzotriazol-1-yl)-1,1,3,3-tetramethyluronium hexafluorophosphate (HBTU) and diisopropylethylamine (DIPEA) at concentrations of 10 mM and 32 mM, respectively, prepared in a 1:1 solution of DMA and acetonitrile (Solution B) were reacted at 0° C., 24° C. or −9° C. The reaction was quenched using a methylamine solution. A Plug flow reactor was used for the reaction, and the reaction time was adjusted by the flow rate of Solutions A and B to obtain the data shown in Table 1.

The compound concentrations were derived by assuming that the molar absorbance coefficients of the cyclization precursor and the target molecule are the same, and converting the initial concentration of the cyclization precursor (3.5 mM as a reaction mixture solution of the above-mentioned experiment) to an HPLC Area %.

TABLE 1

| | | | | | | |
|---|---|---|---|---|---|---|
| Data on compound concentration change (Example 1) | | | | | | |
| Temperature ° C. | Reaction time (sec) | Cyclization precursor (mM) | Target molecule (mM) | Dimer (Cyclized form) (mM) | Dimer (Linear form) (mM) | Byproduct 1 (mM) |
| 0 | 16 | 2.66 | 0.44 | 0.01 | 0.08 | 0.13 |
| 0 | 32 | 2.30 | 0.74 | 0.02 | 0.12 | 0.16 |
| 0 | 64 | 1.91 | 1.09 | 0.03 | 0.18 | 0.14 |
| 24 | 16 | 1.28 | 1.72 | 0.08 | 0.20 | 0.12 |

TABLE 1-continued

Data on compound concentration change (Example 1)

| Temperature ° C. | Reaction time (sec) | Cyclization precursor (mM) | Target molecule (mM) | Dimer (Cyclized form) (mM) | Dimer (Linear form) (mM) | Byproduct 1 (mM) |
|---|---|---|---|---|---|---|
| 24 | 32 | 0.84 | 2.12 | 0.13 | 0.16 | 0.12 |
| 24 | 64 | 0.61 | 2.34 | 0.17 | 0.15 | 0.08 |
| −9 | 32 | 2.26 | 0.80 | 0.01 | 0.08 | 0.20 |
| −9 | 64 | 2.01 | 1.02 | 0.02 | 0.10 | 0.21 |
| −9 | 128 | 1.89 | 1.13 | 0.03 | 0.14 | 0.17 |

From the obtained data, the mechanism of this cyclization reaction is considered to be the following. The inventors hypothesized that the reaction yielding the active intermediate from the cyclization precursor and HBTU was relatively fast, and the reaction yielding the target molecule and the dimers from the active intermediate was the rate-limiting step (James C. Collins and Keith James, Med. Chem. Commun., 2012(3), 12, 1489-1495). Furthermore, since the activator concentration did not have a great effect on the reaction rate, this was omitted. On the other hand, some of the active intermediate remained, and when the reaction was quenched with methylamine, this was detected as Byproduct 1. Sum of Byproduct 1 and raw materials was regarded as the raw material concentration, and this was used to calculate each parameter for the subsequent experiments.

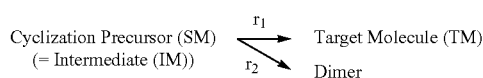

Byproduct 1: N-methylamide product; LCMS: ESI (m/z): calcd: 417.21, found: 417 [M+H]$^+$.

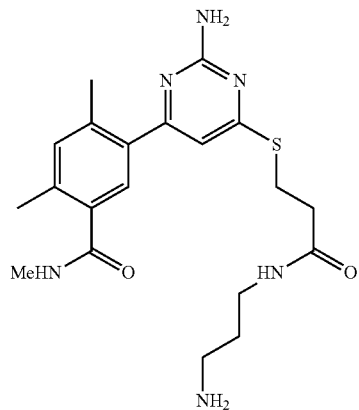 [SMILES: CNC(=O)c1cc(-c2cc(SCCC(=O)NCCCN)nc(N)n2)c(C)cc1C]

Using data on change in concentration over time and data on temperature (Table 1) obtained by the experiment, the reaction rate constants k1 and k2 at each temperature (0° C., 24° C., and −9° C.) for each elementary reaction were obtained. The following equations were used to calculate the reaction rate constants k1 and k2:

$$\frac{dC_{TM}}{dt} = k_1 C_{SM} \quad \frac{dC_{Dimer+c-Dimer}}{dt} = k_2 C_{SM}^2.$$

SM: cyclization precursor; TM: target molecule; Dimer: dimer (linear); c-Dimer: dimer (cyclic); C: concentration (M); $k_n$: reaction rate constant From the resulting reaction rate constants k1 and k2 at each temperature and from the temperature, the frequency factor (A) and the activation energy (E) for each elementary reaction were obtained from the Arrhenius plot. Microsoft Excel was used for the calculation.

As a result, the data shown in Table 2 were obtained.

TABLE 2

Frequency factor (A) and Activation energy (E) corresponding to reaction rate constants k1 and k2

| | A | E[kJ/mol] |
|---|---|---|
| k1 | 1.387E+06 [1/sec] | 43.17 |
| k2 | 3.513E+08 [L/mol/sec] | 46.09 |

The obtained frequency factor (A) and activation energy (E) for each elementary reaction were substituted into the Arrhenius' equation below, and by using the aforementioned reaction rate equations, reaction rate constants k1 and k2 were calculated for the case in which the temperature for performing the cyclization reaction in a CSTR was set to 0° C. (Table 3).

$$k_n = A_n \exp\left(\frac{-E_n}{RT}\right)$$

TABLE 3

Reaction rate constants k1 and k2 for performing cyclization reaction in CSTR

| Temperature | k1 | k2 |
|---|---|---|
| 0° C. | 7.69E−03 | 5.38E−01 |

Next, the reaction conversion rate, selectivity, and residence time when the cyclization precursor concentration was set at 0.05 mol/L and the reaction temperature was set at 0° C. were calculated using the reaction rate constants k1 and k2 of Table 3, the following mass balance equation and the reaction rate equations (Table 4).

$$\tau = \frac{C_{0,n} - C_n}{-r_n}$$

$$\frac{dC_{TM}}{dt} = k_1 C_{SM}$$

-continued $$\frac{dC_{Dimer+c-Dimer}}{dt} = k_2 C_{SM}^2$$

TABLE 4

Calculated reaction conditions (when cyclization precursor concentration is 0.05 mmol/l, reaction temperature is 0° C.)

|  | Reaction conversion rate* | Selectivity* | Residence time [θ, min] |
| --- | --- | --- | --- |
| Case 1 | 0.98 | 0.93 | 89 |
| Case 2 | 0.99 | 0.99 | 165 |
| Case 3 | 0.99 | 0.98 | 330 |

* Calculation formulae
Reaction conversion rate: (Initial concentration of cyclization precursor − Cyclization precursor concentration)/Initial concentration of cyclization precursor
Selectivity: Concentration of target molecule/(Concentration of target molecule + Concentration of dimers (linear + cyclic))

In Cases 1 to 3 of Table 4, residence time that will yield results in which the reaction conversion rate and selectivity become high were determined by calculation. In the present Example, Case 2 (Run 4) and Case 3 (Run 5) were performed.

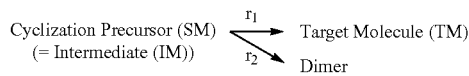

Run 1: Batch High-Dilution

Following a patent literature (Patent No.: JP5235859) and a non-patent literature (A. Suda et al., Bioorganic & Medicinal Chemistry Letters 22 (2012) 1136-1141), Cyclization precursor 2 mesylate monohydrate (39.9 mg, 86% content, 0.056 mmol) was dissolved in N,N-dimethylformamide (DMF) (16.3 mL) and tetrahydrofuran (16.3 mL), and to this mixture, N-hydroxybenzotriazole (HOBt) monohydrate (50.2 mg, 5.9 equiv.), DIPEA (0.23 mL, 23.6 equiv.), and 1-ethyl-3-(3'-dimethylaminopropyl)carbodiimide hydrochloride (125.7 mg, 11.7 equiv.) were added in that order. The obtained mixture was allowed to react at room temperature for 13 hours. When the solution concentration of the target molecule in the reaction solution was quantified to calculate the yield, it corresponded to 18.5 mg (86% yield). (Two-step isolation yield of 21% according to A. Suda et al., Bioorganic & Medicinal Chemistry Letters 22 (2012) 1136-1141).

Run 2: Batch High-Dilution

Conforming to Run 1, the cyclization precursor (40.5 mg, 86% content, 0.057 mmol) was dissolved in DMF (16.3 mL) and acetonitrile (16.3 mL), and then HBTU (30.5 mg, 1.4 equiv.) and DIPEA (0.046 mL, 4.6 equiv.) were added to this mixture in that order. The obtained mixture was allowed to react at room temperature for one hour. When the solution concentration of the target molecule in the reaction solution was quantified to calculate the yield, it corresponded to 18.4 mg (84% yield).

Run 3: Batch Pseudo High-Dilution

To a solution of HBTU (0.7441 g, 1.4 equiv.) and DMA (5 mL) in acetonitrile (15 mL), a solution of the cyclization precursor compound (1.0036 g, 86% content, 1.41 mmol) and DIPEA (1.14 mL, 4.6 equiv.) in DMA (10 mL) was added dropwise at 0° C. over a period of 300 minutes. Sixty minutes later, when the solution concentration of the target molecule was quantified to calculate the yield, it corresponded to 485.2 mg (89% yield).

Run 4: CSTR

The cyclization precursor (2.3004 g, 86% content, 3.22 mmol) and DIPEA (2.6 mL, 4.6 equiv.) were dissolved in DMA (31.9 mL). The substrate concentration was 0.09 mmol/mL. Meanwhile, HBTU (1.7042 g, 1.4 equiv.) was dissolved in acetonitrile (34.5 mL). The reagent concentration was 0.13 mmol/mL. These solutions were added at 0° C. to 16.5 mL of a DMA/acetonitrile (1/1) solution respectively at an input speed of 0.05 mL/min, and the reaction solutions were drawn out at the same time at an output speed of 0.1 mL/min. Sampling was performed by collecting the reaction solution at 165 minutes (θ*), 330 minutes (2θ), 495 minutes (3θ), and 660 minutes (4θ) after starting the operation, and these samples were quenched using a dimethylamine solution. All of the output solutions were put together, and when the concentration was quantified to calculate the yield, it corresponded to 987.2 mg (87% yield).
*θ=elapsed time/average residence time Run 5: CSTR The cyclization precursor (2.3001 g, 86% content, 3.22 mmol) and DIPEA (2.6 mL, 4.6 equiv.) were dissolved in DMA (31.9 mL). The substrate concentration was 0.09 mmol/mL. Meanwhile, HBTU (1.7083 g, 1.4 equiv.) was dissolved in acetonitrile (34.5 mL). The reagent concentration was 0.13 mmol/mL. These solutions were added at 0° C. to 33 mL of a DMA/acetonitrile (1/1) solution respectively at an input speed of 0.05 mL/min, and the reaction solutions were drawn out at the same time at an output speed of 0.1 mL/min. Sampling was performed by collecting the reaction solution at 165 minutes (0.5θ), 330 minutes (θ), and 495 minutes (1.5θ) after starting the operation, and these samples were quenched using a dimethylamine solution.

Analysis Condition:

HPLC, LCMS Condition:

Column: Ascentis C18, 4.6 mm I.D.×50 mmL, 2.7 μm, Supelco

Mobile Phase: A) Water:TFA=2000:1, B) Acetonitorile:TFA=2000:1

Column Temperature: 30° C.

Flow rate: 1.0 mL/min

Gradient (B %): 0-3.5 min (5→23), 3.5-8.0 min (23→61), 8.0-9.5 min (61→100), 9.5-9.6 min (100), 9.6-9.7 min (100→5), 9.7-12.0 min (5).

MS Detection Mode: ESI (LC/MS): m/z

Target Molecule:

LCMS: ESI (m/z): 386 [M+H]$^+$, Run: 3.9 min $^1$H NMR (DMSO-d6): Identical to the patent literature Cyclization Precursor:

Content: 86% (from data of $^1$H M NMR: DMSO-d6, Internal standard: 1,3,5-trimethoxybenzene)

LCMS: ESI (m/z): calcd; 404.18, found; 404 [M+H]+, eluted time: 3.6 min.

$^1$H-NMR (DMSO-D6) δ: 8.14 (1H, t, J=5.7 Hz), 7.91 (1H, s), 7.76-7.66 (1H, m), 7.73 (2H, br s), 7.34 (1H, s), 6.99 (1H, s), 3.41 (2H, t, J=6.8 Hz), 3.16-3.12 (2H, m), 2.83-2.77 (2H, m), 2.60 (2H, t, J=6.8 Hz), 2.57 (3H, s), 2.40 (6H, s), 2.38 (3H, s), 1.73-1.67 (2H, m).

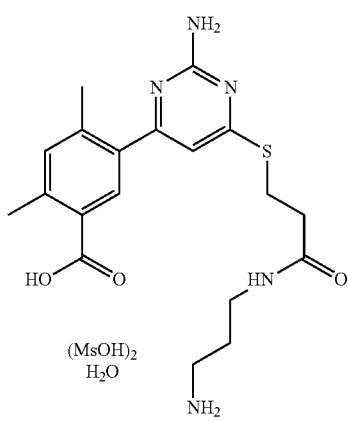 [SMILES: Cc1cc(C)c(-c2cc(SCCC(=O)NCCCN)nc(N)n2)cc1C(=O)O]

Dimer (Cyclized Form)

LCMS: ESI (m/z): calcd: 771.32, found: 771 [M+H]$^+$, eluted time: 4.7 min.

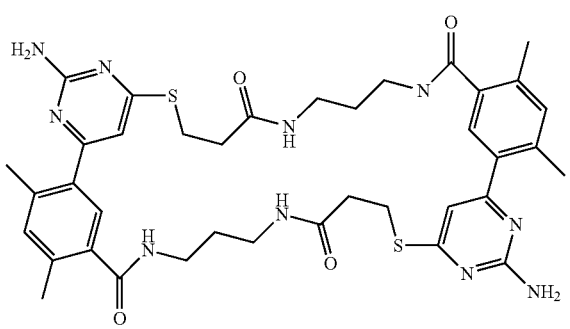

Dimer (Linear Form)

LCMS: ESI (m/z): calcd: 789.33, found: 789 [M+H]$^+$, eluted time: 4.6 min.

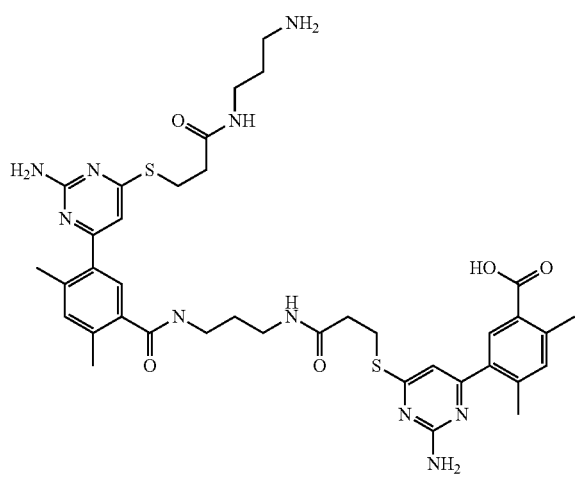

Results:

TABLE 5

• Results of reaction purity in Runs 1-5: HPLC Area % (230 nm)

|  | Cylization precursor | Target molecule | Dimer (cyclized form) | Dimer (linear form) |
|---|---|---|---|---|
| Run 1 | N.D. | 93.229 | 5.754 | N.D. |
| Run 2 | N.D. | 90.057 | 5.100 | N.D. |
| Run 3 | N.D. | 95.706 | 3.336 | N.D. |
| Run 4, after reaction | N.D. | 94.241 | 5.400 | N.D. |
| Run 5, 495 min (1.5θ) | 0.353 | 96.429 | 3.107 | N.D. |

TABLE 6

• Time course of reaction purity in Run 4: HPLC Area % (230 nm)

| Time after starting operation | Cyclization precursor | Target molecule | Dimer (Cyclized form) | Dimer (Linear form) |
|---|---|---|---|---|
| 165 minutes (θ) | 2.034 | 90.737 | 6.211 | N.D. |
| 330 minutes(2θ) | 1.501 | 91.792 | 5.961 | N.D. |
| 495 minutes(3θ) | 1.329 | 92.564 | 5.451 | N.D. |
| 660 minutes(4θ) | 1.231 | 92.786 | 5.573 | N.D. |
| After reaction | N.D. | 94.241 | 5.400 | N.D. |

TABLE 7

• Time course of reaction purity in Run 5: HPLC Area % (230 nm)

| Time after starting opeartion | Cyclization precursor | Target molecule | Dimer (Cyclized form) | Dimer (Linear form) |
|---|---|---|---|---|
| 165 minnutes(0.5θ) | 1.567 | 94.288 | 3.815 | N.D. |
| 330 minnutes(θ) | 0.650 | 95.872 | 3.352 | N.D. |
| 495 minutes(1.5θ) | 0.353 | 96.429 | 3.107 | N.D. |

TABLE 8

• Comparison between simulation and experimental result (Run 3)

| | Run 3 | |
|---|---|---|
| | Simulation | Experimental result |
| Selectivity * | 0.98 | 0.97 |

Simulation and experimental results were confirmed to be roughly in agreement in Run 3.

TABLE 9

• Comparison between simulation and experimental results (Runs 4, 5)

| | Run 4 (4θ) | | Run 5 (1.5θ) | |
|---|---|---|---|---|
| | Simulation | Experimental result | Simulation | Experimental result |
| Reaction conversion rate* | 0.99 | 0.99 | 0.99 | 1.00 |
| Selectivity * | 0.96 | 0.94 | 0.98 | 0.97 |

Simulation and experimental results were confirmed to be roughly in agreement in Runs 4 and 5.

Calculation Formulae

Reaction Conversion Rate

Simulation: (Initial concentration of cyclization precursor−Cyclization precursor concentration)/Initial concentration of cyclization precursor Experimental results: (Initial Area % of cyclization precursor−Area % of cyclization precursor)/Initial Area % of cyclization precursor Selectivity Simulation: Concentration of target molecule/(Concentration of target molecule+Concentration of dimer(linear+cyclic))

Experimental result: Area % of target molecule/(Area % of target molecule+Area % of dimer (linear+cyclic))

In Runs 4 and 5, the Area % of the dimer due to side reaction decreased and the Area % of the target cyclized form increased, compared to those at high-dilution in Runs 1-2. More specifically, utilization of a CSTR yielded high selectivity, and selectivity equivalent to or higher than that at Batch pseudo high-dilution in Run 3 could be achieved (Table 5).

Figure 2:
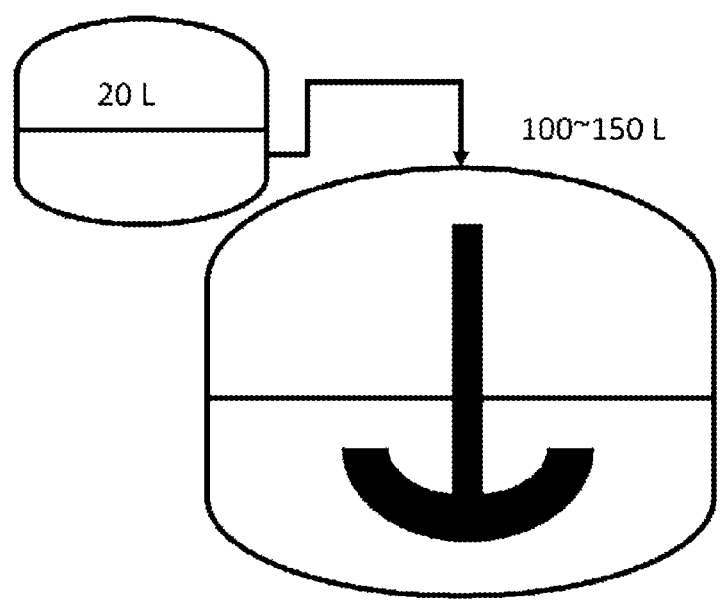
FIG. 2 presents assumed equipment for synthesizing 2 kg of the target molecule by pseudo high-dilution (the condition of Run 3 in Example 1).

Use of a CSTR enables production with equipment smaller than that for batch reactions. FIGS. 1 and 2 show comparison of the sizes of equipment used when performing the reaction using a CSTR and when performing the Pseudo high-dilution batch reactions by reverse dropwise addition of the raw materials, when assuming producing approximately 2 kg of product. In this case, the effective working day to obtain 2 kg of target molecule is one day in both cases; however, the equipment, particularly the size of the reaction tank can be reduced by approximately 20-fold. Furthermore, use of a CSTR(s) enables the operation to be carried out continuously, and improvement of efficiency of the operation, including the subsequent treatments, can be expected.

Example 2 Synthesis of Cyclosporin A

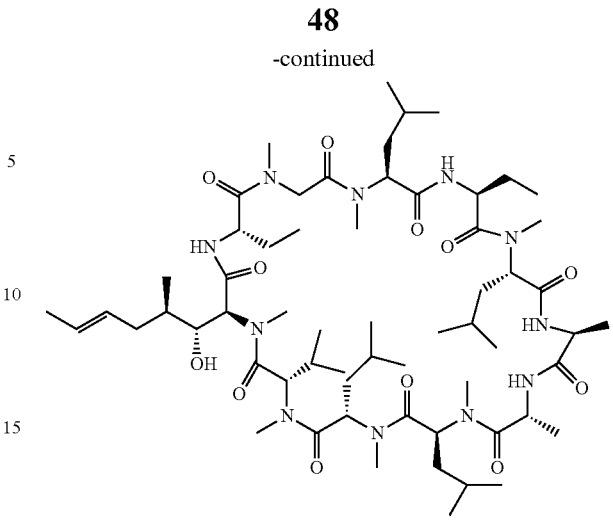

Protocol:

Synthesis of Cyclization Precursor

Following a non-patent literature (Bernard Riss, Arnaud Grandeury, Thorsten Gut, Manuela Seeger-Weibel, Christian Zuercher, Jinjing Li, and Fabrice Gallou. Org. Process Res. Dev. 2014, 18, 1763-1770), 165.2 g of the Ring-opened form 1 was synthesized from 198.3 g of Cyclosporin A.

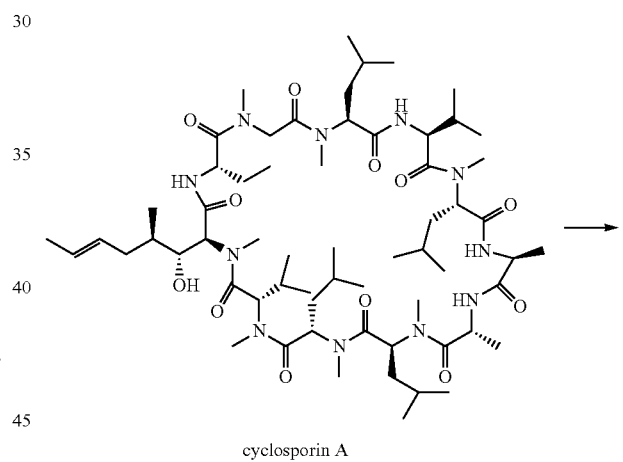

cyclosporin A

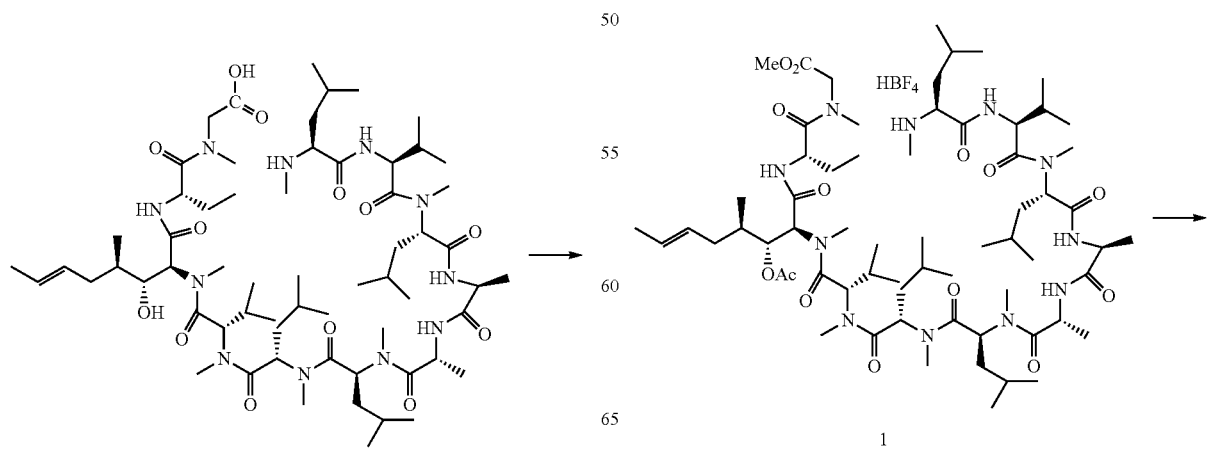

1

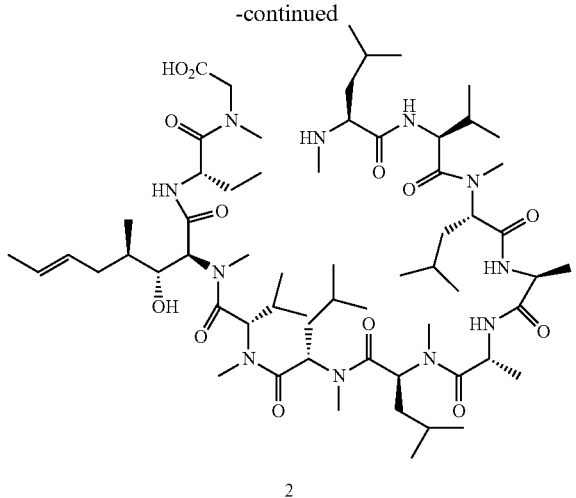

2

The aforementioned Ring-opened form 1 (10.0 g) was dissolved in methanol (300 mL), a solution of sodium methoxide in methanol (28% w/w, 5.7 g) was added to the obtained solution, and this was allowed to react. After stirring at room temperature for 14 hours, 1 M aqueous sodium hydroxide solution (37 mL) was added, and this was allowed to react further at room temperature for four hours. Next, 1 M potassium hydrogen sulfate solution was added to the reaction solution at an ice-cold temperature for neutralization so that its pH became approximately 7. The precipitated solid was filtered, and the filtrate was extracted twice with ethyl acetate (200 mL). The organic layer was then washed with water, and concentrated using an evaporator to obtain the Cyclization precursor 2 (8.1 g) as a white powder.

Reaction Rate Parameter Simulation

Data on change in concentration of each compound depending on the temperature/reaction time of each compound were collected at 5° C., 21° C., or −9° C. to calculate the reaction rate parameters. The concentration data at 5° C. and 21° C. were collected using a Plug flow reactor. More specifically, a solution of the cyclization precursor (3 mM) and DIPEA (16 mM) in DMF (Solution A), and an 8 mM solution of O-(7-azabenzotriazol-1-yl)-1,1,3,3-tetramethyl-uronium hexafluorophosphate (HATU) in DMF (Solution B) were reacted at 5° C. or 21° C. The reaction was quenched using a methylamine solution. The reaction time was adjusted by the flow rate of Solutions A and B. On the other hand, the data at −9° C. was collected using a Batch reactor. More specifically, a reaction solution produced by dissolving the cyclization precursor (35.0 mg, 74% content, 0.02 mmol) in DMF (14.3 mL), and adding DIPEA (20 mL, 5.4 equiv.) and HATU (22.3 mg, 2.8 equiv.) to it, was sampled over time. The cyclization precursor was detected as methyl amide.

The compound concentrations shown in Table 10 were calculated from HPLC data based on values of HPLC assays on the cyclization precursor and Cyclosporin A. The cyclization precursor was detected as the methyl amide form of the cyclization precursor, and their absorption coefficients were regarded as being equivalent. Furthermore, the absorption coefficients of Cyclosporin A and the dimer (cyclized form) were regarded as being equivalent.

TABLE 10

Data on change in compound concentration (Example 2)

| Temperature °C. | Reaction time (sec) | Cyclization precursor (mM) | Cyclospoin A (mM) | Dimer (cyclized form) (mM) |
|---|---|---|---|---|
| −9 | 60 | 1.12 | 0.18 | 0.09 |
| −9 | 120 | 0.80 | 0.32 | 0.24 |
| −9 | 240 | 0.46 | 0.52 | 0.43 |
| 5 | 32 | 1.03 | 0.25 | 0.11 |
| 5 | 64 | 0.59 | 0.43 | 0.24 |
| 5 | 128 | 0.33 | 0.65 | 0.37 |
| 21 | 32 | 0.70 | 0.52 | 0.16 |
| 21 | 64 | 0.42 | 0.74 | 0.26 |
| 21 | 128 | 0.15 | 0.96 | 0.32 |

From the obtained data, the present cyclization reaction mechanism was considered to be the following. Great effect of activator on the reaction rate was not observed; therefore, it was omitted.

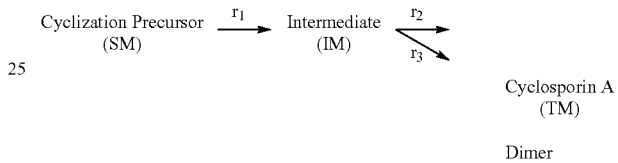

Using data on change in concentration over time and data on temperature obtained by the experiment (Table 10), the reaction rate constants k1, k2, and k3 at each temperature (−9° C., 5° C., and 21° C.) for each elementary reaction were obtained. The following equations were used to calculate the reaction rate constants k1, k2, and k3:

$$\frac{dC_{SM-HATU}}{dt} = k_1 C_{SM} - k_2 C_{SM-HATU} - 2k_3 C_{SM-HATU}^2$$

$$\frac{dC_{TM}}{dt} = k_2 C_{SM-HATU}$$

$$\frac{dC_{Dimer}}{dt} = k_3 C_{SM-HATU}^2$$

TM: Cyclosporin A; SM: cyclization precursor; SM-HATU: active intermediate; Dimer: dimer; C: concentration (M); k: reaction rate constant From the resulting reaction rate constants k1, k2, and k3 at each temperature and the temperature, frequency factor (A) and activation energy (E) for each elementary reaction were calculated from the Arrhenius plot. Microsoft Excel was used for the calculation.

As a result, the data shown in Table 11 were obtained.

TABLE 11

Frequency factor (A) and activation energy (E) corresponding to reaction rate constants k1, k2, k3

|  | A | E[J/mol] |
|---|---|---|
| k1 | 4.62E+3 [1/sec] | 24558 |
| k2 | 7.56E+4 [1/sec] | 37403 |
| k3 | 8.94E+4 [L/mol/sec] | 23673 |

The obtained frequency factor (A) and activation energy (E) for each elementary reaction were substituted into the Arrhenius' equation below, and by using the aforementioned reaction rate equations, reaction rate constants k1, k2, and k3 were calculated for the case in which the temperature for performing the cyclization reaction in a CSTR was set to 25° C. (Table 12).

$$k_n = A_n \exp\left(\frac{-E_n}{RT}\right)$$

TABLE 12

Reaction rate constants k1, k2, k3 for performing cyclization reaction in CSTR

| Temperature | k1 | k2 | k3 |
|---|---|---|---|
| 25° C. | 2.30E−01 | 2.12E−02 | 6.36E+00 |

Next, the reaction conversion rate, selectivity, and residence time when the cyclization precursor concentration is set to 0.04 mol/L and the reaction temperature is set to 25° C. were calculated using the reaction rate constants k1, k2, and k3 of Table 12, the following mass balance equations and the reaction rate equations (Table 13).

$$\tau = \frac{C_{0,n} - C_n}{-r_n}$$

$$\frac{dC_{SM-HATU}}{dt} = k_1 C_{SM} - k_2 C_{SM-HATU} - 2k_3 C_{SM-HATU}^2$$

$$\frac{dC_{TM}}{dt} = k_2 C_{SM-HATU}$$

$$\frac{dC_{Dimer}}{dt} = k_3 C_{SM-HATU}^2$$

TABLE 13

Calculated reaction condition (when cyclization precursor concentration is 0.04 mmol/L, reaction temperature is 25° C.)

| | Reaction conversion rate * | Selectivity * | Residence time [θ, min] |
|---|---|---|---|
| Case 1 | 0.99 | 0.94 | 80 |
| Case 2 | 0.99 | 0.97 | 160 |

* Calculation formulae
Reaction conversion rate: (Initial concentration of cyclization precursor − Cyclization precursor concentration)/Initial concentration of cyclization precursor
Selectivity: Cyclosporin A concentration/(Cyclosporin A + Dimer (cyclized form) concentration)

In Cases 1 and 2 of Table 13, residence time that will yield results in which the reaction conversion rate and selectivity became high were determined by calculation. In the present Example, Case 2 (Run 3) was performed.

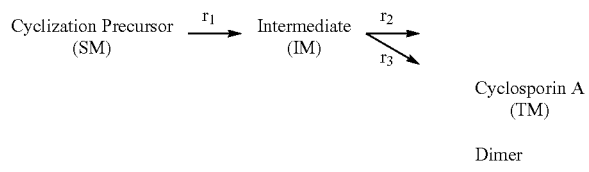

Run 1: Batch High-Dilution

HATU (18.9 mg, 2.7 equiv.) was added to a solution of the precursor compound (30.0 mg, 74% content, 0.02 mmol) and DIPEA (17 μL, 5.4 equiv.) in DMF (12.3 mL), and this was allowed to react for one hour. When the solution concentration of Cyclosporin A in the reaction solution was quantified to calculate the yield, it corresponded to 15.8 mg (72% yield).

Run 2: Batch Pseudo High-Dilution

To a solution of HATU (311.9 mg, 2.7 equiv.) and DMF (10 mL), a solution of the precursor compound (500.5 mg, 74% content, 0.30 mmol) and DIPEA (0.3 mL, 5.7 equiv.) in DMF (4.7 mL) was added dropwise over a period of 180 minutes. Approximately 60 minutes later, when the solution concentration of Cyclosporin A in the reaction solution was quantified to calculate the yield, it corresponded to 348.3 mg (95% yield).

Run 3: CSTR

The cyclization precursor (1.9009 g, 74% content, 1.15 mmol) and DIPEA (1.1 mL, 5.5 eqiv.) were dissolved in DMF (27.4 mL). The substrate concentration was 0.04 mmol/mL. On the other hand, HATU (1.1904 g, 2.7 equiv.) was dissolved in DMF (28.5 mL). The reagent concentration was 0.11 mmol/mL. These solutions were added to 12.8 mL of a DMF solvent at 25° C. respectively at an input speed of 0.04 mL/min, and the reaction solutions were drawn out at the same time at an output speed of 0.08 mL/min. Sampling was performed by collecting the reaction solution at 160 minutes (1θ), 320 minutes (2θ), 480 minutes (3θ), and 640 minutes (4θ) after starting the operation, and these samples were quenched using a dimethylamine solution. All of the output solutions and the solution inside the reactor were put together 640 minutes later, and when the concentration was quantified to calculate the yield, it corresponded to 1.14 g (98% yield).

Operation time 2θ or thereafter in Run 3, improvement in the purity of target molecule was observed compared to that of the Pseudo high-dilution method in Run 2.

Under the conditions of Run 3, producing 2 kg in one day is possible using a 7-L reaction tank (same as in Example 1, FIG. 1).

Analysis Conditions:
Column: BIOshell C18, 2.1 mm I.D.×150 mm L, 2.6 μm
Column temperature: 60° C.
Flow rate: 0.5 mL/min
Gradient (B %): 0 to 40.0 min (30→100), 40.0 to 40.6 min (100), 40.6 to 40.7 min (100→30), 40.7 to 45.0 min (30).

Cyclization Precursor:
LCMS (m/z) [M+H]⁺: calcd 1220.8598, found: 1220.8674; eluted time: 11.3 minutes. When tracing the reaction, the cyclization precursor was detected as a methylamide form present after quenching. Eluted time: 11.7 minutes.

Figure 3:
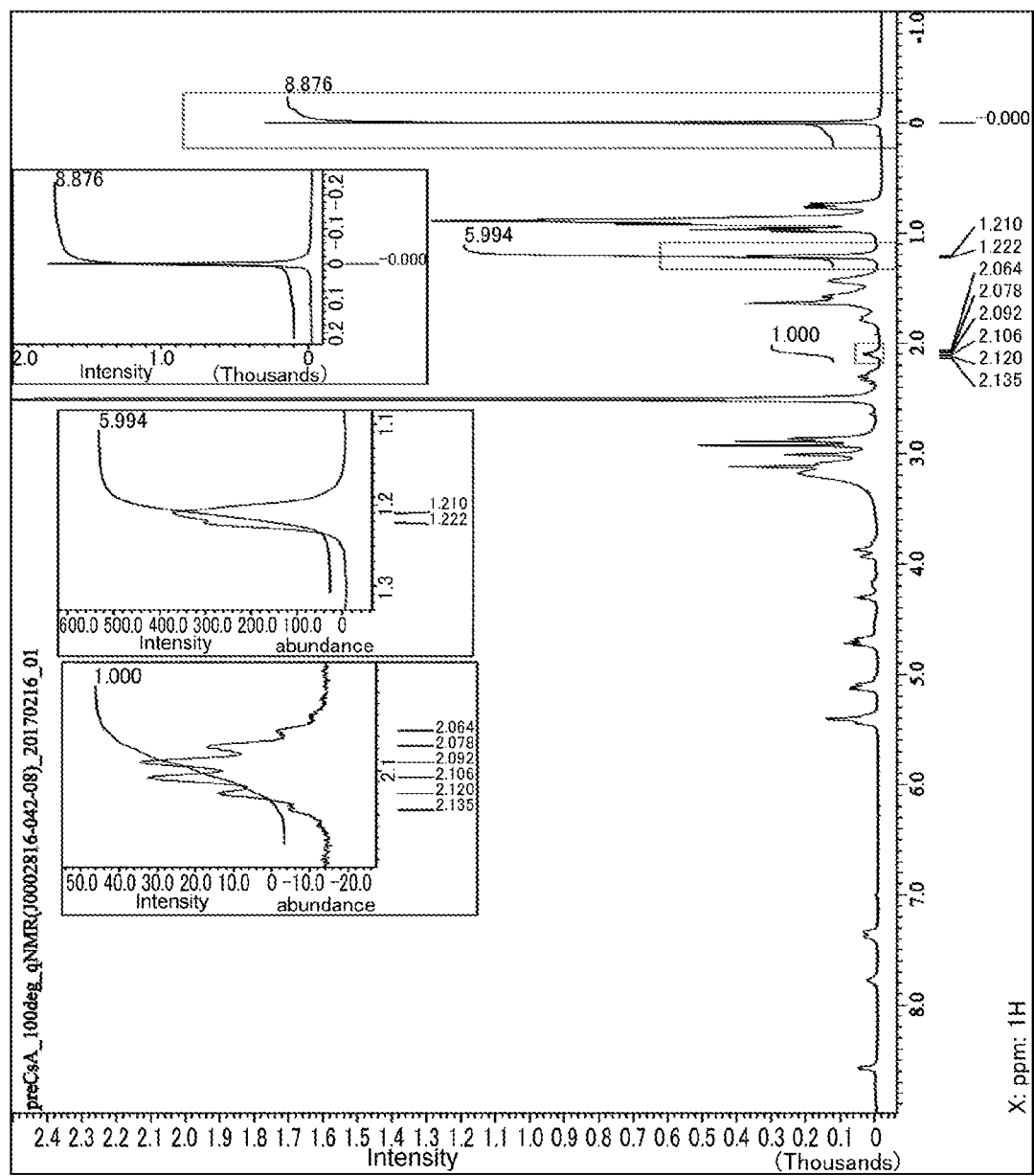
FIG. 3 shows a 1H NMR chart of a sample of a Cyclosporin A cyclization precursor (Example 2).
Figure 4:
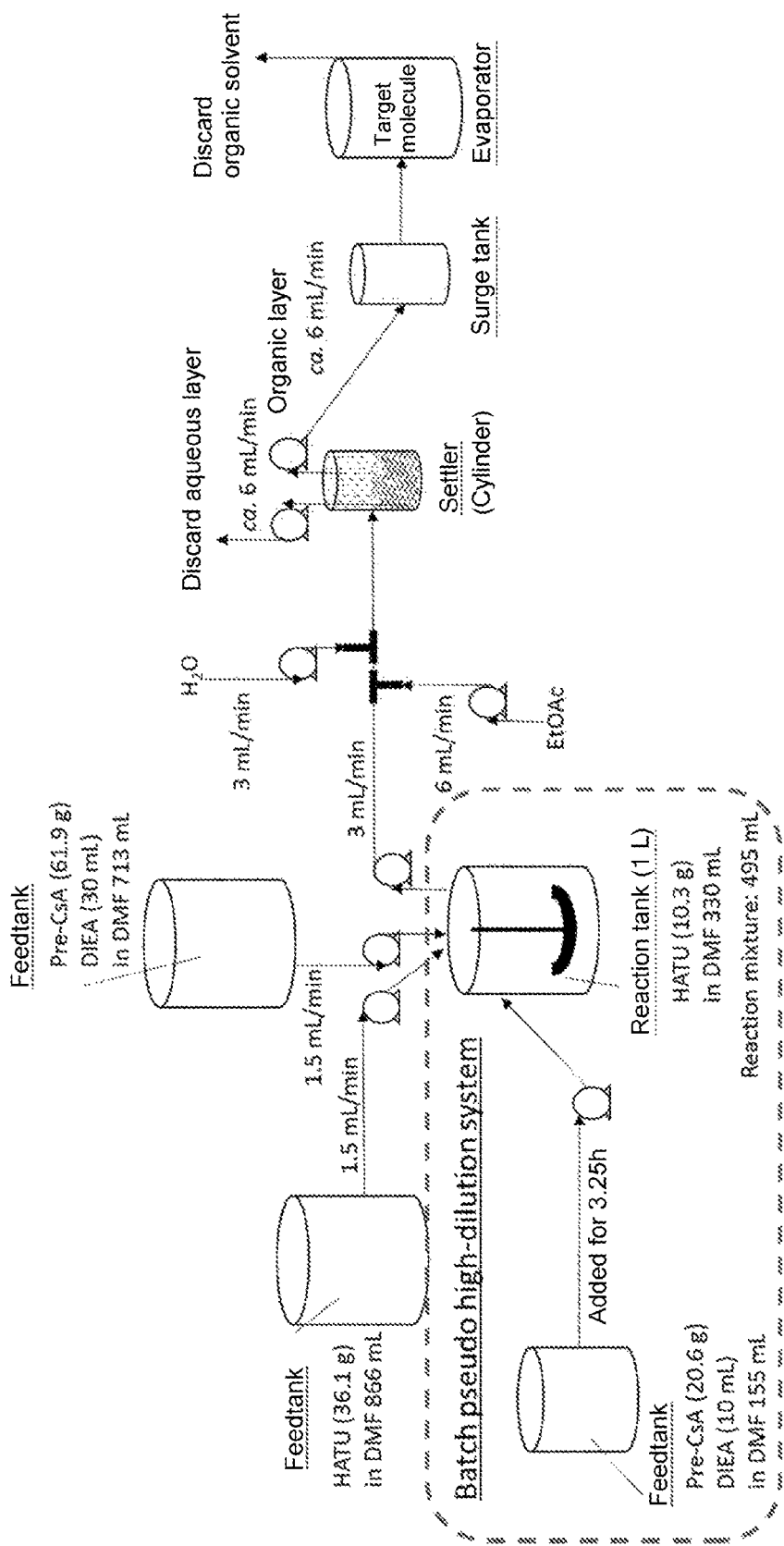
FIG. 4 presents the equipment for the production of Cyclosporin A using a CSTR in Example 3.
Figure 5:
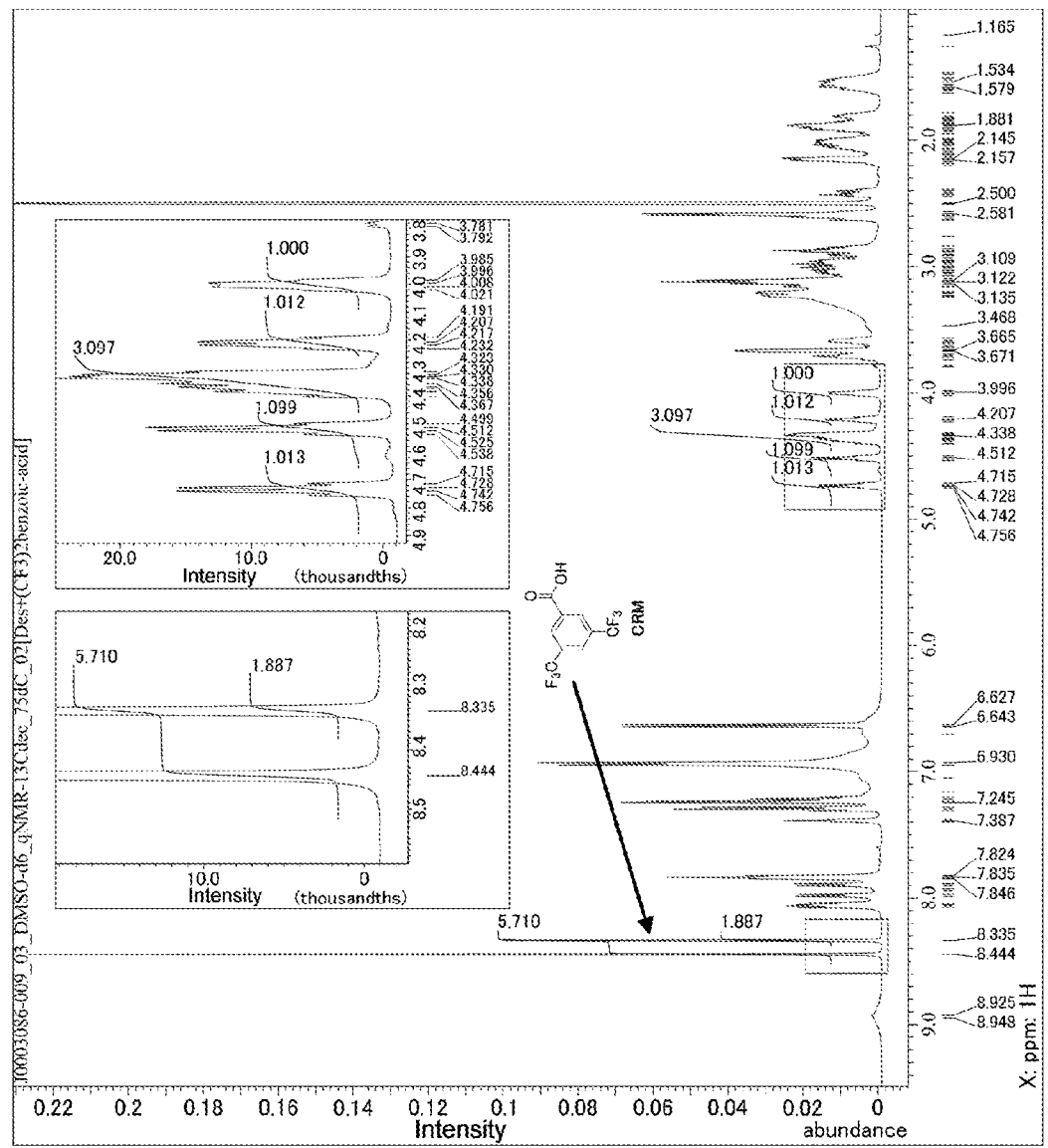
FIG. 5 shows a 1H NMR chart of a Desmopressin sample (Example 4).
Figure 6:
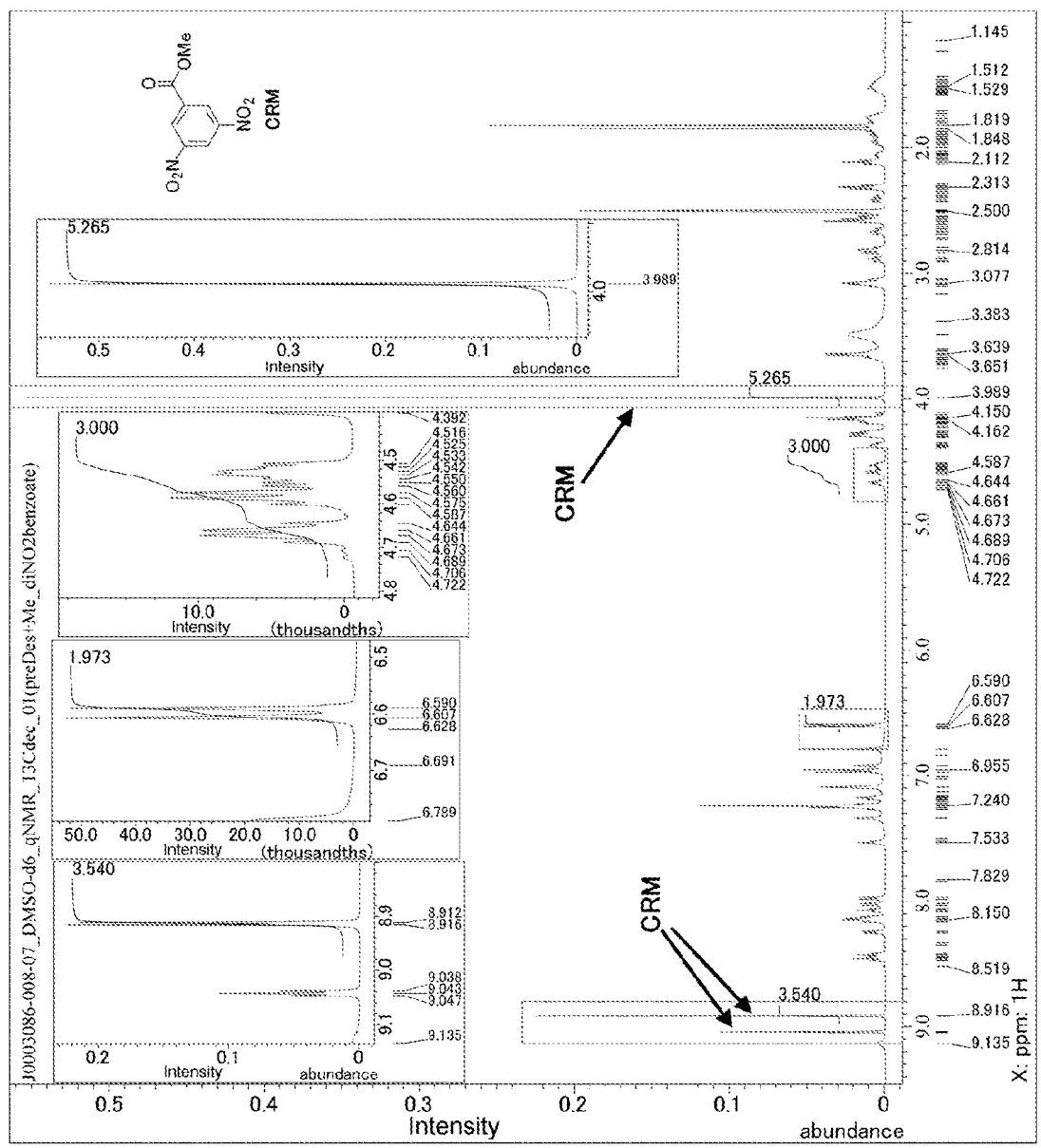
FIG. 6 shows a 1H NMR chart of a cyclization precursor sample of Desmopressin (Example 4).
Figure 7:
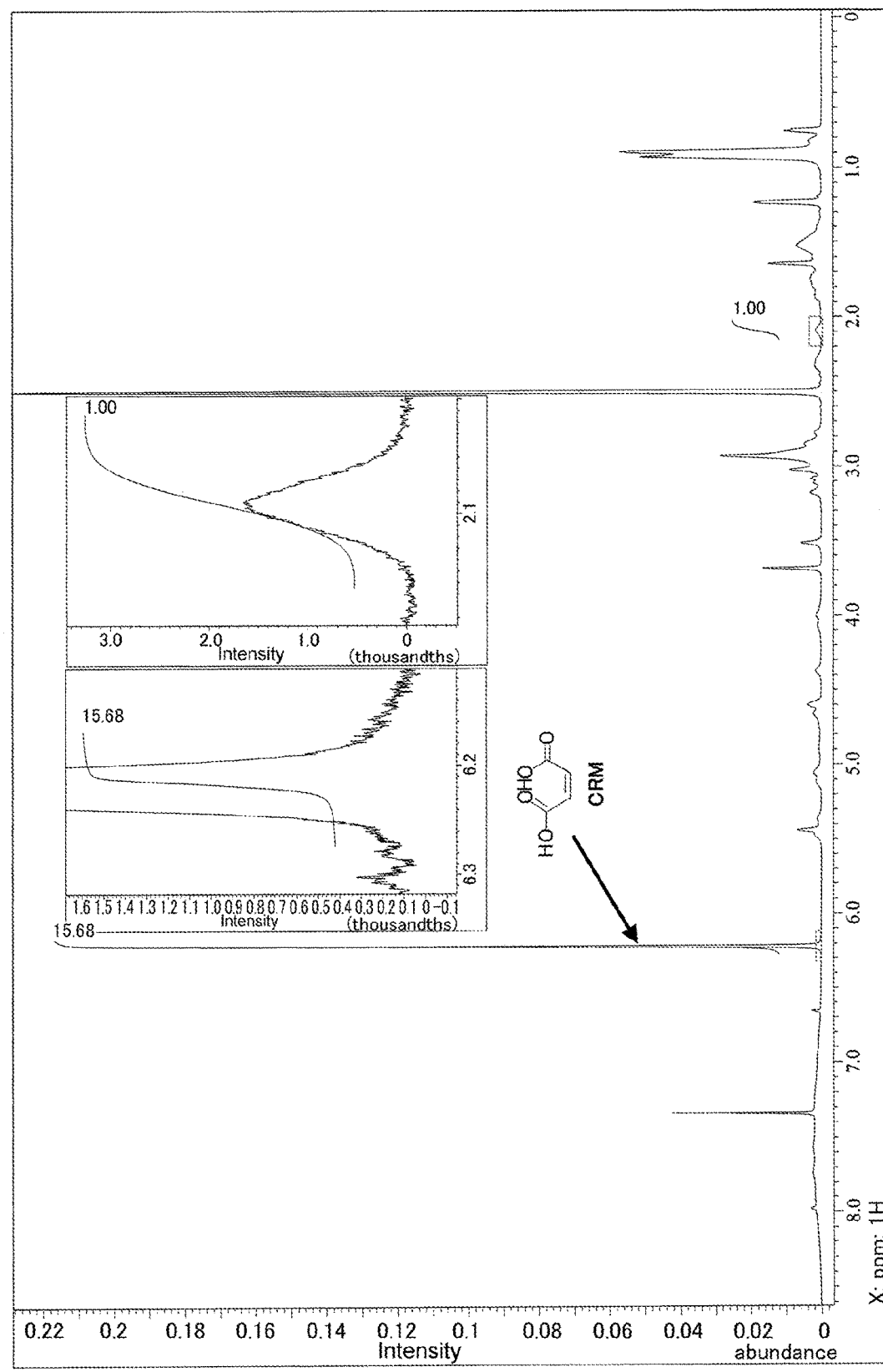
FIG. 7 shows a 1H NMR chart of a sample of a Cyclosporin A derivative (Example 5).
Figure 8:
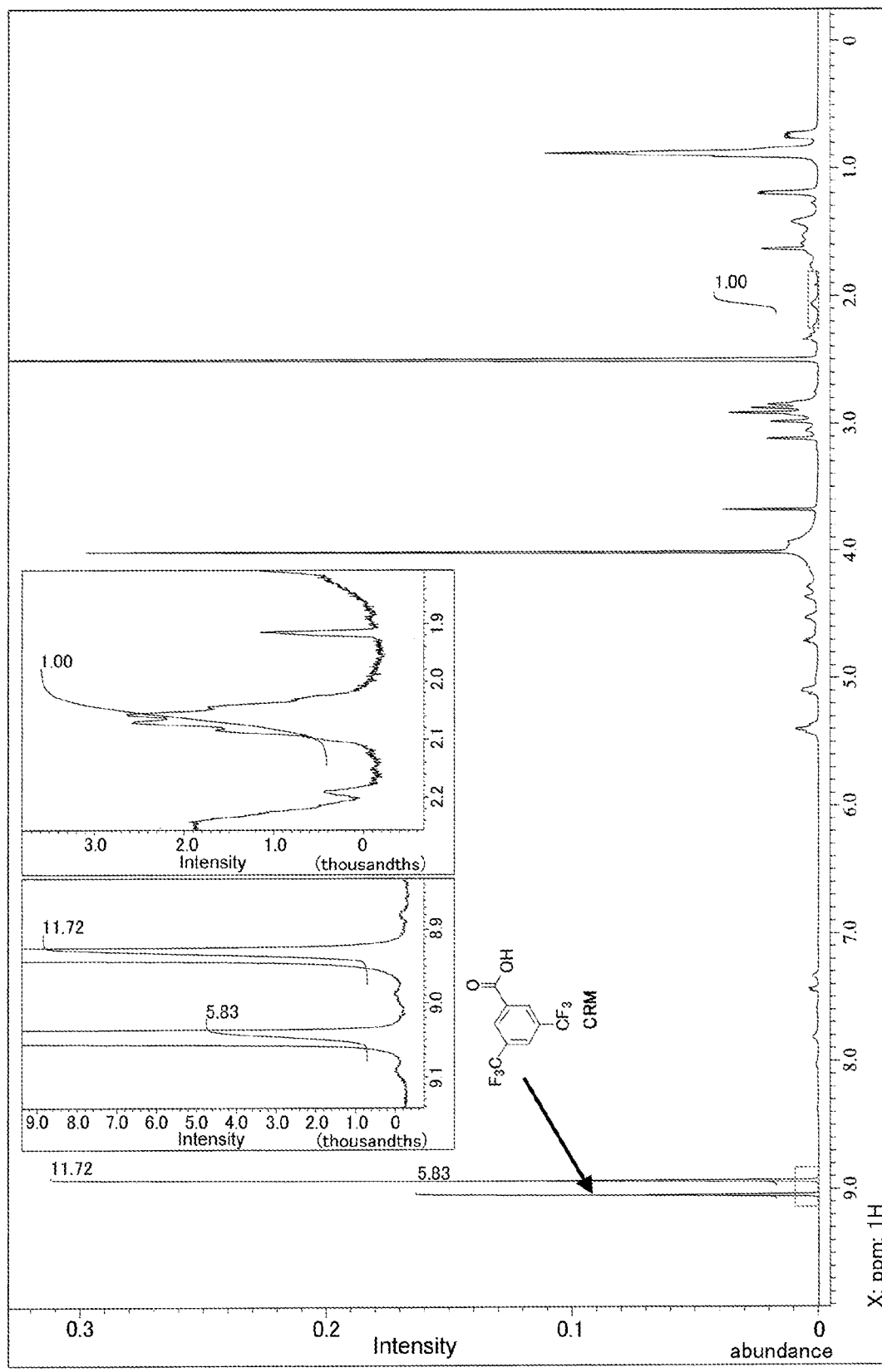
FIG. 8 shows a 1H NMR chart of a cyclization precursor sample of a Cyclosporin A derivative (Example 5).

Assay: determined to be 74% from qNMR and HPLC assay
  a. Sample qNMR:
    Measurement conditions: DMSO-d6, 100° C., pulse angle: 90°, digital resolution: 0.15, relaxation time: 60 seconds, no spin, accumulation number: 64 times
    1H NMR peak assignment (see FIG. 3): (Me of two Ala, six H in total), (iPrCH of NH-Val, one H) identified by COSY and TOCSY.
    Internal standard: sodium 3-(trimethylsilyl)-1-propane-1,1,2,2,3,3-d6-sulfonate    Content: 81.2% b. Result of performing an HPLC assay using a raw material used in the present Example as a sample: 91.7%
¹H NMR (CDCl₃): Identical to the information in the following literature: Kessler et al., Helvetica Chimica Acta, 1985, 68, 661.
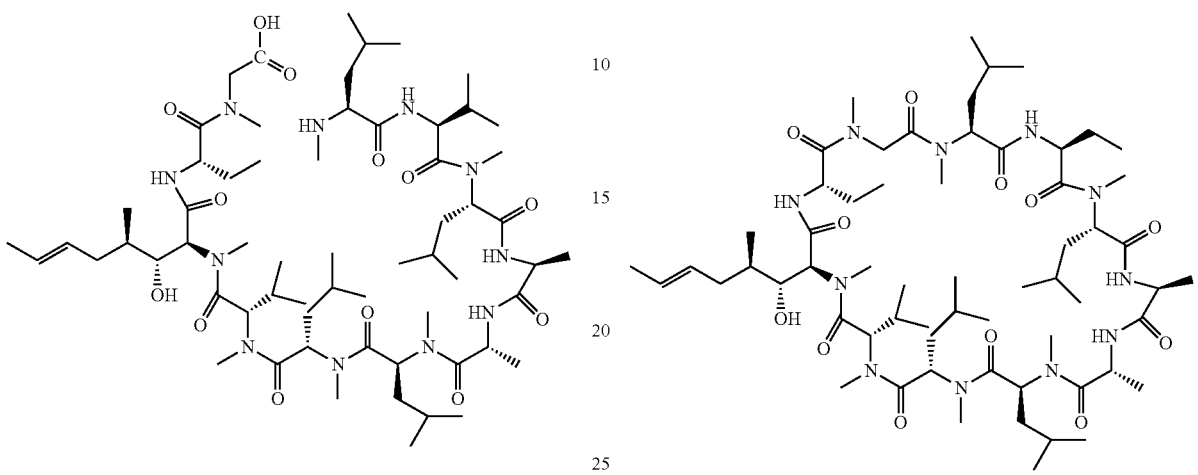
Cyclosporin A:
LCMS: m/z [M+H]⁺: calcd 1202.8492, found: 1202.8589; eluted time: 21.5 minutes.
Dimer (cyclized): m/z [M+2H]²⁺: calcd: 1203.3509, found: 1203.3517; eluted time: 29.1 minutes.
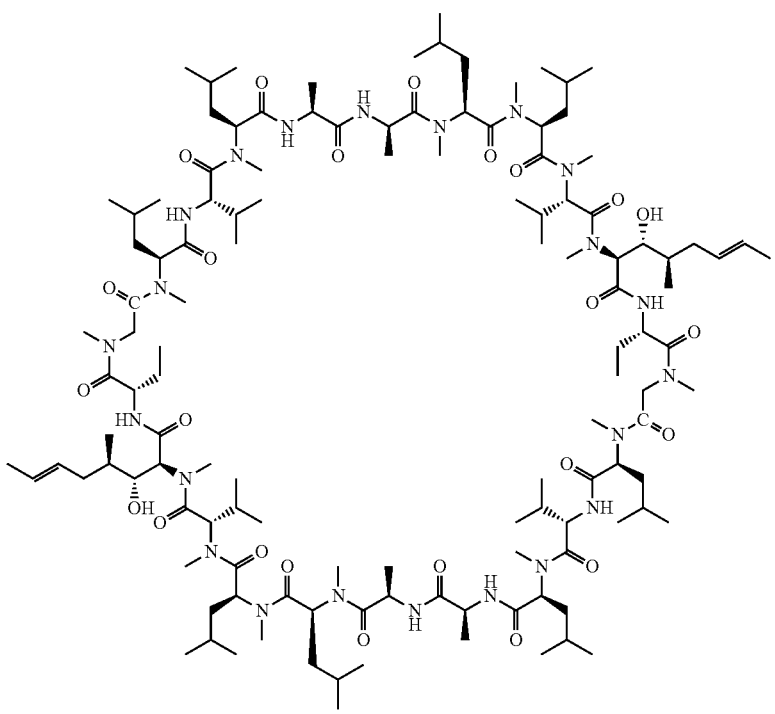 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N(C)[C@@H]([C@H](O)[C@H](C)C/C=C/C)C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Impurity with β-elimination: LCMS: m/z [M+H]⁺: calc. 1202.8492, found: 1202.8587; eluted time: 12.6 minutes.

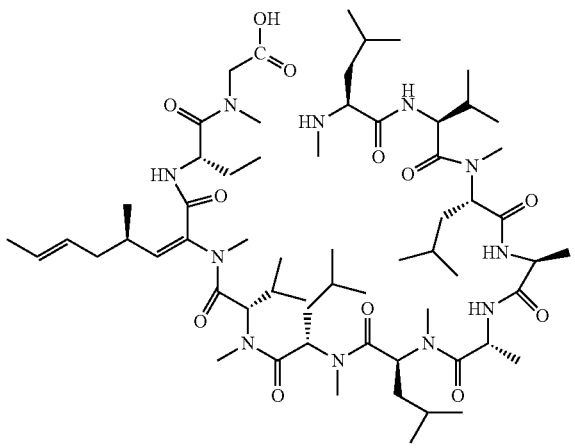 [SMILES: C/C=C/C[C@@H](C)/C=C(\C(=O)N[C@@H](CC)C(=O)N(C)CC(=O)O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H](CC(C)C)NC)C(C)C]

Impurity with β-elimination (cyclized form): LCMS (m/z) [M+H]⁺: calcd. 1184.8386, found: 1184.8448; eluted time: 22.0 minutes.

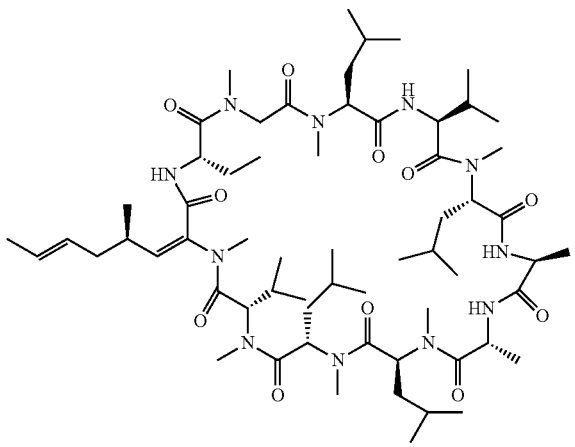 [SMILES: C/C=C/C[C@@H](C)/C=C1\C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Results:

TABLE 14

Result of reaction purity in Run 1: HPLC Area %* (205 nm)

| Reaction time | Cyclization precursor | Cyclosporin A | Dimer (cyclized form) | Impurity with β-elimination (cyclized form) |
|---|---|---|---|---|
| 1 hour | 0.44 | 73.12 | 19.84 | 6.60 |

*Calculations were performed by defining sum of the cyclization precursor, Cyclosporin A, dimer (cyclized form), and the impurity with β-elimination (cyclized form) as 100%.

Calculations for Runs 2 and 3 were performed similarly.

TABLE 15

Time course of reaction purity in Run 2: HPLC Area % (205 nm)

| Reaction time | Cyclization precursor | Cyclosporin A | Dimer (Cyclized) | Impurity with β-elimination (cyclized form) |
|---|---|---|---|---|
| 180 minutes after dropwise addition | 0.54 | 85.10 | 6.51 | 7.85 |
| 30 minutes after reaction | 0.54 | 85.28 | 6.52 | 7.67 |

TABLE 16

Time course of reaction purity in Run 3: HPLC Area % (205 nm)

| Time after stalling reaction | Cyclization precursor | Cyclosporin A | Dimer (cyclized) | Impurity with β-elimination (cyclized form) |
|---|---|---|---|---|
| 160 minutes (θ) | 0.94 | 86.16 | 5.30 | 7.60 |
| 320 minutes (2θ) | 0.59 | 86.27 | 5.41 | 7.74 |
| 480 minutes (3θ) | 0.62 | 86.61 | 5.51 | 7.26 |
| 640 minutes (4θ) | 0.29 | 87.12 | 4.99 | 7.60 |
| After reaction | 0.06 | 87.14 | 4.94 | 7.85 |

TABLE 17

• Comparison between simulation and experimental result (Run 2)

| | Run 2: Batch pseudo high-dilution | |
|---|---|---|
| | Simulation | Experimental result |
| Selectivity * | 0.99 | 0.93 |

Simulation and experimental results were confirmed to be roughly in agreement in Run 2.

TABLE 18

• Comparison between simulation and experimental result (Run 3)

| | Run 3: CSTR | |
|---|---|---|
| | Simulation | Experimental result |
| Reaction conversion rate * | 0.99 | 0.99 |
| Selectivity * | 0.97 | 0.94 |

* Calculation formulae
Reaction conversion rate
Simulation: (Initial concentration of cyclization precursor − Cyclization precursor concentration)/Initial concentration of cyclization precursor
Experimental results: (Initial Area % of cyclization precursor − Area % of cyclization precursor)/Initial Area % of cyclization precursor
Selectivity
Simulation: Cyclosporin A concentration/(Cyclosporin A + Dimer (cyclized form) concentration)
Experimental results: Area % of Cyclosporin A/(Area % of Cyclosporin A + Area % of the Dimer (cyclized form))

Simulation and experimental results were confirmed to be roughly in agreement in Run 3.

In Run 3 (Table 16), the Area % of the dimer due to the side reaction decreased, and the Area % of the target cyclized form increased, compared to those at high-dilution in Run 1 (Table 14). More specifically, utilization of a CSTR yielded high selectivity, and selectivity equivalent to or higher than that at batch pseudo high-dilution in Run 2 (Table 15) could be achieved.

Example 3 Production of Cyclosporin A

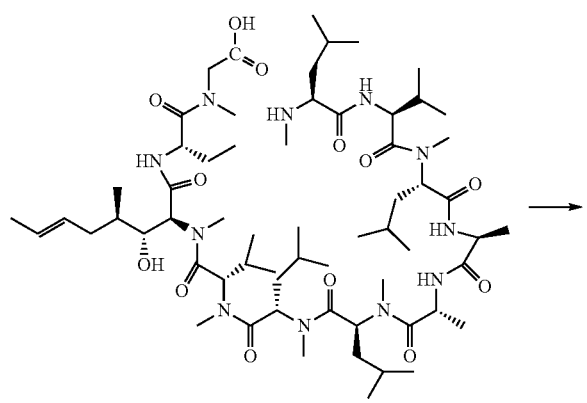

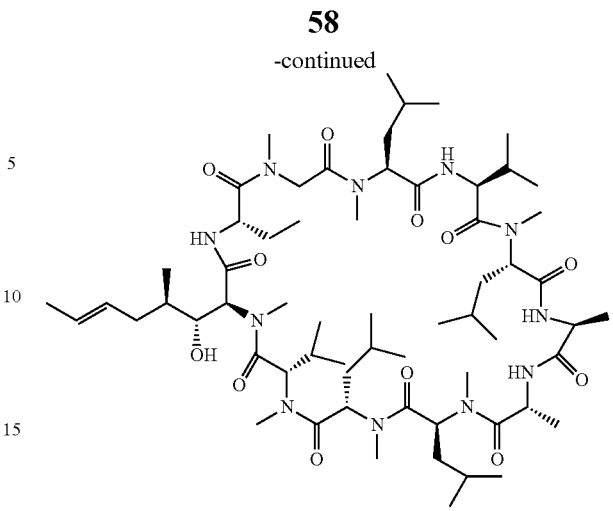

Reaction was scaled-up by reference to the data obtained in Example 2.

As described herein, a pseudo steady state was prepared in advance by Batch pseudo high-dilution, and a reaction using a CSTR was performed.

Batch Pseudo High-Dilution

When the precursor compound (20.6354 g, 59% content, 10 mmol) was dissolved in DMF (155 mL), insoluble material was observed. Then, the insoluble material was filtered and after confirming that the precursor compound was not included in the solid, a cyclization precursor solution was prepared by adding DIPEA (10 mL, 5.7 equiv.) to the filtrate. To a solution of HATU (10.2745 g, 2.7 equiv.) and DMF (330 mL) prepared in advance in a 1-L reaction tank, the cyclization precursor solution was added dropwise over a period of 195 minutes, and the obtained preparation solution was stored at room temperature for one day.

CSTR

A reaction substrate solution was prepared by mixing the cyclization precursor (61.902 g, 59% content, 30 mmol) and DMF (713 mL), removing the insoluble material, and then adding DIPEA (30 mL, 5.7 equiv.). The substrate concentration was 0.04 mmol/mL. A reaction reagent solution was prepared by dissolving HATU (36.145 g) in DMF (866 mL). The reagent concentration was 0.11 mmol/mL. The reaction substrate solution and the reaction reagent solution were added respectively at an input speed of 1.5 mL/min to the preparation solution prepared by Batch pseudo high-dilution, and the reaction solution was output at 3.0 mL/min at the same time.

Ethyl acetate was mixed into the output line at 6.0 mL/min using a T-tube, and then water was mixed at 3.0 mL/min using a T-mixer. The mixed solution was confirmed to have undergone interface separation in the cylinder, and the upper layer (organic phase) and the lower layer (aqueous phase) were respectively output at 5.5 mL/min to 6.5 mL/min. The output flow rate was adjusted so that the liquid separation interface will become constant.

The upper layer (organic phase) was temporarily stored in a surge tank, and when the volume reached approximately 400 mL, this was concentrated using an evaporator. The external temperature was 40° C. during the concentration operation, and the concentration operation was continued while adding the organic layer at a cycle time of 15 minutes to 20 minutes.

Input to the tank involved addition of the entire amount in 550 minutes. Post-processing (separation and concentration operations on the reaction solution, similar to those mentioned above) was performed in parallel with the reaction, and consequently, an additional 160-minute operation was needed. Finally, 439.86 g of a concentrated residue was obtained. As a result of performing an assay, the obtained cyclosporin corresponded to 44.2 g (92% yield).

Cyclization precursor: from qNMR and HPLC assays, the content was determined to be 59%.

Results:

TABLE 19

| Time course of reaction purity: HPLC Area % * (205 nm) | | | | |
|---|---|---|---|---|
| Time after stalling operation | Cyclization precursor | Cyclosporin A | Dimer (cyclized) | Impurity with β-elimination (cyclized form) |
| After Batch pseudo high-dilution reaction | 1.536 | 84.811 | 5.210 | 8.444 |
| After storage of reaction solution | 1.646 | 84.594 | 5.374 | 8.386 |
| 160 minutes (θ) | 0.671 | 85.834 | 5.278 | 8.217 |
| 320 minutes (2θ) | 0.411 | 86.261 | 5.044 | 8.284 |
| 480 minutes (3θ) | 0.215 | 86.847 | 4.607 | 8.330 |
| Concentrated residue | 0.375 | 86.609 | 4.862 | 8.154 |

Comparison Between Simulation and Experimental Results

TABLE 20

| | Batch pseudo high-dilution | | |
|---|---|---|---|
| | Simulation | Experimental result | Result of Example 2 |
| Selectivity * | 0.99 | 0.94 | 0.93 |

Results from Batch pseudo high-dilution were roughly the same as the results from Example 2.

TABLE 21

| | CSTR | | |
|---|---|---|---|
| | Simulation | Experimental result | Result of Example 2 |
| Reaction conversion rate * | 0.99 | 0.99 | 0.99 |
| Selectivity * | 0.97 | 0.95 | 0.94 |

* Calculation formulae
Reaction conversion rate
Simulation: (Initial concentration of cyclization precursor − Cyclization precursor concentration)/Initial concentration of cyclization precursor
Experimental results: (Initial Area % of cyclization precursor − Area % of cyclization precursor)/Initial Area % of cyclization precursor
Selectivity
Simulation: Cyclosporin A concentration/(Cyclosporin A + Dimer (cyclized form) concentration)
Experimental results: Area % of Cyclosporin A/(Area % of Cyclosporin A + Area % of the Dimer (cyclized form))

Simulation and the results from the experiment were confirmed to be roughly in agreement when using a CSTR. Furthermore, homology was higher than that in Example 2.

This time, by performing the reaction in a 1-L tank and post-processing in a continuous manner, 44.2 g of Cyclosporin A could be produced in 710 minutes (550 minutes for the reaction, and the remaining 160 minutes for the post-processing).

Example 4 Synthesis of Desmopressin

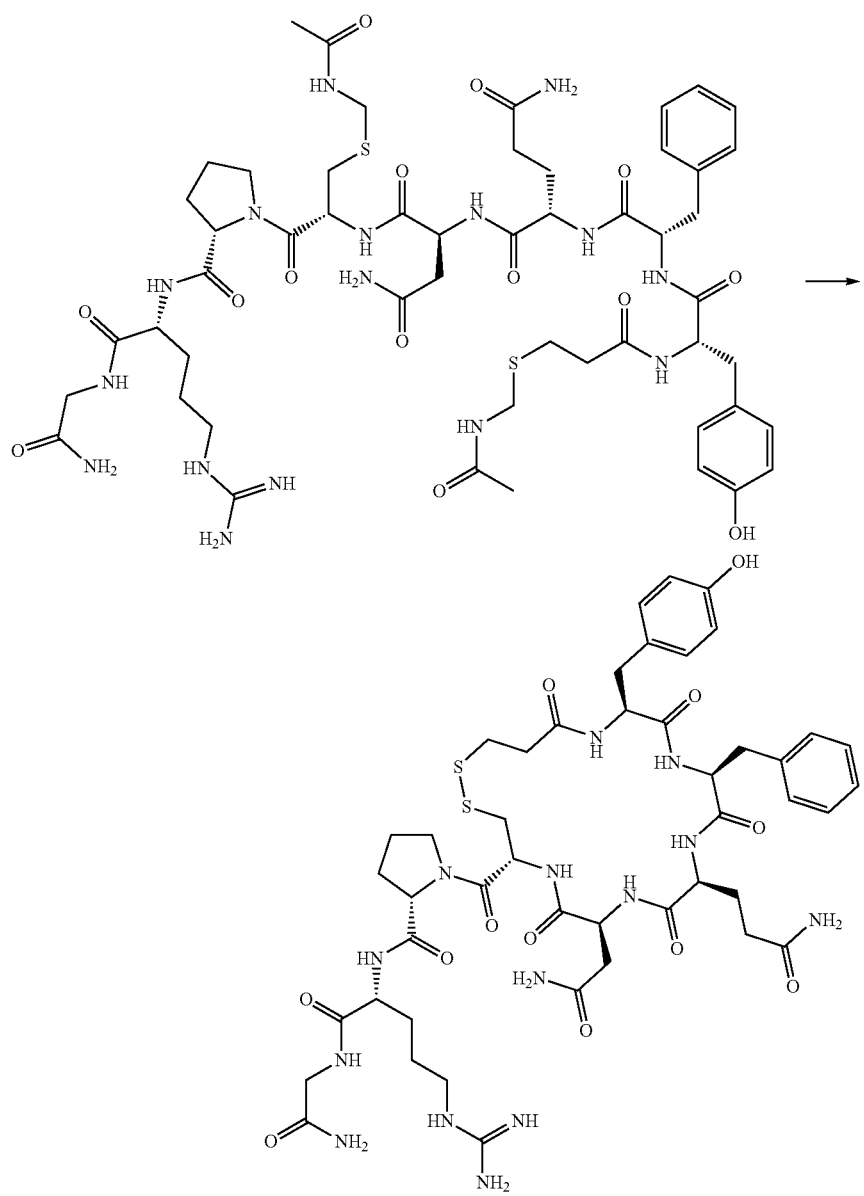

Protocol:

Reaction Rate Parameter Simulation

To calculate the reaction rate parameters, data on change in concentration of each compound depending on temperature/reaction time of each compound were collected. The cyclization precursor (8.92 mM) prepared in a 4:1 solution of N,N-dimethylformamide (DMF) and acetic acid (Solution A), and a 32 mM solution of iodine prepared in a 4:1 solution of DMF and acetic acid (Solution B) were reacted at 0° C., 23° C. or 40° C. The reaction was quenched using a 1% sodium dithionite solution. Plug flow reactor was used for the reaction, the reaction time was adjusted by the flow rate of Solutions A and B, and the data shown in Table 22 were obtained.

The compound concentrations were derived by assuming that the molar absorption coefficients of the cyclization precursor and the target molecule are the same, and converting the initial concentration of the cyclization precursor (4.46 mM as a reaction mixture solution of the above-mentioned experiment) to an HPLC Area %. Furthermore, the absorbance of the dimer was assumed to be twice that of the cyclization precursor, and the concentrations were calculated.

TABLE 22

Data on change in compound concentration (Example 4)

| Temperature ° C. | Reaction time (sec) | Cyclization precursor (mM) | Target molecule (mM) | Dimer (linear + cyclized form) (mM) |
|---|---|---|---|---|
| 0 | 2 | 3.29 | 1.11 | 0.03 |
| 0 | 10 | 2.63 | 1.67 | 0.08 |

TABLE 22-continued

Data on change in compound concentration (Example 4)

| Temperature ° C. | Reaction time (sec) | Cyclization precursor (mM) | Target molecule (mM) | Dimer (linear + cyclized form) (mM) |
|---|---|---|---|---|
| 0 | 40 | 0.90 | 3.30 | 0.13 |
| 23 | 2 | 3.22 | 1.22 | 0.03 |
| 23 | 10 | 1.97 | 2.33 | 0.08 |
| 23 | 40 | 0.31 | 3.93 | 0.11 |
| 40 | 2 | 2.99 | 1.40 | 0.04 |
| 40 | 10 | 1.62 | 2.66 | 0.09 |
| 40 | 40 | 0.28 | 3.97 | 0.11 |

From the obtained data, the mechanism of this cyclization reaction was considered to be the following. The reaction from the cyclization precursor to the iodide intermediate was considered to be fast; therefore, the reactions from the iodide intermediate to the target molecule and to the dimers (multiple compounds) was considered to be the rate-limiting steps. While the concentration of the iodide intermediate could not be measured, there may be no problem in assuming that the iodide intermediate concentration and the cyclization precursor concentration obtained by analysis are equivalent since the iodide intermediate may return to the cyclization precursor due to quenching before analysis, and also considering the aforementioned reaction rate difference. Therefore, each parameter was calculated using the elementary reactions shown in the formula below. Since iodine was used in excess amount with respect to the cyclization precursor and great effect of iodine on reaction rate was not observed, it was omitted in the reaction rate simulation.

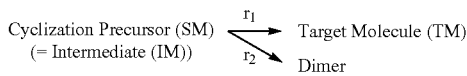

Using the data on concentration change over time and data on temperature obtained by the experiments (Table 22), the frequency factor (A) and activation energy (E) for each elementary reaction were determined using the equations below:

$$\frac{dC_{TM}}{dt} = k_1 C_{SM}$$

$$\frac{dC_{Dimer}}{dt} = k_2 C_{SM}^2$$

$$k_n = A_n \exp\left(\frac{-E_n}{RT}\right)$$

SM: cyclization precursor; TM: target molecule; Dimer: sum of linear and cyclic dimers; C: concentration (M); kn: reaction rate constant; An: frequency factor; En: activation energy; T: temperature; R: gas constant Aspen custom modeler from Aspen Technology was used for the calculations. As a result, the data shown in Table 23 were obtained.

TABLE 23

Frequency factor (A) and activation energy (E) corresponding to reaction rate constants k1 and k2

| | A | E [J/mol] |
|---|---|---|
| k1 | 36.4614 [1/sec] | 15004.3 |
| k2 | 13.3879 [L/mol/sec] | 4854.01 |

The reaction rate constants k1 and k2 when the temperature for carrying out the cyclization reaction in a CSTR is set to 25° C. were calculated from the obtained frequency factor (A) and activation energy (E) of each elementary reaction (Table 24).

TABLE 24

Reaction rate constants k1, k2 at 25° C. when performing cyclization reaction in CSTR

| Temperature | k1 | k2 |
|---|---|---|
| 25° C. | 8.57E−2 | 1.89 |

Next, the reaction conversion rate, selectivity, and residence time when the cyclization precursor concentration is set to 0.04 mol/L and the reaction temperature is set to 25° C. were calculated using the reaction rate constants k1 and k2 of Table 24, the following mass balance equation and the reaction rate equations (Table 25).

$$\tau = \frac{C_{0,n} - C_n}{-r_n}$$

$$\frac{dC_{TM}}{dt} = k_1 C_{SM}$$

$$\frac{dC_{Dimer}}{dt} = k_2 C_{SM}^2$$

TABLE 25

Calculated reaction condition (when cyclization precursor concentration is 0.04 mol/L, reaction temperature is 25° C.)

| | Reaction conversion rate* | Selectivity * | Residence time [θ, min] |
|---|---|---|---|
| Case 1 | 0.994 | 0.997 | 30 |
| Case 2 | 0.997 | 0.999 | 60 |
| Case 3 | 0.998 | 0.999 | 120 |

* Calculation formulae Reaction conversion rate: (Initial concentration of cyclization precursor-Cyclization precursor concentration)/Initial concentration of cyclization precursor
Selectivity: Concentration of target molecule/(Concentration of target molecule + Dimer (linear + cyclized) concentration)

In Cases 1 to 3 of Table 4, residence time that will yield results in which the reaction conversion rate and selectivity become high were determined by calculation. In the present Example, Case 2 (Run 3) was carried out.

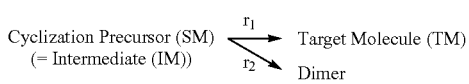

Run 1: Batch High-Dilution
Following a non-patent literature (Dominic Ormerod, Bart Noten, Matthieu Dorbec, Lars Andersson, Anita Buekenhoudt, and Ludwig Goetelen. Org. Process Res. Dev.

2015, 19, 841-848.), the cyclization precursor (200.8 mg, 86.2% content, 0.143 mmol) was dissolved with N,N-dimethylformamide (DMF) (4.4 mL) and acetic acid (1.6 mL), and a solution of iodine (4.4 equiv.) in DMF (solution volume: 2.5 mL) was added at room temperature to the mixture. The obtained mixture was allowed to react at room temperature for five minutes. After quenching the reaction solution using an aqueous sodium dithionite solution, the solution concentration of the target molecule was quantified, and when the yield was calculated, it corresponded to 121.6 mg (80% yield).

Run 2: Batch Pseudo High-Dilution

To a solution of iodine (0.3212 g, 3.5 equiv.), DMF (10 mL), and acetic acid (2.5 mL), a solution of the cyclization precursor compound (502.0 mg, 86.2% content, 0.357 mmol), DMF (6 mL), and acetic acid (1.5 mL) was added dropwise at 22° C. over a period of 60 minutes. Approximately 30 minutes after the dropwise addition, when the solution concentration of the target molecule was quantified to calculate the yield, it corresponded to 284.4 mg (75% yield).

Run 3: CSTR

The cyclization precursor (1.2040 g, 86.2% content, 0.855 mmol) was dissolved in DMF (19.2 mL) and acetic acid (4.8 mL). The substrate concentration was 0.04 mmol/mL. On the other hand, iodine (0.8497 g, 3.348 mmol) was dissolved in DMF (20.0 mL) and acetic acid (5.0 mL). The reagent concentration was 0.13 mmol/mL. These solutions were added to a DMF (9.6 mL)/acetic acid (2.4 mL) solution at 23° C. respectively at an input speed of 0.1 mL/min, and the reaction solutions were drawn out at the same time at an output speed of 0.2 mL/min. Sampling was performed by collecting the reaction solution at 60 minutes (θ*), 120 minutes (2θ), 180 minutes (3θ), and 240 minutes (4θ) after starting the operation, and these samples were quenched using a 0.05% sodium dithionite solution. When all of the output solutions obtained by inputting 97.3% of the prepared raw materials were put together, and the concentration was quantified to calculate the yield, it corresponded to 831.9 mg (93% yield).

*θ=elapsed time/average residence time

Analysis Conditions:

HPLC and LCMS conditions:

Column: Biochell C18, 2.1 mm I.D.×150 mmL, 2.6 μm

Mobile phase: A) water:TFA=2000:1; B) acetonitrile:TFA=2000:1

Column temperature: 60° C.

Flow rate: 0.5 mL/min

Gradient (B %): 0 to 20.0 min (5-45), 20.1 to 23.0 min (100), 23.1 min and thereafter (5).

MS detection mode: ESI (LC/MS): m/z

Target molecule (Desmopressin):

LCMS: ESI (m/z): 1069 [M+H]+; eluted time: 8.8 minutes

Sample qNMR (trifluoroacetate):

Measurement conditions: DMSO-d6, 75° C., pulse angle: 90°, digital resolution: 0.29 Hz, relaxation time: 30 seconds, no spin, accumulation number: 64 times CH proton of Gln (one H in total, δ: 3.985-4.021 ppm) was used for quantification Internal standard: 3,5-bis(trifluoromethyl)benzoic acid Content: 77.4%

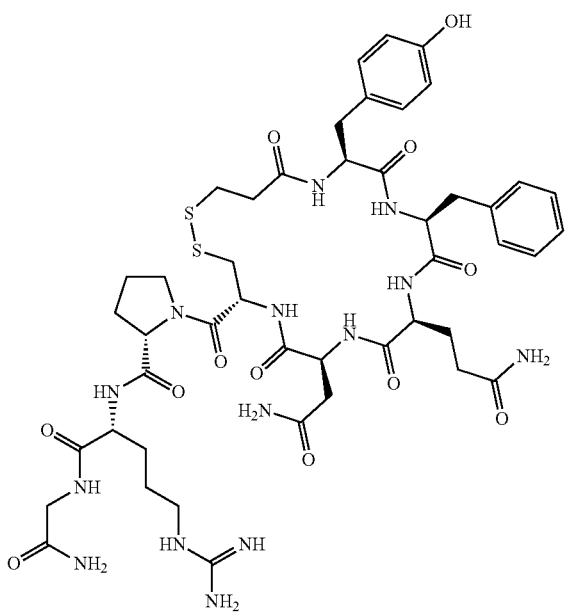 [SMILES: N=C(N)NCCC[C@@H](NC(=O)[C@@H]1CCCN1C(=O)[C@@H]1CSSCCC(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N1)C(=O)NCC(N)=O]

Cyclization Precursor:

LCMS: ESI (m/z): 1213 [M+H]+; eluted time: 7.6 minutes

Sample qNMR (Trifluoroacetate):

Measurement conditions: DMSO-d6, 23° C., pulse angle: 90°, digital resolution: 0.29 Hz, relaxation time: 60 seconds, no spin, accumulation number: 8 times CH proton of the α-carbon (three H in total, δ: 4.516-4.722 ppm) was used for quantification Internal standard: 3,5-dinitrobenzoic acid methyl ester Content: 86.2%

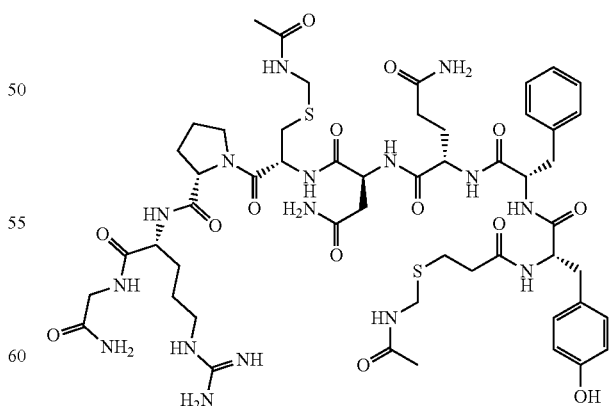

Dimer (cyclized form-1)

LCMS: ESI (m/z): 1070 [M+2H]2+; eluted time: 10.5 minutes

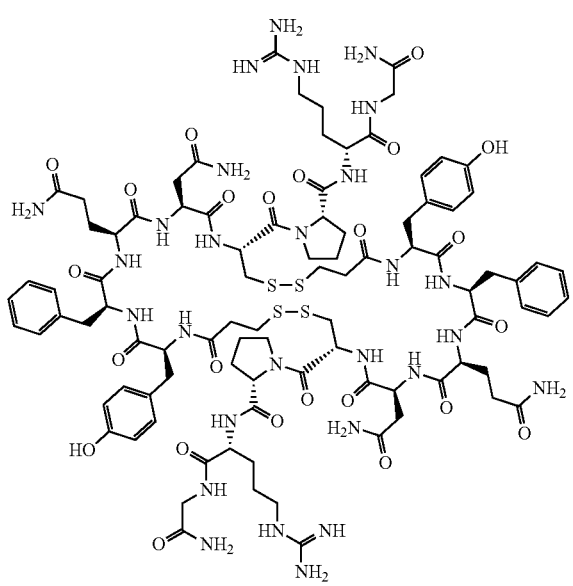 [SMILES: N=C(N)NCCC[C@@H](NC(=O)[C@@H]1CCCN1C(=O)[C@@H]1CSSCCC(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N[C@H](C(=O)N2CCC[C@H]2C(=O)N[C@H](CCCNC(=N)N)C(=O)NCC(N)=O)CSSCCC(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N1)C(=O)NCC(N)=O]
Dimer (cyclized form-2)
LCMS: ESI (m/z): 1070 [M+2H]$^{2+}$; eluted time: 12.2 minutes
Byproduct:
LCMS: ESI (m/z): 1195 [M+H]$^+$; eluted time: 11.6 minutes
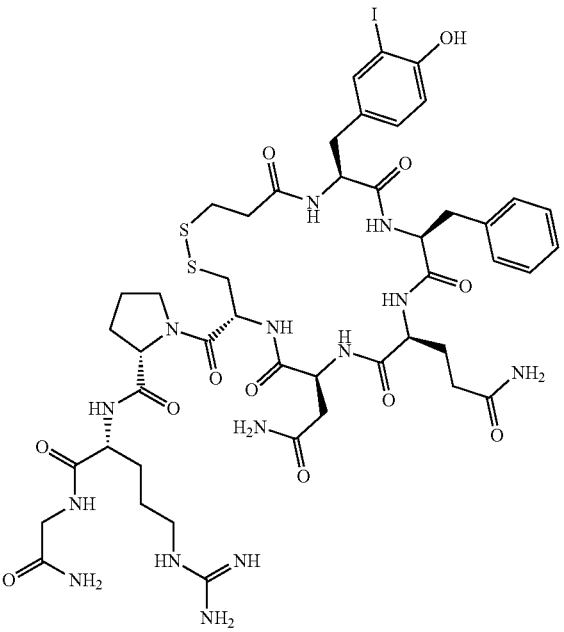 [SMILES: N=C(N)NCCC[C@@H](NC(=O)[C@@H]1CCCN1C(=O)[C@@H]1CSSCCC(=O)N[C@@H](Cc2ccc(O)c(I)c2)C(=O)N[C@@H](Cc2ccccc2)C(=O)N[C@@H](CCC(N)=O)C(=O)N[C@@H](CC(N)=O)C(=O)N1)C(=O)NCC(N)=O]
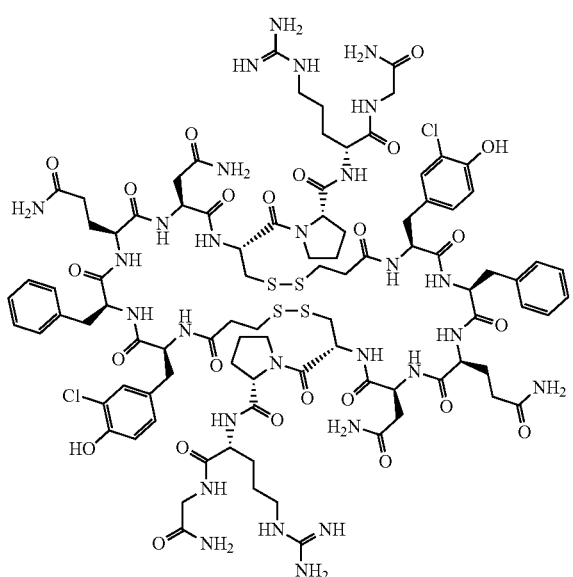
Results:
TABLE 26
| | Results of reaction purity in Runs 1-3: HPIE Area % (210 nm) | | | | |
|---|---|---|---|---|---|
| | Cyclization precursor | Target molecule | Dimer (cyclized form-1) | Dimer (cyclized form-2) | Byproduct |
| Run 1 | N. D. | 87.018 | 3.092 | 9.890 | N. D. |
| Run 2, after reaction | N. D. | 83.186 | 1.185 | 4.055 | 8.033 |
| Run 3, 240 minutes (4 θ) | N. D. | 98.316 | 0.407 | 1.070 | 0.207 |

TABLE 27

Time course of reaction purity in Run 3: HPLC Area % (210 mm)

| Time after starting operation | Cyclization precursor | Target molecule | Dimer (cyclized form-1) | Dimer (cyclized form-2) | Byproduct |
|---|---|---|---|---|---|
| 60 minutes (θ) | N. D | 98.507 | 0.329 | 0.894 | 0.270 |
| 120 minutes (2 θ) | N. D | 98.437 | 0.352 | 0.994 | 0.217 |
| 180 minutes (3 θ) | N. D | 98.349 | 0.383 | 1.072 | 0.196 |
| 240 minutes (4 θ) | N. D | 98.316 | 0.407 | 1.070 | 0.207 |
| After reaction | N. D | 98.000 | 0.364 | 1.043 | 0.593 |

TABLE 28

Comparison between simulation and experimental result (Run 2)

| | Run 2 | |
|---|---|---|
| | Simulation | Experimental result |
| Selectivity * | 0.998 | 0.946 |

In Run 2, some differences were observed between the simulation and experimental result. The reason is considered that when the cyclization precursor was added dropwise at a scale of Run 2, the reaction proceeded before it homogeneously dispersed due to the characteristic that the rate of this reaction is very fast, and it is considered that the simulation result will be in agreement with the experimental result when experiment is scaled up.

TABLE 29

Comparison between simulation and experimental result (Run 3)

| | Run 3 (4 θ) | |
|---|---|---|
| | Simulation | Experimental result |
| Reaction conversion rate* | 0.997 | 1.000 |
| Selectivity * | 0.999 | 0.985 |

* Calculation formulae Reaction conversion rate
Simulation: (Initial concentration of cyclization precursor-Cyclization precursor concentration)/Initial concentration of cyclization precursor
Experimental results: (Initial Area % of cyclization precursor-Area % of cyclization precursor)/Initial Area % of cyclization precursor
Selectivity Simulation: Concentration of target molecule/(Concentration of target molecule + Concentration of the Dimers (linear + cyclic))
Experimental results: Area % of target molecule + Area % of Byproduct/(Area % of target molecule + Area % of Byproduct + Area % of Dimers (linear + cyclic))
(Since Byproduct was formed by further iodination of target molecule, it was calculated together with the target molecule.)

Simulation and results from the experiment were confirmed to be roughly in agreement in Run 3.

Example 5 Synthesis of a Cyclosporin A Derivative

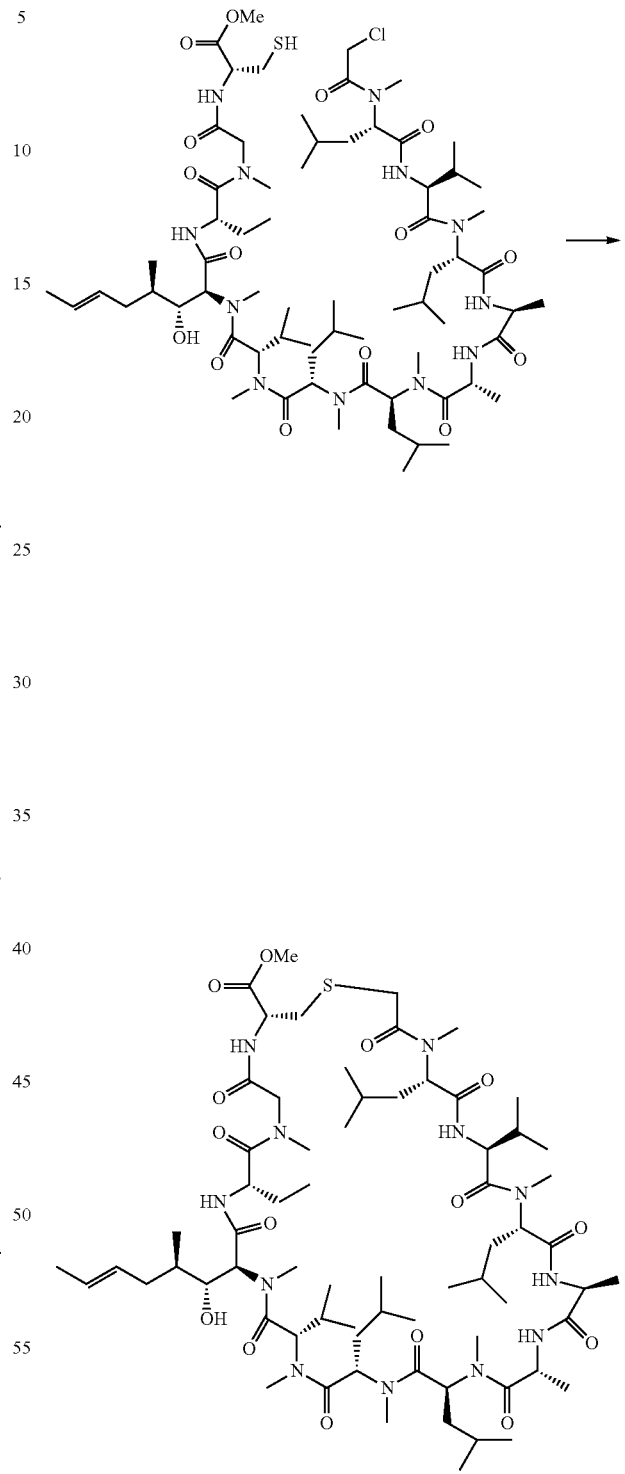

Protocol:

Synthesis of Cyclization Precursor 5

Cyclization precursor 5 was synthesized in three steps from the above-described Compound 2 (Cyclization precursor 2 in Example 2).

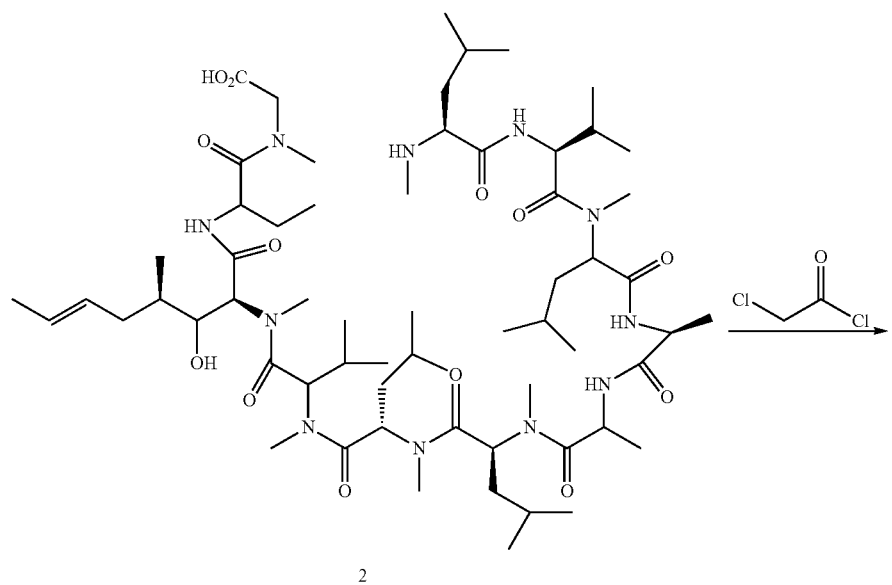
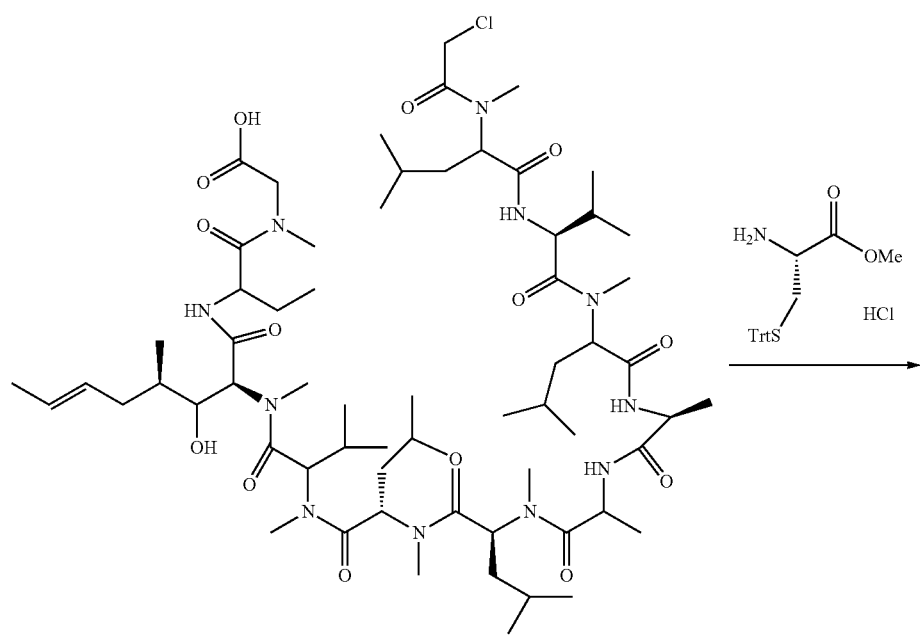

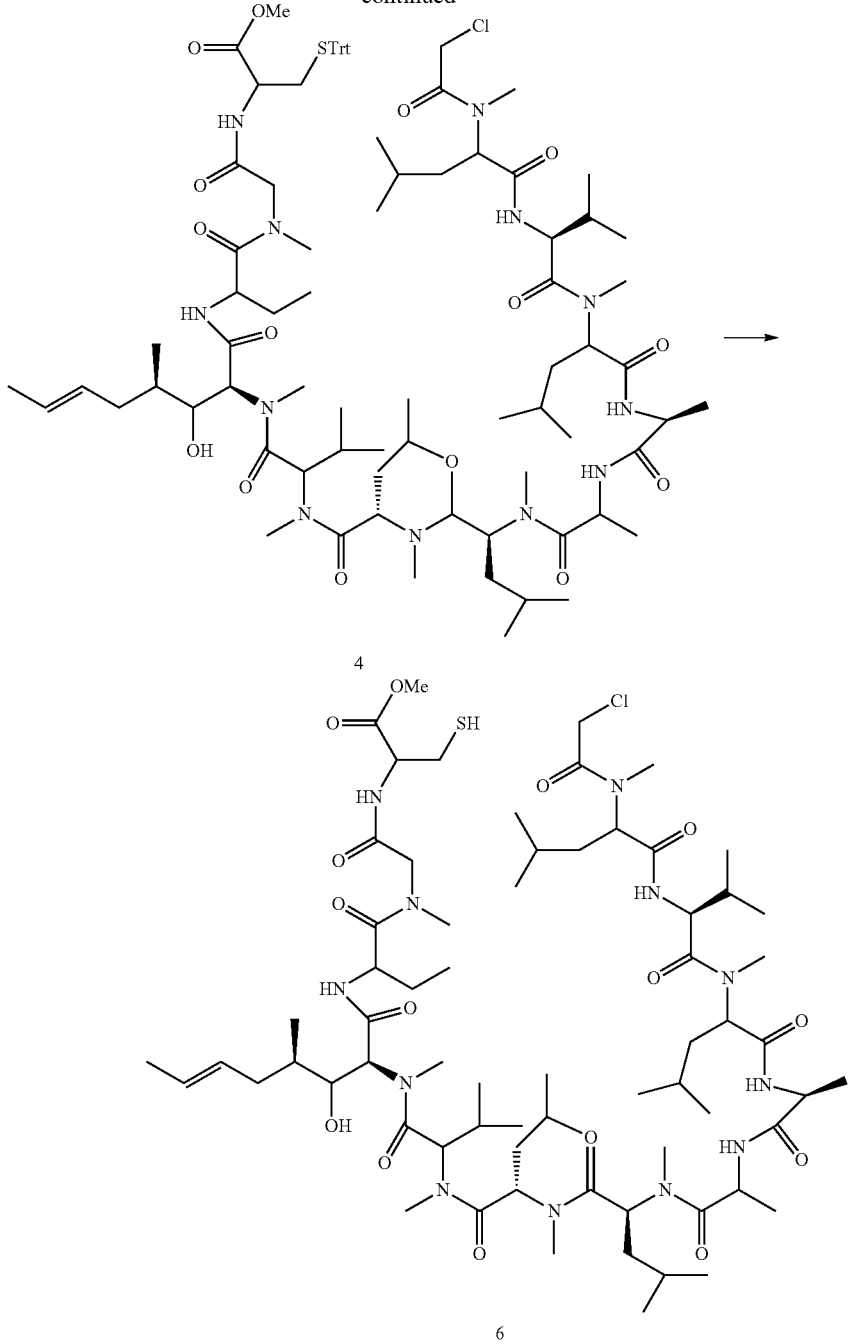

Preparation of Compound 3

The aforementioned Compound 2 (7.1 g) was dissolved in N,N-dimethylformamide (71 mL), and N,N-diisopropylethylamine (3 mL) and chloroacetyl chloride (1.85 mL) were added on ice. After stirring for two hours at room temperature, a 5% potassium hydrogen sulfate solution (100 mL) and ethyl acetate (100 mL) were added to the reaction solution, and then liquid separation was carried out. The organic layer was concentrated using an evaporator, and then purified by silica gel chromatography (ethyl acetate/heptane/methanol) to obtain Compound 3 (5.0 g) as a yellow oily liquid.

LCMS: ESI (m/z): 1297 [M+H]$^+$

Preparation of Compound 4

Compound 3 (5.0 g) obtained in the previous step was dissolved in N,N-dimethylformamide (50 mL), and S-trityl-L-cysteine methyl ester hydrochloride (4.0 g), HOAt (1.6 g), and EDC hydrochloride (2.6 g) were added. After stirring at room temperature for two hours, a saturated aqueous sodium hydrogen carbonate solution (100 mL) and ethyl acetate (100 mL) were added to the reaction solution, and liquid separation was carried out. The organic layer was concentrated using an evaporator, and then purified by silica gel chromatography (ethyl acetate/heptane/methanol) to obtain Compound 4 (4.7 g) as a yellow oily liquid.

LCMS: ESI (m/z): 1656 [M+]$^+$

Preparation of Cyclization Precursor 5

Compound 4 (4.7 g) obtained in the previous step was dissolved in dichloromethane (47 mL), and tri-isopropylsilane (3 mL) and trifluoroacetic acid (5.5 mL) were added on ice. After stirring at room temperature for one hour, the reaction solution was concentrated using an evaporator, and then the residue was purified by silica gel chromatography (ethyl acetate/heptane/methanol/trifluoroacetic acid). Further purification by reverse-phase chromatography (water/acetonitrile/trifluoroacetic acid) yielded Cyclization precursor 5 (2.1 g) as a white powder.

Reaction Rate Parameter Simulation

Data on change in concentration of each compound depending on the temperature/reaction time for each compound were collected to calculate reaction rate parameters. To the cyclization precursor (4.63 mM) prepared in a N,N-dimethylformamide (DMF) solution, N,N-diisopropylethylamine (DIPEA) (9.9 to 10.9 equiv.) was added, and this was allowed to react at 3° C., 24° C. or 46° C. The reaction was quenched using 0.5% TFA in an acetonitrile-water (1:1) solution. The change in reaction over time was traced by HPLC, and the data shown in Table 30 was obtained. The concentration of each compound was derived by converting the concentration of the cyclization precursor (4.63 mM) to an HPLC Area %. The absorption coefficient of the dimer was assumed to be twice that of the cyclization precursor and the absorption coefficient of the trimer was assumed to be three times that of the cyclization precursor to calculate the concentrations.

TABLE 30

Data on change in compound concentration (Example 5)

| Temperature (° C.) | Reaction time (sec) | Cyclization precursor (mM) | Target molecule (mM) | Dimer + Trimer (mM) |
|---|---|---|---|---|
| 3 | 0.5 | 2.95 | 1.03 | 0.31 |
| 3 | 4 | 0.78 | 2.49 | 0.64 |
| 3 | 12 | 0.21 | 2.99 | 0.68 |
| 24 | 0.5 | 2.39 | 1.56 | 0.33 |
| 24 | 2 | 0.70 | 2.93 | 0.47 |
| 24 | 8 | 0.09 | 3.52 | 0.48 |
| 36 | 0.25 | 2.19 | 1.99 | 0.22 |
| 36 | 1 | 0.53 | 3.53 | 0.27 |
| 36 | 2 | 0.15 | 3.93 | 0.27 |

From the obtained data, the mechanism of this cyclization reaction was considered to be the following. The reaction from the cyclization precursor and DIPEA to the intermediate was sufficiently fast; therefore, the rate of production of the target molecule and the dimer and trimer (multiple compounds) from the intermediate was considered to be the rate-limiting steps. While the concentration of the intermediate could not be measured, there may be no problem in calculating each of the parameters by assuming that the intermediate concentration and the raw material concentration obtained by analysis are equivalent since it is highly likely that the intermediate may return to the cyclization precursor by quenching before analysis, and also considering the aforementioned reaction rate difference. Furthermore, since DIPEA was used in excess amount with respect to the cyclization precursor and its effect on the reaction rate was small, it was omitted.

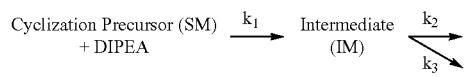

Cyclization Precursor (SM) + DIPEA $\xrightarrow{k_1}$ Intermediate (IM) $\underset{k_3}{\overset{k_2}{\rightrightarrows}}$ Cyclosporin A derivative (TM)

Dimer, Trimer (Dimer)

Using the data on concentration change over time and data on temperature obtained by the experiment (Table 30), the frequency factor (A) and activation energy (E) for each elementary reaction were determined using the equations below:

$$C_{SM} = C_{IM}$$

$$\frac{dC_{TM}}{dt} = k_2 C_{IM}$$

$$\frac{dC_{Dimer}}{dt} = k_3 C_{IM}^2$$

$$k_n = A_n \exp\left(\frac{-E_n}{RT}\right)$$

SM: cyclization precursor; IM: intermediate; TM: target molecule; Dimer: sum of dimers and trimers; C: concentration (M); kn: reaction rate constant; An: frequency factor; En: activation energy; T: temperature; R: gas constant Aspen custom modeler from Aspen Technology was used for the calculations. As a result, the data shown in Table 31 were obtained.

TABLE 31

Frequency factor (A) and activation energy (E) corresponding to reaction rate constants k1 and k2

|  | A | E [kJ/mol] |
|---|---|---|
| k1 | NA | NA |
| k2 | 82906.5 | 28071.8 |
| K3 | 63.1182 | 108.973 |

The reaction rate constants k2 and k3 when the temperature for carrying out the cyclization reaction in a CSTR is set to 25° C. were calculated from the obtained frequency factor (A) and activation energy (E) of each elementary reaction (Table 32).

TABLE 32

Reaction rate constant at 25° C. when performing cyclization reaction in CSTR

| Temperature | k1 | k2 | k3 |
|---|---|---|---|
| 25° C. | NA | 1.00 | 60.4 |

Next, the reaction conversion rate, selectivity, and residence time when the cyclization precursor concentration is set to 0.027 mol/L and the reaction temperature is set to 25° C. were calculated using the reaction rate constants k2 and k3 of Table 32, the mass balance equation and the reaction rate equations below (Table 33).

$$\tau = \frac{C_{0,n} - C_n}{-r_n}$$

$$\frac{dC_{TM}}{dt} = k_2 C_{IM}$$

-continued $$\frac{dC_{Dimer}}{dt} = k_3 C_{IM}^2$$

TABLE 33

Calculated reaction condition (when cyclization precursor concentration is 0.027 mol/L, reaction tempearture is 25° C.)

| | Reaction conversion rate* | Selectivity* | Residence time [θ, min] |
|---|---|---|---|
| Case 1 | 0.977 | 0.982 | 42 |
| Case 2 | 0.988 | 0.991 | 83 |
| Case 3 | 0.994 | 0.995 | 167 |

* Calculation formulae Reaction conversion rate: (Initial concentration of cyclization precursor-Cyclization precursor concentration)/Initial concentration of cyclization precursor
Selectivity: Concentration of target molecule/(Concentration of target molecule + Concentration of Dimer (dimer + trimer))

In Cases 1 to 3 of Table 33, residence time that will yield results in which the reaction conversion rate and selectivity become high were determined by calculation. In the present Example, Case 3 was carried out.

Run 1: Batch High-Dilution

The cyclization precursor (49.7 mg, 77.3% content, 0.0272 mmol) was dissolved in DMF (8.8 mL), and DIPEA (0.28 mmol, 10 equiv.) was added to this mixture at room temperature. The obtained mixture was allowed to react at room temperature for one hour. A portion of the reaction solution was quenched using 0.5% trifluoroacetic acid in an acetonitrile-water (1:1) solution, and when the solution concentration of the target molecule was quantified to calculate the yield, it corresponded to 30.8 mg (82% yield).

Run 2: Batch Pseudo High-Dilution

To a solution of DIPEA (1.72 mmol, 10 equiv.) in DMF (7.5 mL), a solution of the cyclization precursor compound (300.9 mg, 77.3% content, 0.164 mmol) in DMF (4.6 mL) was added dropwise at 22° C. over a period of three hours. Approximately one hour after the dropwise addition, when the solution concentration of the target molecule was quantified to calculate the yield, it corresponded to 187.3 mg (83% yield).

Run 3: CSTR

The cyclization precursor (1.3671 g, 77.3% content, 0.747 mmol) was dissolved in DMF (27.3 mL). The substrate concentration was 0.027 mmol/mL. On the other hand, DIPEA (7.73 mmol, 10 equiv.) was dissolved in DMF (27.3 mL). The reagent concentration was 0.283 mmol/mL. These solutions were added to DMF (13.2 mL) at 23° C. respectively at an input speed of 0.04 mL/min, and the reaction solutions were drawn out at an output speed of 0.08 mL/min at the same time. Sampling was performed by collecting the reaction solution at 165 minutes (θ*), 330 minutes (2θ), 495 minutes (3θ), and 660 minutes (4θ) after starting the operation, and quenching it with 0.5% trifluoroacetic acid in an acetonitrile-water (1:1) solution. When all of the output solutions were put together and the concentration was quantified to calculate the yield, it corresponded to 793.9 mg (82% yield). The yield was calculated based on the amount of raw material solution used for the input (94.5% of the total amount).

*θ=elapsed time/average residence time

Analysis Conditions:

HPLC and LCMS conditions:

Column: Kinetex Biphenyl, 2.1 mm I.D.×150 mm, 2.6 μm

Mobile phase: A) water:TFA=2000:1; B) acetonitrile:TFA=2000:1

Column temperature: 60° C.

Flow rate: 0.5 mL/min

Gradient (B %): 0 to 30 min (10→100), 30.0 to 30.6 min (100), 30.7 min and thereafter (10).

MS detection mode: ESI (LC/MS): m/z

Target molecule (Cyclosporin A derivative):

LCMS: ESI (m/z): 1378 [M+H]+; eluted time: 17.5 minutes

The yield was quantified by an HPLC assay that used the following sample.

Sample qNMR:

Measurement conditions: DMSO-d6, 147° C., pulse angle: 90°, digital resolution: 0.25 Hz, relaxation time: 60 seconds, no spin, accumulation number: 32 times CH proton of the n-carbon of MeVal (one H in total) was used for quantification Internal standard: maleic acid Content: 94.4%

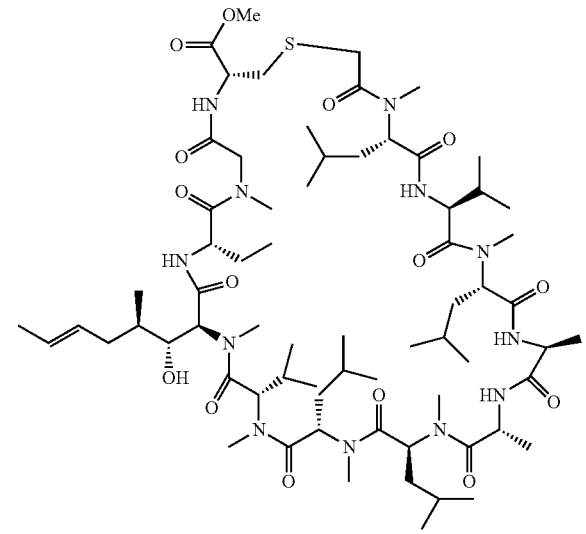 [SMILES: C/C=C/C[C@@H](C)[C@@H](O)[C@H]1C(=O)N[C@@H](CC)C(=O)N(C)CC(=O)N[C@H](C(=O)OC)CSCC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Cyclization Precursor:

LCMS: ESI (m/z): 1414 [M+H]+, eluted time: 13.9 minutes

Content: 77.3% as determined by qNMR and HPLC assay a. Sample qNMR:

Measurement conditions: DMSO-d6, 90° C., pulse angle: 90°, digital resolution: 0.25 Hz, relaxation time: 60 seconds, no spin, accumulation number: 32 times CH proton of the n-carbon of MeVal (one H in total) was used for quantification Internal standard: 3,5-bis(trifluoromethyl)benzoic acid Content: 91.8% b. Result of performing an HPLC assay using the raw material used in the present Example as a sample: 84.2%

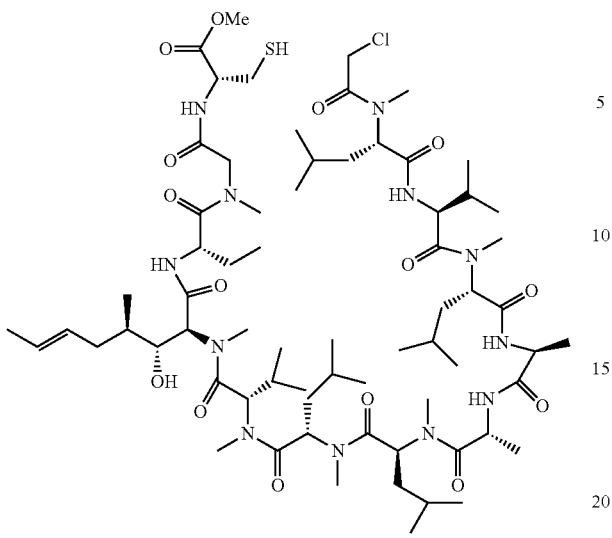
Dimer
LCMS: ESI (m/z): 1378 [M+2H]$^{2+}$, eluted time: 21.8 minutes
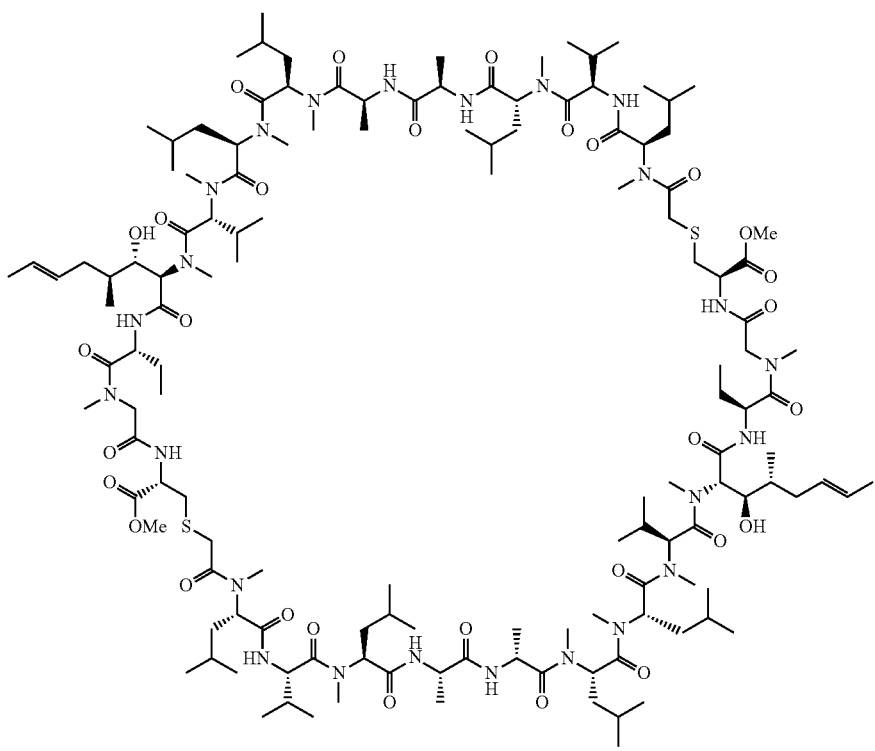 [SMILES: C/C=C/C[C@@H](C)[C@@H](O)[C@H]1C(=O)N[C@@H](CC)C(=O)N(C)CC(=O)N[C@H](C(=O)OC)CSCC(=O)N(C)[C@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@@H](O)[C@@H](C)C/C=C/C)C(=O)N[C@H](CC)C(=O)N(C)CC(=O)N[C@@H](C(=O)OC)CSCC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]
Trimer
LCMS: ESI (m/z): 1378 [M+3H]$^{3+}$, eluted time: 24.1 minutes

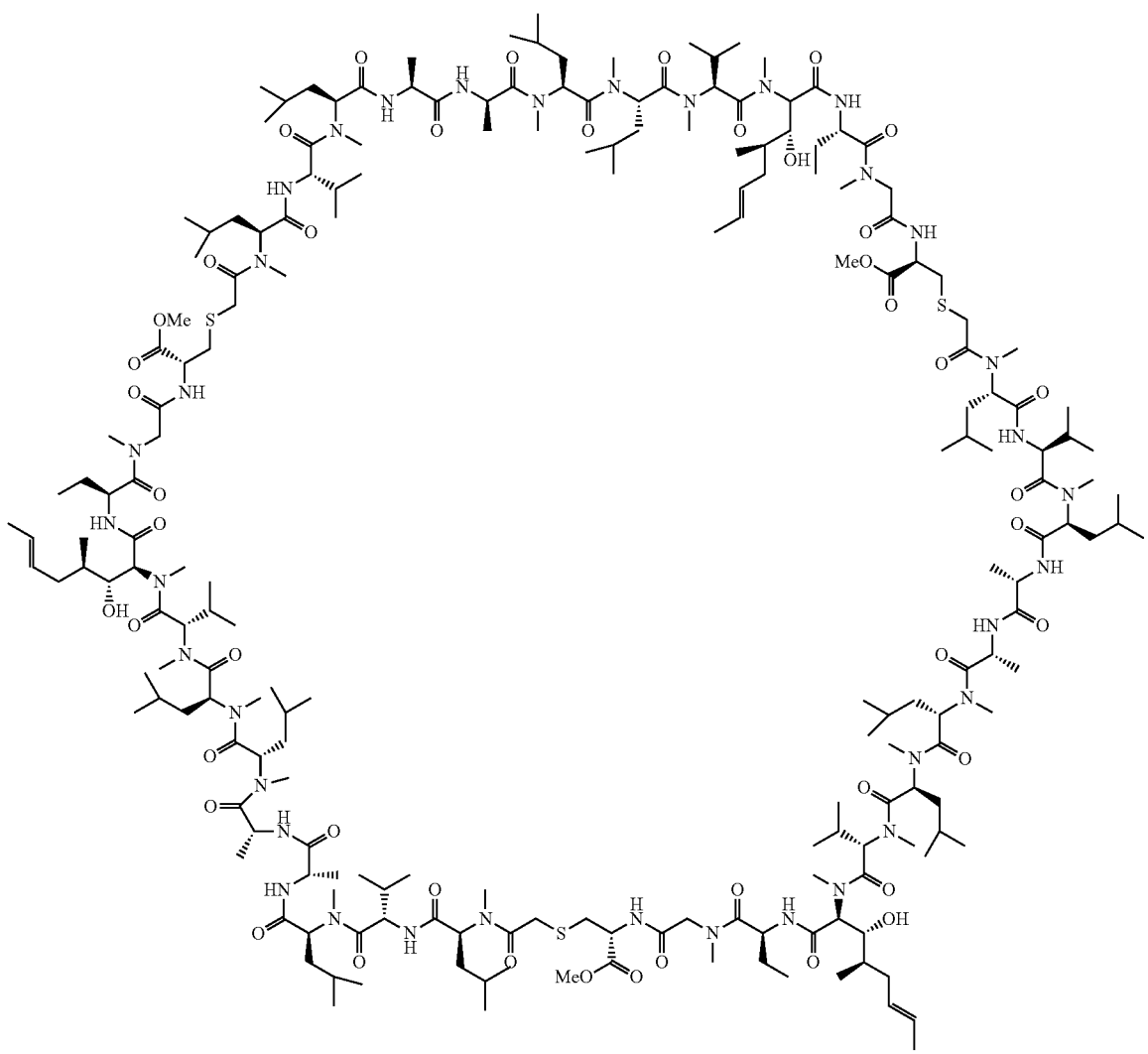

Results:

TABLE 34

Results of reaction purity in Runs 1-3: HPLC Area % (210 nm)

| | Cyclization precursor | Target molecule | Dimer | Trimer |
|---|---|---|---|---|
| Run 1 | N. D. | 64.55 | 12.39 | 1.59 |
| Run 2, after reaction | N. D. | 67.65 | 3.70 | N. D. |
| Run 3, 660 min (4 θ) | 0.64 | 64.65 | 2.21 | N. D. |

TABLE 35

Time course of reaction purity in Run 3: HPLC Area % (2.10 nm)

| Time after starting operation | Cyclization precursor | Target molecule | Dimer | Trimer |
|---|---|---|---|---|
| 165 minutes (θ) | 1.11 | 70.98 | 1.92 | N. D. |
| 330 minutes (2 θ) | 0.79 | 67.97 | 2.11 | N. D. |

TABLE 35-continued

Time course of reaction purity in Run 3: HPLC Area % (2.10 nm)

| Time after starting operation | Cyclization precursor | Target molecule | Dimer | Trimer |
|---|---|---|---|---|
| 495 minutes (3 θ) | 0.86 | 65.22 | 2.14 | N. D. |
| 660 minutes (4 θ) | 0.64 | 64.65 | 2.21 | N. D. |
| After reaction | N. D. | 66.27 | 2.60 | N. D. |

TABLE 36

Comparison between simulation and experimental result (Run 2)

| | Run 2 | |
|---|---|---|
| | Simulation | Experimental result |
| Selectivity * | 0.994 | 0.948 |

In Run 2, some differences were observed between the simulation and experimental result. The reason was considered that when the cyclization precursor was added dropwise at a scale of Run 2, the reaction proceeded before it homogeneously dispersed due to the characteristic that the rate of this reaction is very fast, and it was considered that the simulation result will be in agreement with the experimental result when experiment is scaled up.

TABLE 37

*Comparison between simulation and experimental result (Run 3)*

| | Run 3 (4 θ) | |
|---|---|---|
| | Simulation | Experimental result |
| Reaction conversion rate* | 0.994 | 0.991 |
| Selectivity * | 0.995 | 0.967 |

Simulation and the experimental result were confirmed to be roughly in agreement in Run 3.

Calculation Formulae

Reaction Conversion Rate

Simulation: (Initial concentration of cyclization precursor−Cyclization precursor concentration)/Initial concentration of cyclization precursor Experimental results: (Initial Area % of cyclization precursor−Area % of cyclization precursor)/Initial Area % of cyclization precursor Selectivity Simulation: Concentration of target molecule/(Concentration of target molecule+concentration of Dimer+Trimer))

Experimental result: (Area % of target molecule)/(Area % of target molecule+Area % of Dimer+Trimer)

INDUSTRIAL APPLICABILITY

The present invention provides novel methods of producing a cyclic organic compound, which comprise performing a cyclization reaction using a CSTR(s), and the like. The inventions provided by the present invention are useful in continuously producing cyclic organic compounds in a smaller reaction tank(s), and with less impurity.

The invention claimed is:

1. A method of producing a peptide compound, wherein the peptide compound is composed of natural amino acids and/or amino acid analogs, and wherein the peptide compound comprises a cyclic portion consisting of 4 to 14 natural amino acid and/or amino acid analog residues,
   wherein the amino acid analog is a hydroxycarboxylic acid or an amino acid represented by the following formula: X-A-C(=O)—OH,
   wherein:
   X is —NH$_2$ or —NHR$_N$;
   A is —C(R$_1$)(R$_2$)—, —C(R$_1$)(R$_2$)—C(R$_3$)(R$_4$)—, or —C(R$_1$)(R$_2$)—C(R$_3$)(R$_4$)—C(R$_5$)(R$_6$)—, wherein the carbon atom attached to R$_1$ and R$_2$ is bonded to X;
   R$_N$ is an alkyl, an alkenyl, an alkynyl, an aryl, a heteroaryl, an aralkyl, or a cycloalkyl, each of which is optionally substituted;
   R$_1$, R$_2$, R$_3$, R$_4$, R$_5$, and R$_6$ are each independently a hydrogen atom or an optional substituted group selected from an alkyl, an alkenyl, an alkynyl, an aryl, a heteroaryl, an aralkyl, or a cycloalkyl;
   or R$_N$ and R$_1$ together represent a carbon chain bonded to the N atom and the carbon atom at the α position thereby forming a ring;
   provided that the amino acid analog is not a natural amino acid,
   the method comprises a cyclization reaction step of cyclizing a cyclization precursor of the peptide compound in at least one continuous stirred tank reactor (CSTR).

2. The method of claim 1, wherein the total number of natural amino acid and amino acid analog residues in the peptide compound is 7 to 20.

3. The method of claim 2, wherein the cyclic organic peptide compound has the following features:
   (i) comprising at least two N-substituted amino acids, and at least one non-N-substituted amino acid; and
   (ii) having a C log P value of 6 or greater.

4. The method of claim 1, wherein the cyclization reaction is an intramolecular cyclization reaction through one or more bonds selected from the group consisting of the following:
   (i) an amide bond;
   (ii) a disulfide bond;
   (iii) an ether bond;
   (iv) a thioether bond;
   (v) an ester bond;
   (vi) a thioester bond; and
   (vii) a carbon-carbon bond.

5. The method of claim 1, wherein the cyclization reaction is performed at an industrial scale using a condition obtained based on a result from a preliminary test of the cyclization reaction.

6. The method of claim 5, wherein the condition is obtained by steps comprising the following:
   (i) obtaining data on concentration change over time at multiple temperatures for at least one selected from the group consisting of the cyclization precursor, the cyclic organic peptide compound, one or more intermediates, and one or more byproducts, in the preliminary test;
   (ii) determining a reaction rate constant k$_n$ by using the data on concentration change obtained in step (i) and a reaction rate equation relating to the cyclization reaction;
   (iii) determining frequency factor A$_n$ and activation energy E$_n$ by using the temperatures used in step (i), the reaction rate constant k$_n$ determined in step (ii), and the following equation (II):

$$k_n = A_n \exp\left(\frac{-E_n}{RT}\right) \qquad (II)$$

(iv) determining a reaction rate constant k$_n$ at a temperature for cyclization in a CSTR(s) by using the frequency factor A$_n$ and activation energy E$_n$ determined in step (iii), the above-mentioned equation (II), and the above-mentioned reaction rate equation; and
   (v) obtaining the aforementioned condition using the reaction rate constant k$_n$ determined in step (iv), the aforementioned reaction rate equation, and the following CSTR mass balance equation (III):

$$\tau = \frac{C_{0,n} - C_n}{-r_n} \qquad (III)$$

wherein $r_n$ represents the reaction rate of the variable n, $\tau$ represents the residence time, $C_{0,n}$ represents the supply concentration of the variable n, and $C_n$ represents the effluent concentration of the variable n.

7. The method of claim 6, wherein the elementary reactions of the cyclization reaction are presented by (a) formula (IV) below:

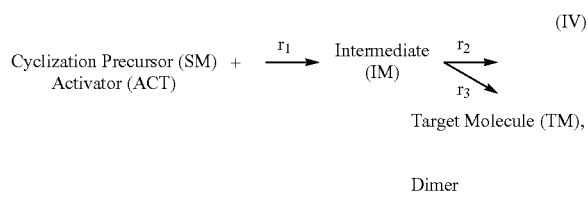

(IV)

and the reaction rate constants $k_1$, $k_2$, and $k_3$ are determined using any of equations (V) to (IX) below:

$$r_{SM} = \frac{dC_{SM}}{dt} = -k_1 C_{SM} C_{ACT} \quad (V)$$

$$r_{ACT} = \frac{dC_{ACT}}{dt} = -k_1 C_{SM} C_{ACT} \quad (VI)$$

$$r_{IM} = \frac{dC_{IM}}{dt} = k_1 C_{SM} C_{ACT} - k_2 C_{IM} - 2k_3 C_{IM}^2 \quad (VII)$$

$$r_{TM} = \frac{dC_{TM}}{dt} = k_2 C_{IM} \quad (VIII)$$

$$r_{Dimer} = \frac{dC_{Dimer}}{dt} = k_3 c_{IM}^2 \quad (IX)$$

wherein TM represents the peptide compound, SM represents the cyclization precursor, ACT represents the activator, IM represents the intermediate, Dimer represents the dimer, and C represents the molar concentration; or (b) formula (X) below:

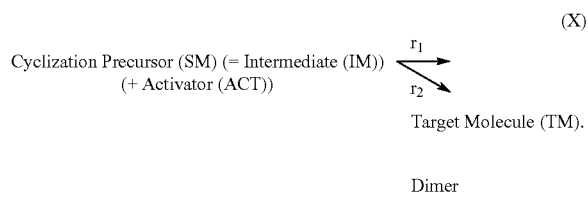

(X)

and the reaction rate constants $k_1$ and $k_2$ are determined using any of equations (XI) to (XIII) below:

$$r_{SM} = \frac{dC_{SM}}{dt} = \frac{dC_{ACT}}{dt} = -k_1 C_{SM} C_{ACT} - 2k_2 C_{SM}^2 C_{ACT}^2 \quad (XI)$$

$$r_{TM} = \frac{dC_{TM}}{dt} = k_1 C_{SM} C_{ACT} \quad (XII)$$

$$r_{Dimer} = \frac{dC_{Dimer}}{dt} = k_2 C_{SM}^2 C_{ACT}^2 \quad (XIII)$$

wherein r represents the reaction rate, TM represents the target molecule, SM represents the cyclization precursor, ACT represents the activator, Dimer represents the dimer, and C represents the molar concentration.

8. The method of claim 5, wherein the condition is selected from the group consisting of flow volume in the continuous stirred tank reactor, concentration of the cyclization precursor, and concentration of the peptide compound.

9. A method of promoting intramolecular cyclization of a cyclization precursor of a peptide compound, wherein the peptide compound is composed of natural amino acids and/or amino acid analogs, and wherein the peptide compound comprises a cyclic portion consisting of 4 to 14 natural amino acid and/or amino acid analog residues, wherein the amino acid analog is a hydroxycarboxylic acid or an amino acid represented by the following formula: X-A-C(=O)—OH, wherein:

X is —$NH_2$ or —$NHR_N$;

A is —$C(R_1)(R_2)$—, —$C(R_1)(R_2)$—$C(R_3)(R_4)$—, or —$C(R_1)(R_2)$—$C(R_3)(R_4)$—$C(R_5)(R_6)$—, wherein the carbon atom attached to $R_1$ and $R_2$ is bonded to X;

$R_N$ is an alkyl, an alkenyl, an alkynyl, an aryl, a heteroaryl, an aralkyl, or a cycloalkyl, each of which is optionally substituted;

$R_1$, $R_2$, $R_3$, $R_4$, $R_5$, and $R_6$ are each independently a hydrogen atom, an optional substituted group selected from an alkyl, an alkenyl, an alkynyl, an aryl, a heteroaryl, an aralkyl, or a cycloalkyl;

or $R_N$ and $R_1$ together represent a carbon chain bonded to the N atom and the carbon atom at the α position thereby forming a ring;

provided that the amino acid analog is not a natural amino acid, the method comprises a step of cyclizing the cyclization precursor in at least one continuous stirred tank reactor (CSTR).

10. The method of claim 2, wherein the cyclization reaction is an intramolecular cyclization reaction through one or more bonds selected from the group consisting of the following:

(i) an amide bond;
(ii) a disulfide bond;
(iii) an ether bond;
(iv) a thioether bond;
(v) an ester bond;
(vi) a thioester bond; and
(vii) a carbon-carbon bond.

11. The method of claim 3, wherein the cyclization reaction is an intramolecular cyclization reaction through one or more bonds selected from the group consisting of the following:

(i) an amide bond;
(ii) a disulfide bond;
(iii) an ether bond;
(iv) a thioether bond;
(v) an ester bond;
(vi) a thioester bond; and
(vii) a carbon-carbon bond.

12. The method of claim 2, wherein the cyclization reaction is performed at an industrial scale using a condition obtained based on a result from a preliminary test of the cyclization reaction.

13. The method of claim 3, wherein the cyclization reaction is performed at an industrial scale using a condition obtained based on a result from a preliminary test of the cyclization reaction.

14. The method of claim 12, wherein the condition is obtained by steps comprising the following:
  (i) obtaining data on concentration change over time at multiple temperatures for at least one selected from the group consisting of the cyclization precursor, the peptide compound, one or more intermediates, and one or more byproducts, in the preliminary test;
  (ii) determining a reaction rate constant $k_n$ by using the data on concentration change obtained in step (i) and a reaction rate equation relating to the cyclization reaction;
  (iii) determining frequency factor $A_n$ and activation energy $E_n$ by using the temperatures used in step (i), the reaction rate constant $k_n$ determined in step (ii), and the following equation (II):

$$k_n = A_n \exp\left(\frac{-E_n}{RT}\right); \tag{II}$$

(iv) determining a reaction rate constant $k_n$ at a temperature for cyclization in a CSTR(s) by using the frequency factor $A_n$ and activation energy $E_n$ determined in step (iii), the above-mentioned equation (II), and the above-mentioned reaction rate equation; and
  (v) obtaining the aforementioned condition using the reaction rate constant $k_n$ determined in step (iv), the aforementioned reaction rate equation, and the following CSTR mass balance equation (III):

$$\tau = \frac{C_{0,n} - C_n}{-r_n} \tag{III}$$

wherein $r_n$ represents the reaction rate of the variable n, $\tau$ represents the residence time, $C_{0,n}$ represents the supply concentration of the variable n, and $C_n$ represents the effluent concentration of the variable n.

15. The method of claim 13, wherein the condition is obtained by steps comprising the following:
  (i) obtaining data on concentration change over time at multiple temperatures for at least one selected from the group consisting of the cyclization precursor, the peptide compound, one or more intermediates, and one or more byproducts, in the preliminary test;
  (ii) determining a reaction rate constant $k_n$ by using the data on concentration change obtained in step (i) and a reaction rate equation relating to the cyclization reaction;
  (iii) determining frequency factor $A_n$ and activation energy $E_n$ by using the temperatures used in step (i), the reaction rate constant $k_n$ determined in step (ii), and the following equation (II):

$$k_n = A_n \exp\left(\frac{-E_n}{RT}\right) \tag{II}$$

(iv) determining a reaction rate constant $k_n$ at a temperature for cyclization in a CSTR(s) by using the frequency factor $A_n$ and activation energy $E_n$ determined in step (iii), the above-mentioned equation (II), and the above-mentioned reaction rate equation; and
  (v) obtaining the aforementioned condition using the reaction rate constant $k_n$ determined in step (iv), the aforementioned reaction rate equation, and the following CSTR mass balance equation (III):

$$\tau = \frac{C_{0,n} - C_n}{-r_n} \tag{III}$$

wherein $r_n$ represents the reaction rate of the variable n, $\tau$ represents the residence time, $C_{0,n}$ represents the supply concentration of the variable n, and $C_n$ represents the concentration of the variable n.

16. The method of claim 14, wherein the elementary reactions of the cyclization reaction are presented by
  (a) formula (IV) below:

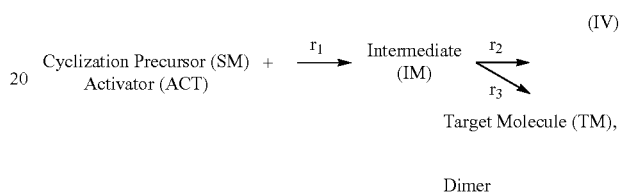

and the reaction rate constants $k_1$, $k_2$, and $k_3$ are determined using any of equations (V) to (IX) below:

$$r_{SM} = \frac{dC_{SM}}{dt} = -k_1 C_{SM} C_{ACT} \tag{V}$$

$$r_{ACT} = \frac{dC_{ACT}}{dt} = -k_1 C_{SM} C_{ACT} \tag{VI}$$

$$r_{IM} = \frac{dC_{IM}}{dt} = k_1 C_{SM} C_{ACT} - k_2 C_{IM} - 2k_3 C_{IM}^2 \tag{VII}$$

$$r_{TM} = \frac{dC_{TM}}{dt} = k_2 C_{IM} \tag{VIII}$$

$$r_{Dimer} = \frac{dC_{Dimer}}{dt} = k_3 C_{IM}^2 \tag{IX}$$

wherein TM represents the peptide compound, SM represents the cyclization precursor, ACT represents the activator, IM represents the intermediate, Dimer represents the dimer, and C represents the molar concentration; or
  (b) formula (X) below:

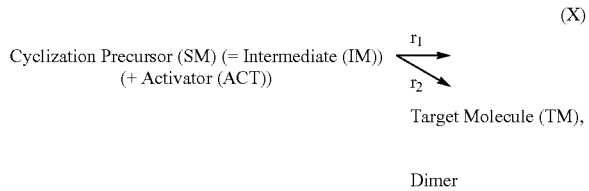

and the reaction rate constants $k_1$ and $k_2$ are determined using any of equations (XI) to (XIII) below:

$$r_{SM} = \frac{dC_{SM}}{dt} = \frac{dC_{ACT}}{dt} = -k_1 C_{SM} C_{ACT} - 2k_2 C_{SM}^2 C_{ACT}^2 \tag{XI}$$

-continued $$r_{TM} = \frac{dC_{TM}}{dt} = k_1 C_{SM} C_{ACT} \quad \text{(XII)}$$

$$r_{Dimer} = \frac{dC_{Dimer}}{dt} = k_2 C_{SM}^2 C_{ACT}^2 \quad \text{(XIII)}$$

wherein r represents the reaction rate, TM represents the target molecule, SM represents the cyclization precursor, ACT represents the activator, Dimer represents the dimer, and C represents the molar concentration.

17. The method of claim 15, wherein the elementary reactions of the cyclization reaction are presented by
(a) formula (IV) below:

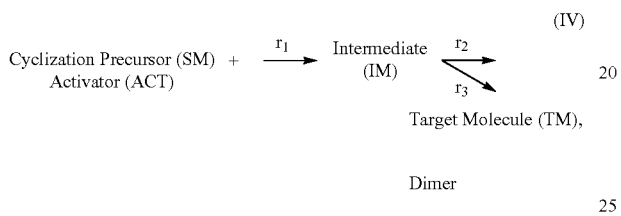
(IV)

and the reaction rate constants $k_1$, $k_2$, and $k_3$ are determined using any of equations (V) to (IX) below:

$$r_{SM} = \frac{dC_{SM}}{dt} = -k_1 C_{SM} C_{ACT} \quad \text{(V)}$$

$$r_{ACT} = \frac{dC_{ACT}}{dt} = -k_1 C_{SM} C_{ACT} \quad \text{(VI)}$$

$$r_{IM} = \frac{dC_{IM}}{dt} = k_1 C_{SM} C_{ACT} - k_2 C_{IM} - 2k_3 C_{IM}^2 \quad \text{(VII)}$$

$$r_{TM} = \frac{dC_{TM}}{dt} = k_2 C_{IM} \quad \text{(VIII)}$$

$$r_{Dimer} = \frac{dC_{Dimer}}{dt} = k_3 C_{IM}^2 \quad \text{(IX)}$$

wherein TM represents the peptide compound, SM represents the cyclization precursor, ACT represents the activator, IM represents the intermediate, Dimer represents the dimer, and C represents the molar concentration; or (b) formula (X) below:

(X)

and the reaction rate constants $k_1$ and $k_2$ are determined using any of equations (XI) to (XIII) below:

$$r_{SM} = \frac{dC_{SM}}{dt} = \frac{dC_{ACT}}{dt} = -k_1 C_{SM} C_{ACT} - 2k_2 C_{SM}^2 C_{ACT}^2 \quad \text{(XI)}$$

$$r_{TM} = \frac{dC_{TM}}{dt} = k_1 C_{SM} C_{ACT} \quad \text{(XII)}$$

$$r_{Dimer} = \frac{dC_{Dimer}}{dt} = k_2 C_{SM}^2 C_{ACT}^2 \quad \text{(XIII)}$$

wherein r represents the reaction rate, TM represents the target molecule, SM represents the cyclization precursor, ACT represents the activator, Dimer represents the dimer, and C represents the molar concentration.

18. The method of claim 12, wherein the condition is selected from the group consisting of flow volume in the continuous stirred tank reactor, concentration of the cyclization precursor, and concentration of the cyclic organic peptide compound.

19. The method of claim 13, wherein the condition is selected from the group consisting of flow volume in the continuous stirred tank reactor, concentration of the cyclization precursor, and concentration of the peptide compound.

* * * * *